(12) United States Patent
Vergoullis et al.

(10) Patent No.: US 10,136,974 B2
(45) Date of Patent: Nov. 27, 2018

(54) MOLDS FOR CUSTOM DENTAL IMPLANT ABUTMENTS AND IMPRESSION POSTS

(71) Applicant: GP INNOVATO CYPRUS LTD, Limassol (CY)

(72) Inventors: Ioannis Vergoullis, Rhodes (GR); Georgios Papadopoulos, Rhodes (GR)

(73) Assignee: VP INNOVATO HOLDINGS LTD, Limassol (CY)

( * ) Notice: Subject to any disclaimer, the term of this patent is extended or adjusted under 35 U.S.C. 154(b) by 65 days.

(21) Appl. No.: 15/318,085

(22) PCT Filed: Jun. 12, 2015

(86) PCT No.: PCT/GR2015/000029
§ 371 (c)(1),
(2) Date: Dec. 12, 2016

(87) PCT Pub. No.: WO2015/189647
PCT Pub. Date: Dec. 17, 2015

(65) Prior Publication Data
US 2017/0128176 A1 May 11, 2017

(30) Foreign Application Priority Data

Jun. 13, 2014 (GR) .............................. 20140100327
Dec. 16, 2014 (GR) .............................. 20140100642
(Continued)

(51) Int. Cl.
*A61C 13/20* (2006.01)
*A61C 8/00* (2006.01)
(Continued)

(52) U.S. Cl.
CPC ............ *A61C 13/206* (2013.01); *A61C 1/084* (2013.01); *A61C 8/0001* (2013.01); *A61C 8/005* (2013.01);
(Continued)

(58) Field of Classification Search
CPC ..... A61C 8/0001; A61C 8/008; A61C 8/0089; A61C 9/0006
See application file for complete search history.

(56) References Cited

U.S. PATENT DOCUMENTS 512,840 A * 1/1894 Phelps, Jr. ............. A61C 13/20
164/376
5,180,303 A * 1/1993 Hornburg ............. A61C 8/0048
433/173
(Continued)

FOREIGN PATENT DOCUMENTS

| EP | 2343025 A2 | 7/2011 |
|---|---|---|
| KR | 20100048968 A | 5/2010 |
| KR | 2502328 A | 11/2013 |

OTHER PUBLICATIONS

Albrektsson et al. "Osseointegrated dental implants" Dent. Clin. North Am.; Jan. 1986; 30(1); pp. 151-174.
(Continued)

*Primary Examiner* — Nicholas Lucchesi
*Assistant Examiner* — Shannel Wright
(74) *Attorney, Agent, or Firm* — Steinfl + Bruno LLP

(57) ABSTRACT

Molds for fabrication of custom and potentially modifiable abutments and impression posts for dental implants with various degrees of angulations (including zero degrees) and various dimensions are provided, with a generally oval shape that expands laterally upwards, a symmetrical or asymmetrical cross-section, and regular surfaces, that are fabricated as one piece, or as two coupling pieces snapping onto each other. Custom abutments achieve the development
(Continued)

of a custom gingival emergence profile, three dimensionally, which is potentially modifiable according to the needs of each particular clinical case. Custom impression posts that correspond in dimensions and angulations to the abutments allow the accurate recording and transfer of the developed gingival emergence profile from the mouth onto the working cast, where the final implant prosthesis is fabricated. Custom abutments and impression posts have properties and design that allows their preparation and usage as temporary abutments for the cementation and support of temporary prostheses.

7 Claims, 32 Drawing Sheets

(30) Foreign Application Priority Data

Mar. 4, 2015 (GR) .............................. 20150100090
Mar. 12, 2015 (GR) .............................. 20150100111

(51) Int. Cl.
*A61C 9/00* (2006.01)
*A61C 13/00* (2006.01)
*A61C 19/04* (2006.01)
*A61C 1/08* (2006.01)
*A61C 13/107* (2006.01)
*A61C 13/15* (2006.01)

(52) U.S. Cl.
CPC .............. *A61C 8/008* (2013.01); *A61C 8/009* (2013.01); *A61C 8/0053* (2013.01); *A61C 8/0056* (2013.01); *A61C 8/0063* (2013.01); *A61C 8/0068* (2013.01); *A61C 8/0089* (2013.01); *A61C 9/00* (2013.01); *A61C 9/0006* (2013.01); *A61C 9/0053* (2013.01); *A61C 13/0001* (2013.01); *A61C 13/0003* (2013.01); *A61C 13/0022* (2013.01); *A61C 19/003* (2013.01); *A61C 19/04* (2013.01)

(56) References Cited

U.S. PATENT DOCUMENTS

| | | | | |
|---|---|---|---|---|
| 5,759,036 A * | 6/1998 | Hinds | ................... | A61C 8/005 433/172 |
| 5,846,079 A * | 12/1998 | Knode | ................... | A61C 8/00 433/213 |
| 6,672,871 B2 * | 1/2004 | Hurson | ................ | A61C 8/0001 433/172 |
| 7,922,488 B2 * | 4/2011 | Falk | ................... | A61C 13/0001 433/173 |
| 8,628,327 B1 * | 1/2014 | Blaisdell | .............. | A61C 8/0001 433/213 |
| 9,572,640 B2 * | 2/2017 | Blaisdell | .............. | A61C 8/0001 |
| 9,895,209 B2 * | 2/2018 | Blaisdell | ................ | A61C 13/34 |
| 2002/0106610 A1 * | 8/2002 | Hurson | ................ | A61C 8/0001 433/173 |
| 2003/0211445 A1 * | 11/2003 | Klardie | ................ | A61C 8/0001 433/173 |
| 2008/0176186 A1 * | 7/2008 | Schaub | ................ | A61C 8/0001 433/173 |
| 2011/0129798 A1 * | 6/2011 | Zucker | ................. | A61C 8/0001 433/173 |
| 2011/0200968 A1 * | 8/2011 | Laizure, Jr. | ............. | A61C 8/008 433/173 |
| 2012/0295223 A1 * | 11/2012 | Robb | ..................... | A61C 8/008 433/173 |
| 2013/0177872 A1 * | 7/2013 | Blaisdell | ................ | A61C 8/008 433/173 |
| 2014/0080095 A1 * | 3/2014 | Suttin | .................... | A61C 13/34 433/202.1 |
| 2014/0124969 A1 * | 5/2014 | Blaisdell | ............. | A61C 8/0001 264/19 |
| 2014/0193775 A1 * | 7/2014 | Hogan | ................. | A61C 8/0001 433/201.1 |
| 2014/0319713 A1 * | 10/2014 | Blaisdell | ................ | A61C 13/34 264/19 |
| 2015/0351877 A1 * | 12/2015 | Boehm | ................ | A61C 8/0054 433/173 |
| 2017/0007372 A1 * | 1/2017 | Blaisdell | ................ | A61C 13/20 |

OTHER PUBLICATIONS

Boynuegri et al. "Effect of different localizations of microgap on clinical parameters and inflammatory cytokines in peri-implant crevicular fluid: A prospective comparative study" Clinical Oral Investigations; 2012; 16 (2):pp. 353-361.

International Search Report and Written Opinion for PCT/GR2015/000029 filed Jun. 12, 2015 on behalf of Ioannis Vergoullis. dated Sep. 29, 2015. 8 pages.

International Preliminary Report on Patentability for PCT/GR2015/000029 filed Jun. 12, 2015 on behalf of Ioannis Vergoullis. dated Dec. 6, 2016. 67 pages.

Chu et al. "The dual-zone therapeutic concept of managing immediate implant placement and provisional restoration in anterior extraction sockets" Compendium of Continuing Education in Dentistry; Aug. 2012; vol. 33, No. 7; pp. 524-534.

Chu et al. "Managing esthetic challenges with anterior implants. Part 1: midfacial recession defects from etiology to resolution" Compendium of Continuing Education in Dentistry; Aug. 2012; vol. 34, Special Issue 7; pp. 26-31.

* cited by examiner

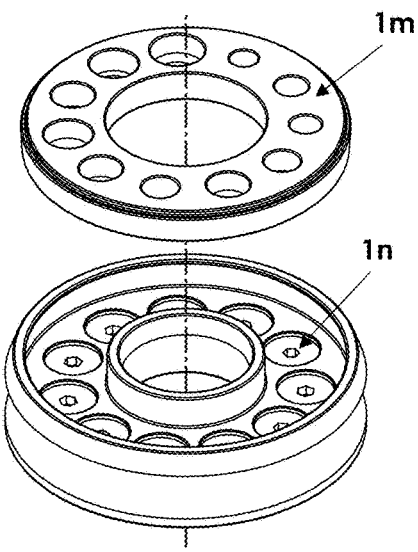
FIG. 1A
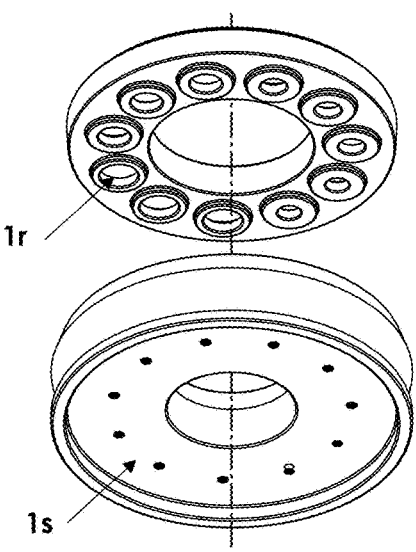
FIG. 1B
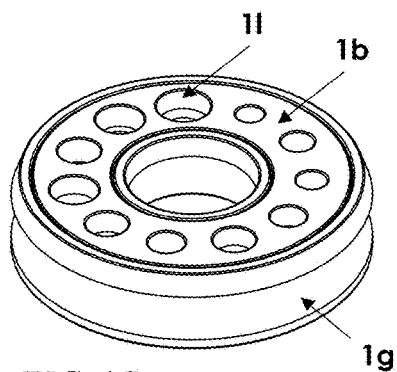
FIG. 1C
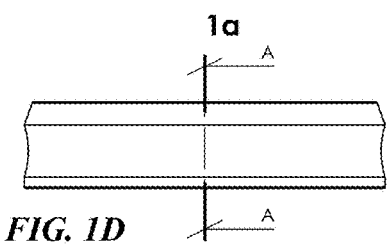
FIG. 1D
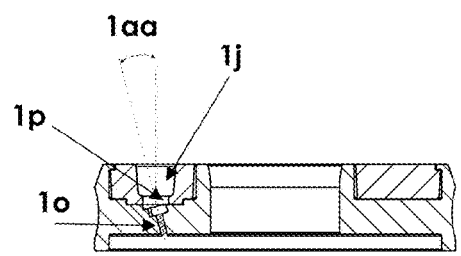
FIG. 1E   Τομή A-A

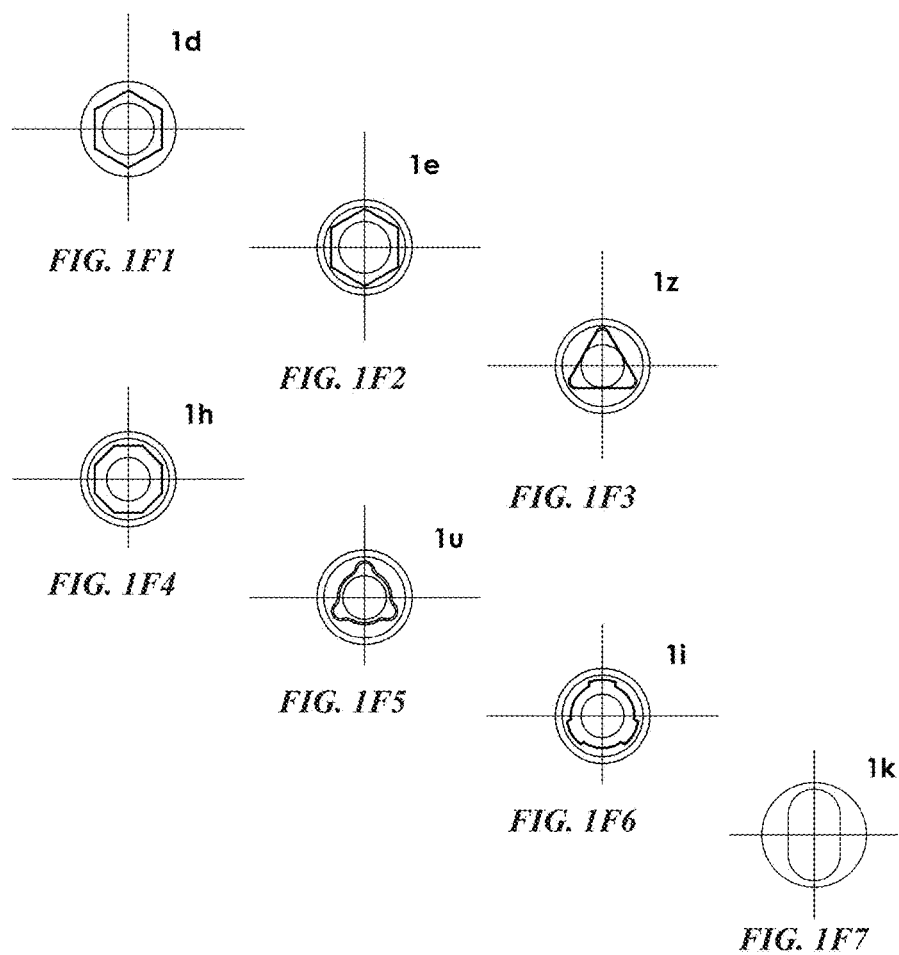
FIG. 1F1
FIG. 1F2
FIG. 1F3
FIG. 1F4
FIG. 1F5
FIG. 1F6
FIG. 1F7

Section A-A

Section A-A

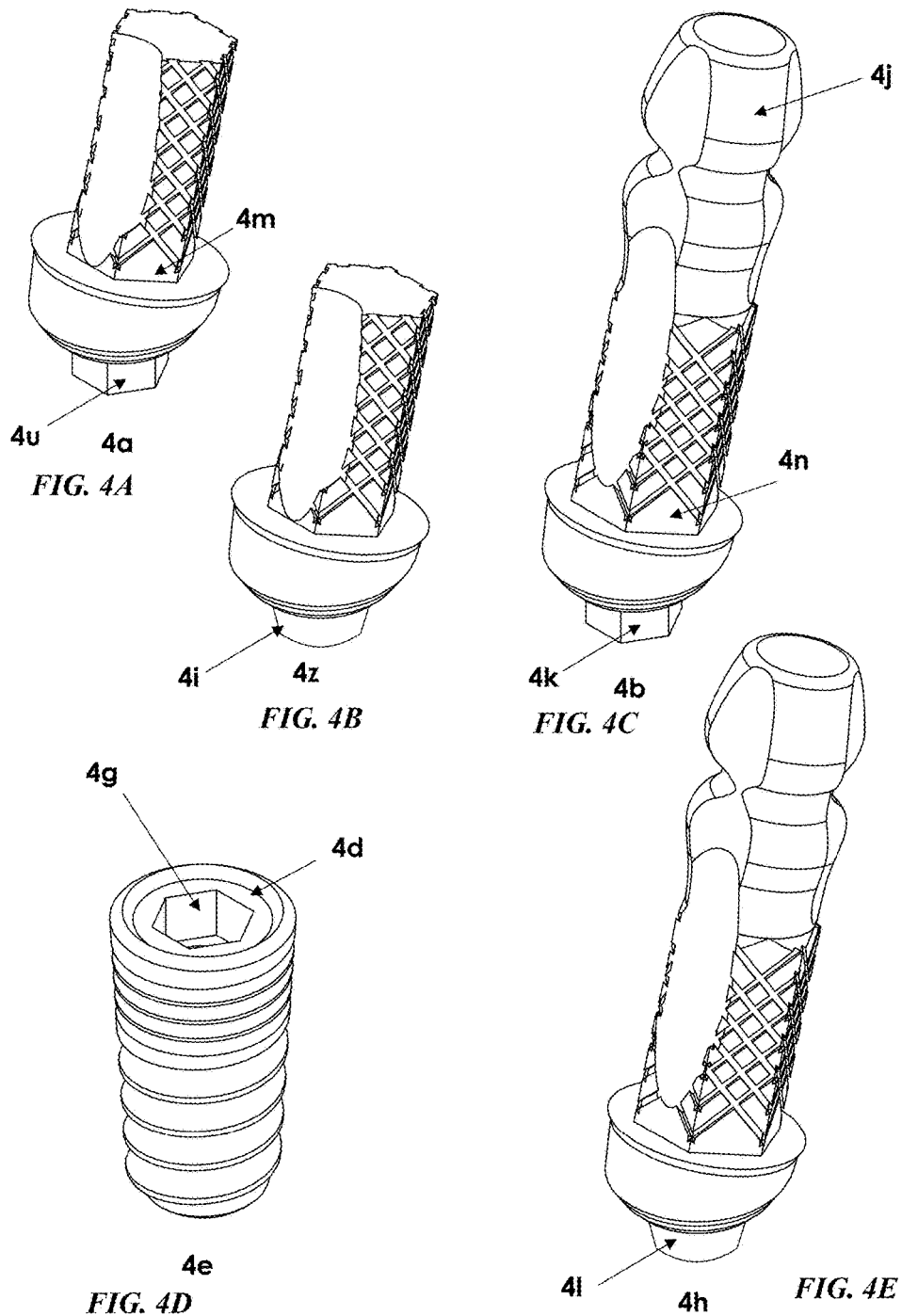

5a  5b 5g  5d

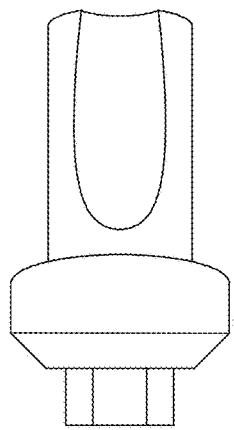
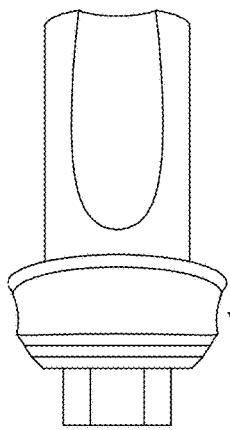
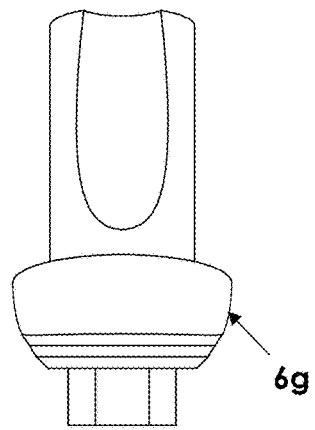
FIG. 6A        FIG. 6B        FIG. 6C
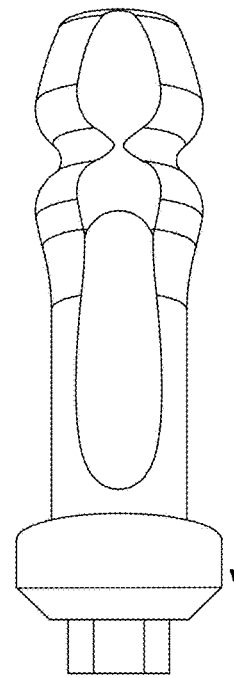
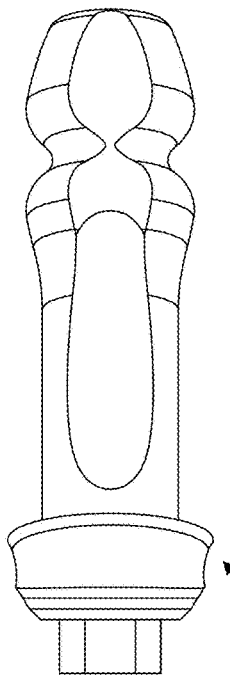
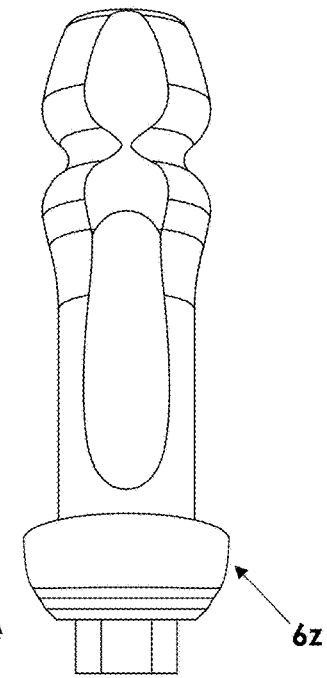
FIG. 6D        FIG. 6E        FIG. 6F

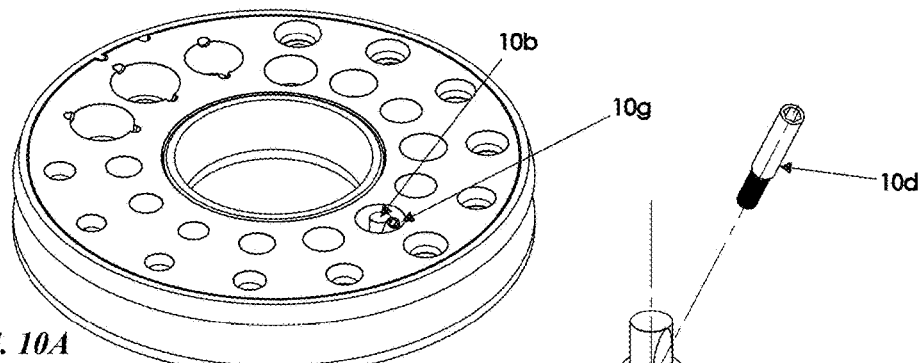
FIG. 10A
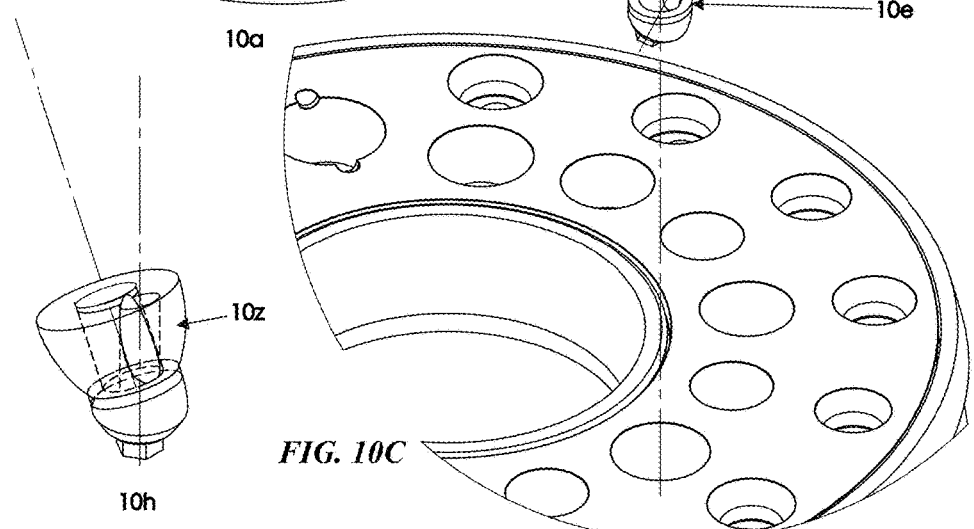
FIG. 10B  FIG. 10C
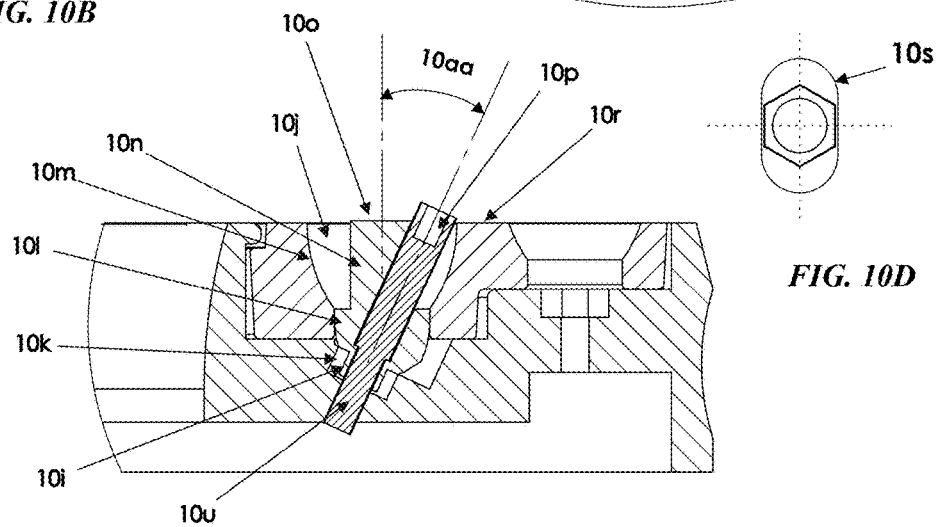
FIG. 10D
FIG. 10E

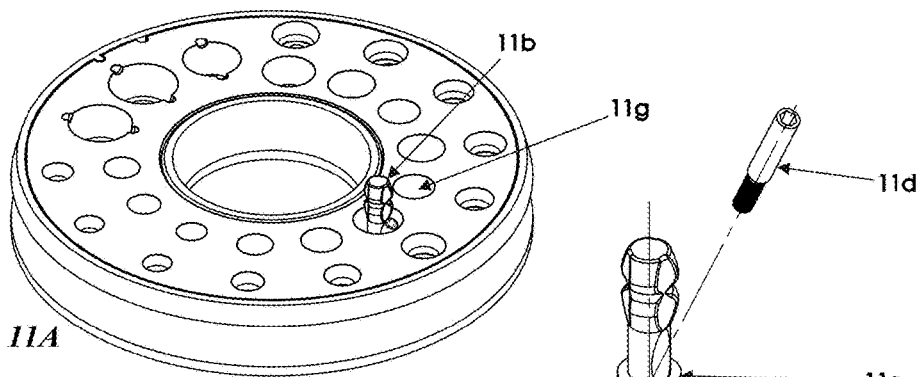
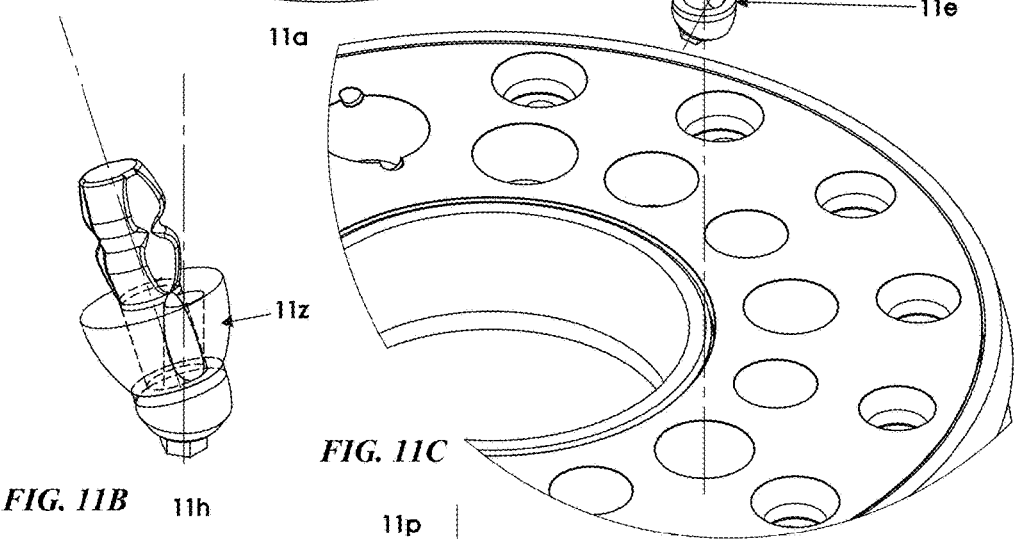
FIG. 11A
FIG. 11B
FIG. 11C
FIG. 11D
FIG. 11E

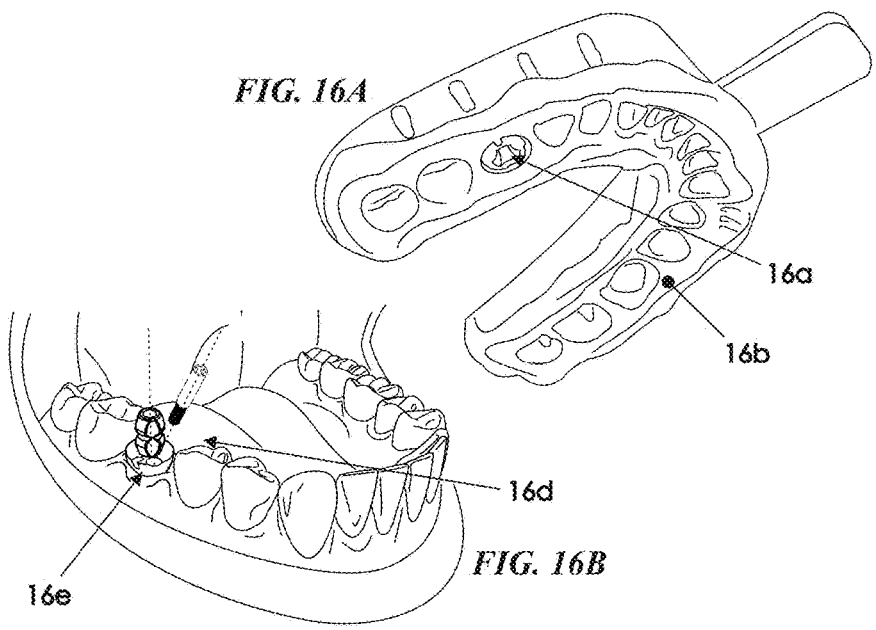
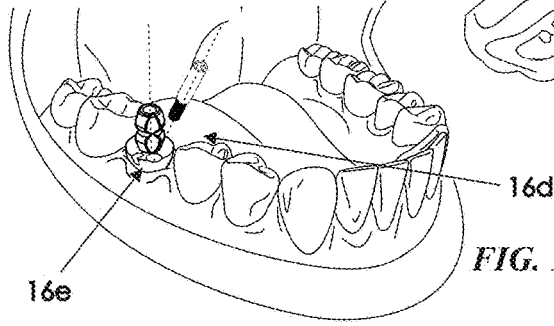
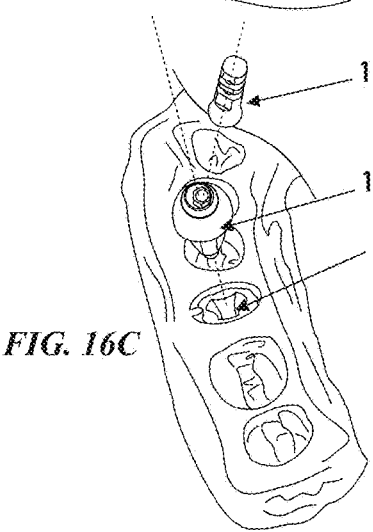
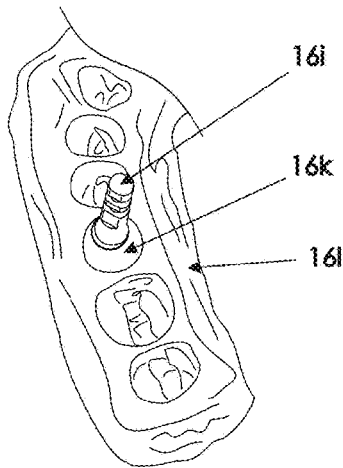
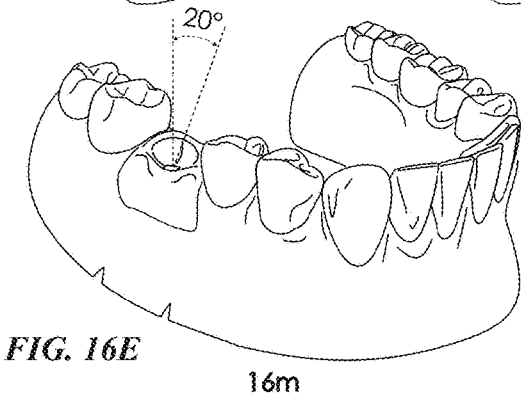

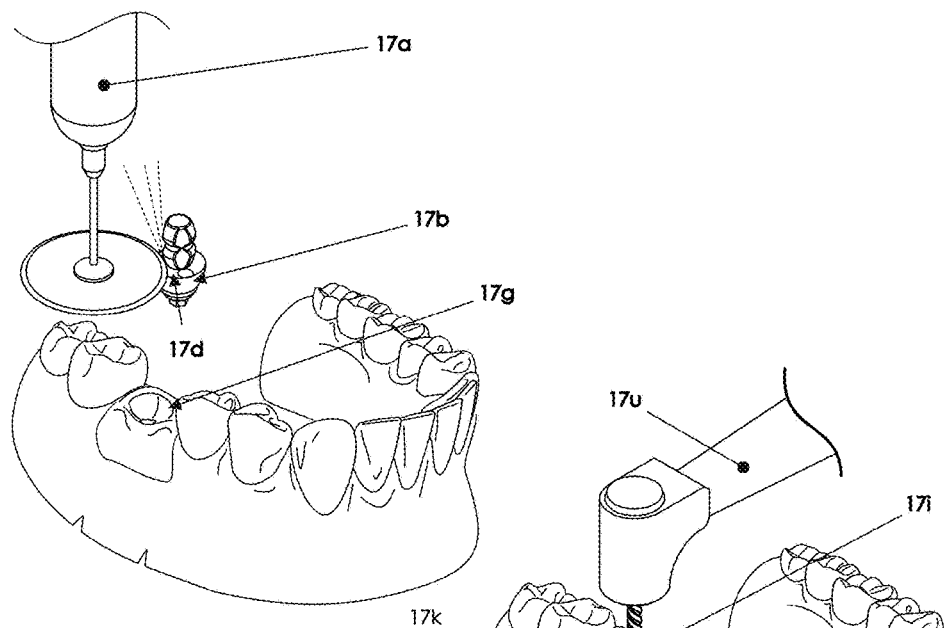
*FIG. 17A*
*FIG. 17B*
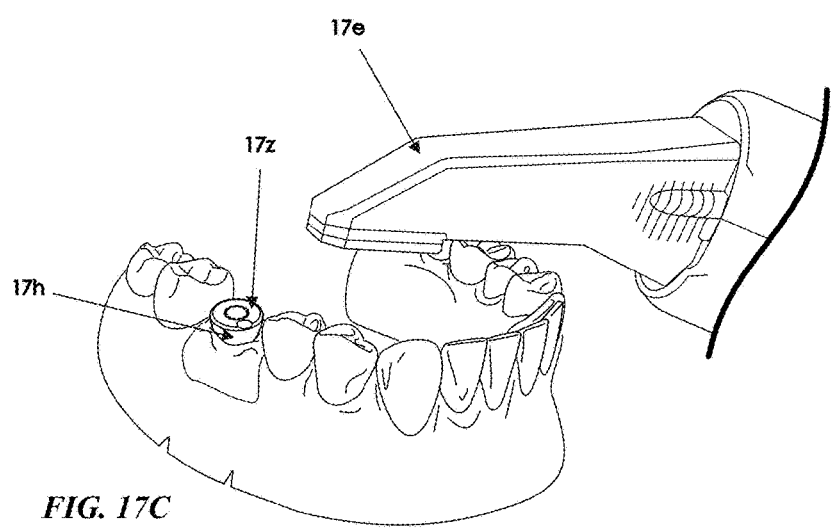
*FIG. 17C*

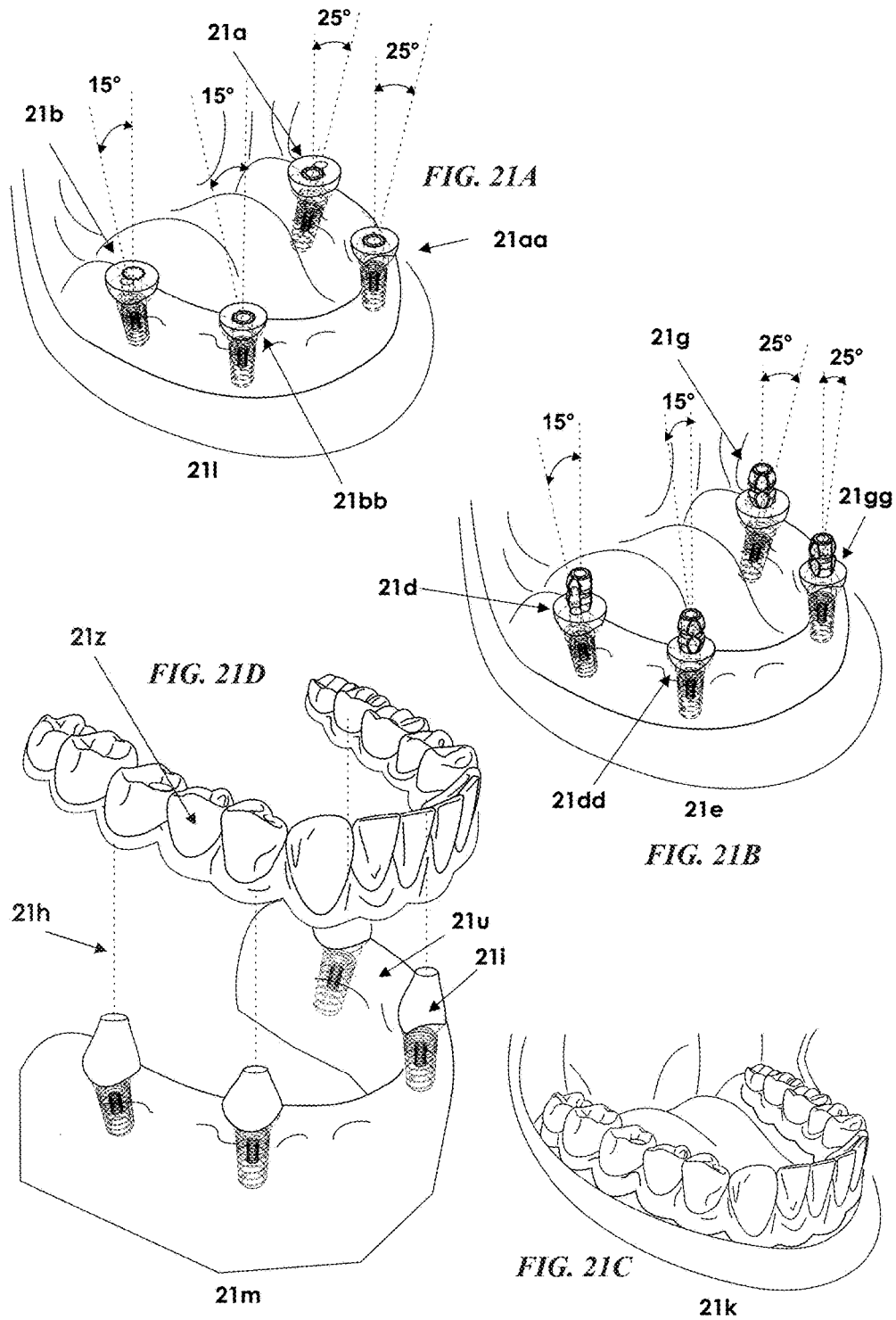

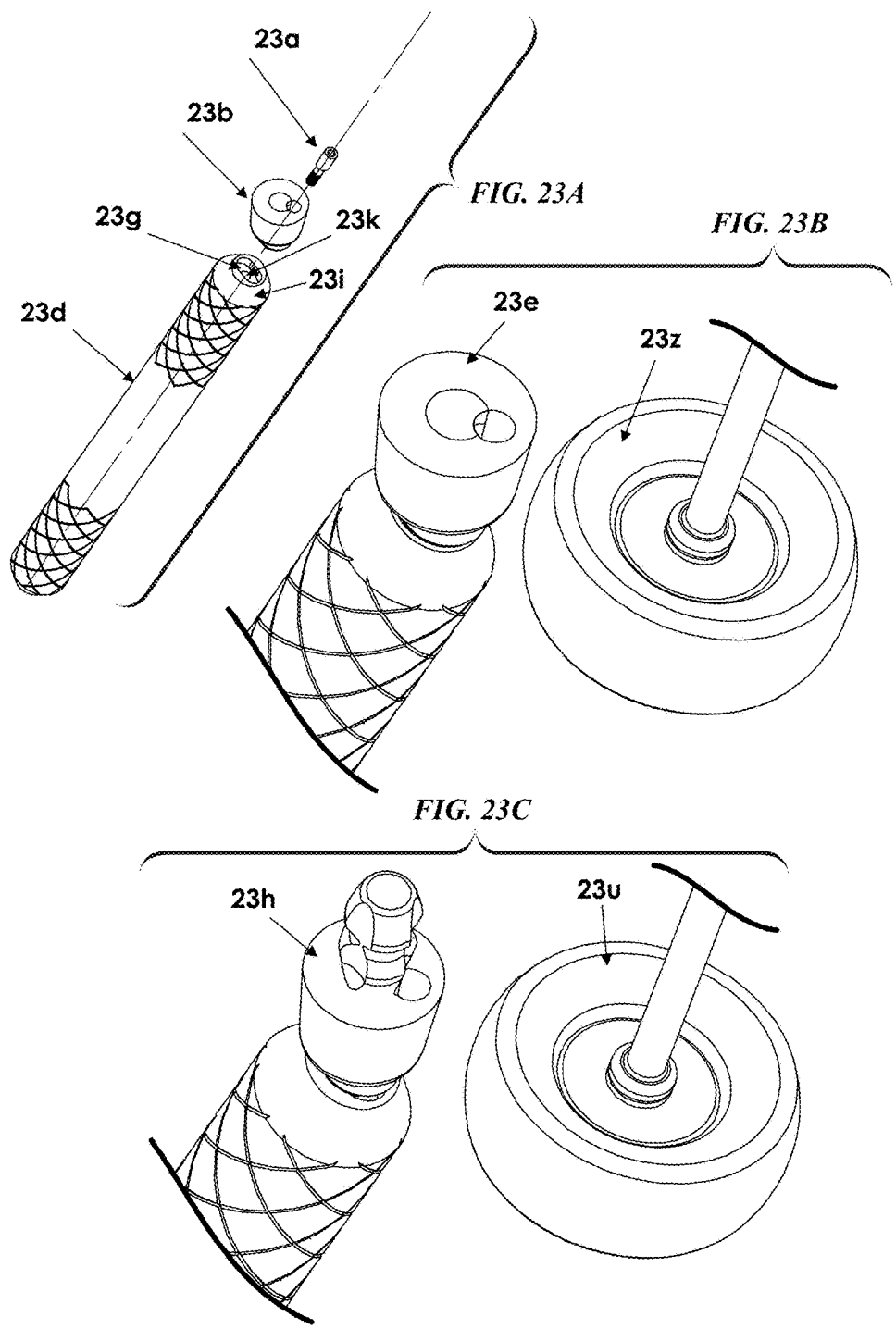

25a

25b

25g

25d

25e

25z

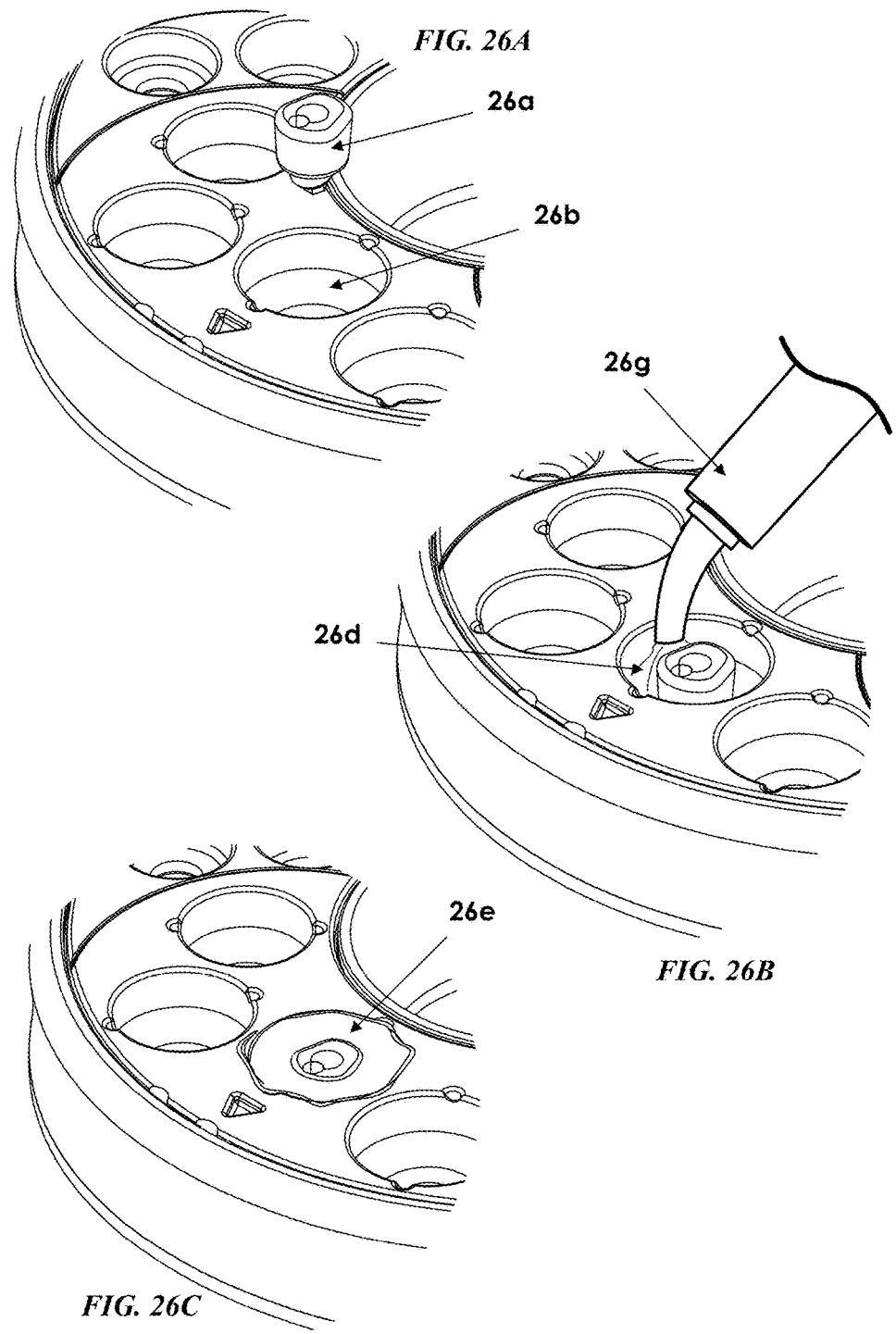

29a

29b

29g

29d

29e

29z

29h

29u

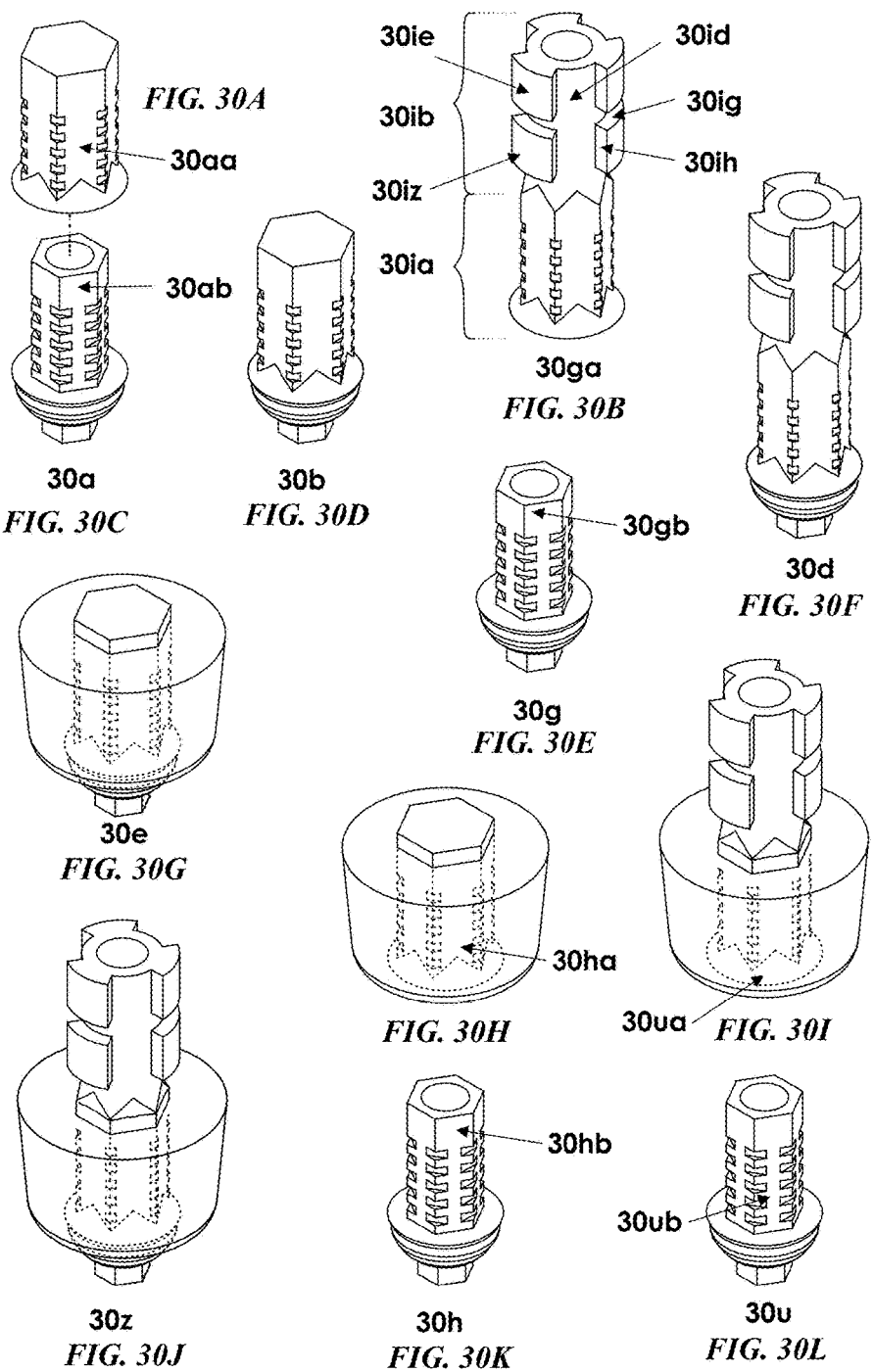

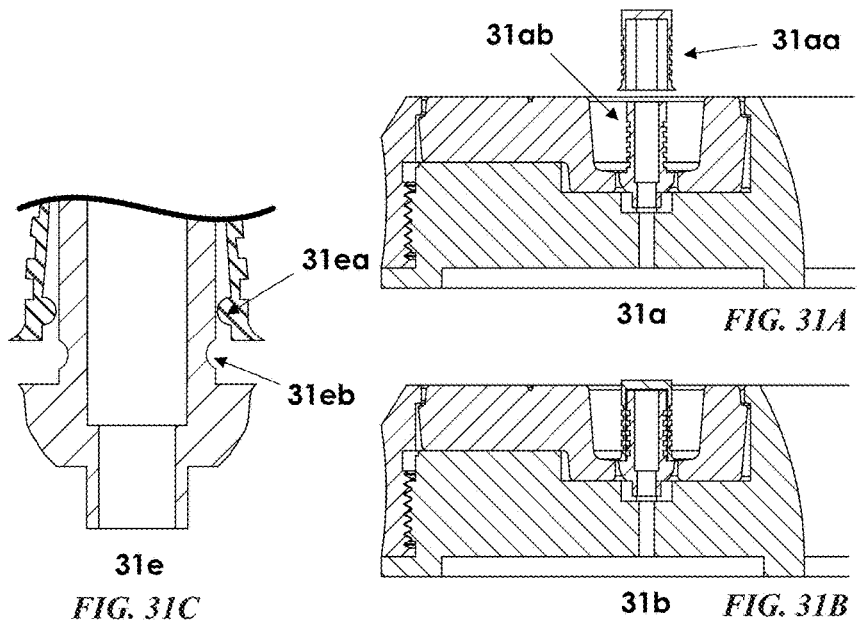
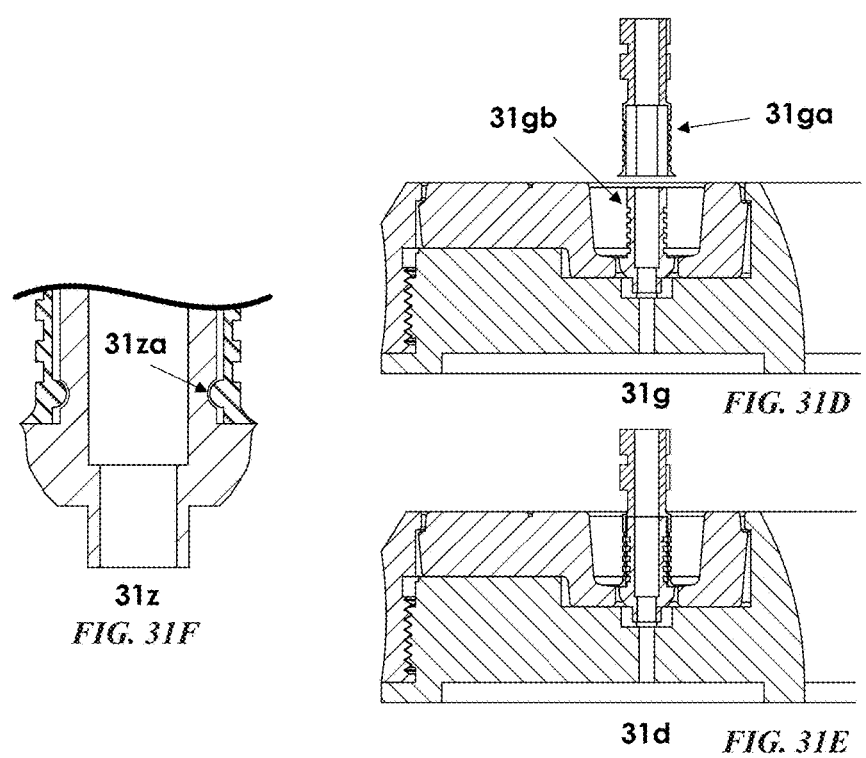

MOLDS FOR CUSTOM DENTAL IMPLANT ABUTMENTS AND IMPRESSION POSTS

CROSS-REFERENCE TO RELATED APPLICATIONS

The present application is the U.S. national stage of International Patent Application PCT/GR2015/000029 filed on Jun. 12, 2015. International Patent Application PCT/GR2015/000029 claims the benefit and is a continuation-in-part of Greek Patent Application Serial Nos. 20140100327 filed Jun. 13, 2014, 20140100642 filed Dec. 16, 2014, 20150100090 filed Mar. 4, 2015, and 20150100111 filed Mar. 12, 2015, which are each incorporated by reference herein in their entirety.

TECHNICAL FIELD

This invention is directed to molds and methods of using molds for the fabrication of custom, intra-orally and extra-orally modifiable, abutments and impression posts that can be used in the surgical and prosthetic stage of dental implant treatment and the use of such abutments and impression posts in dental implant related procedures.

BACKGROUND

The replacement of missing and hopeless teeth with dental implants is a very common practice. Once an implant is surgically placed, it is usually allowed to heal for a time frame of a few weeks in order for the process of its osseointegration with the jaw to be completed, before it can receive its final prosthesis. A part known as a healing abutment is coupled with the implant immediately after the latter is placed in the jaw, or at a later stage after the osseointegration process has been completed, in order to protect the prosthetic connection of the implant from the invasion of soft and/or hard tissue. This ensures the accessibility of the prosthetic connection of the implant after osseointegration is complete and it is desired to carry out the process of the prosthetic rehabilitation of the implant. Thus, after the completion of osseointegration, a process that may take from one to nine months, the healing abutment is disconnected from the implant and an impression post replaces it in order to proceed with the impression stage of the implant. Following the impression stage, the healing abutment is reconnected with the implant and finally it is replaced by the final dental implant prosthesis, which is supported by the implant that is anchored in the jaw. The existing healing abutments and impression posts on the market, along with the methodology involved in their use in the different stages of implant treatment, present a lot of shortcomings. Furthermore, the existing healing abutments and impression posts provided to the dentist by the different implant supply companies are prefabricated and it would be a great advantage if the dentist was be able to fabricate their own custom abutments and impression posts with improved characteristics using the molds of our invention.

Thus, before the invention described herein, dentists faced a significant problem arising from the limitations in choice of shape, size and material of fabrication of the healing abutments and impression posts that are provided by the different implant companies.

It is a common practice among dentists to use dental implants and parts from more than one implant company, which often have available healing abutments and impression posts of different dimensions and shapes. The mismatch between the parts supplied by the different implant companies forces the dentists to change their utilized protocols of treatment between different clinical cases, depending on the company that supplied the utilized implant.

The healing abutments available on the market with their relatively narrow cylindrical shape generate a narrow gingival emergence profile and this creates difficulties at the stage of the final implant prosthesis installment onto the implant, due to the difference in shape and dimensions between the gingival emergence profile and the emergence profile of the final prosthesis. The consequence of the above is that during prosthesis installment the latter pinches and traumatizes the soft tissue causing bleeding in the area and pain to the patient making necessary the use of local anesthesia.

The healing abutments available from most of the implant supply companies are made out of titanium and modifications to them are not recommended, even when modification is necessary. Thus, the use of large size healing abutments in many clinical cases is impossible because their body will interfere with the adjacent teeth making their installation onto the implant without any modifications of their size and shape difficult to impossible.

Before this invention, in order for a dentist to overcome the problem of a narrow gingival emergence profile developed from the healing abutments available in the market, it was necessary on the dentist's behalf to use a time and money consuming process for both the dentist and the patient. Specifically, the dentist utilizes sequentially new temporary prostheses expanding laterally the volume of the sub-gingival portion of the temporary prostheses gradually, in order to expand the gingival emergence profile. This is a process that can take anywhere between a few weeks to a few months until it is successfully completed.

In a small scale today there are healing abutments that can be scanned by a digital scanner in order for a digital impression to be fabricated. The disadvantage of these healing abutments is that they are not customizable and thus they fail to generate a three dimensionally ideal shape gingival emergence profile in all clinical cases. This does not allow the dentist to take full advantage of the tools that digital dentistry through CAD-Cam machinery potentially provides to the dentist.

Another important clinical problem is the accurate recording and transfer of the gingival emergence profile at the impression stage, from the mouth to the working cast, where the lab technician will fabricate the final implant prosthesis. The impression posts available from the different implant companies have a narrow emergence profile that corresponds to the narrow emergence profile of the healing abutments they provide and do not have properties that allow their ready customization. A dentist that has created a custom emergence profile through the use of a temporary prosthesis finds a difficult situation as to the way that they can record and transfer accurately the created custom gingival emergence profile from the mouth to the working cast, due to the difference in shape and dimensions of the latter as compared to the shape and the dimensions of the impression posts available to the dentist from the implant supply companies.

The impression posts that are commercially available are straight. Angulated impression posts are not available in the market. Thus, in clinical cases where the implant is located in the jaw with angulations different than the ones of the adjacent teeth, the dentist might not be able to install onto the implant a straight impression post as its body may interfere with the crowns of the adjacent teeth or the impression posts of the adjacent implants. Moreover, at the stage of impression removal from the mouth the different angulations of the aforementioned elements might lead to the development of areas of deformation of the impression material around the impression post, a fact that negatively affects the precision of the impression.

The impression posts available today also do not have the design and properties that allow their ready modification to temporary abutments that can be used to support a temporary prosthesis.

There is a patent application (US 20140124969) that concerns a jig that is utilized for the fabrication of straight asymmetrical custom healing abutments. That patent application concerns a jig that the application says can fabricate straight, custom, asymmetrical healing abutments with irregular surfaces. There is no claim for the utilization of this jig for the fabrication of, in addition to the straight healing abutments, angulated healing abutments and straight or angulated impression posts.

U.S. Pat. No. 8,628,327B1 describes the use of a mold with wells and abutments. However, wells and abutments in that patent have at least one asymmetrical cross-section and irregular surfaces to accommodate the introduction of additional biomaterial in order to apply that patent's method of addressing the void where a tooth is or was extracted. This asymmetrical cross-section surface limits the abutment to fitting in only one functional position on the implant as opposed to the use of a symmetrical cross-section that permits the positioning in many different orientations. In addition, a patient's soft tissue will not adapt as well to the irregular surfaces as it would to a regular surface. The use of the additional biomaterial by U.S. Pat. No. 8,628,327B1 that is added to the well to make the abutment, and which expands in close relationship to its prosthetic platform, also detracts from the usefulness of this patent's method because it does not generate and establish a better zone of connective tissue attachment and adhesion and provide for the presence of a micro-gap between the different materials in this sensitive biologically area as does a regular surface and a material such as polished titanium.

U.S. Pat. No. 8,628,327B1 also does not describe that its wells can be used to make impression posts that can be customized to correspond to a gingival emergence profile. In addition, if the wells of this patent were used to try to make an impression post, the impression post will not match the abutment because the patent teaches the use of the additional biomaterial to the abutment and thus the impression post made from the well will be different and the impression post cannot act as an exact replica that records and transfers the information into a working cast. U.S. Pat. No. 8,628,327B1 also does not describe a mold with wells that have two portions (upper and bottom) that can be used to make two-piece abutments and impression posts where their customized parts (a custom abutment cap and a custom impression abutment cap) are interchangeable on the abutment core. Thus, the patent does not teach that these parts can be interchangeably snapped onto the abutment core that is coupled to the implant, a feature that avoids the repetitive coupling and uncoupling that can induce harmful hard and soft tissue recession.

U.S. Pat. No. 8,628,327B1 also does not describe that its wells can be modified by the introduction of a curable elastomeric material to replicate the sub gingival portion of a dentist-modified abutment or implant prosthesis in order to accommodate the exact replication of this portion into an impression post.

U.S. Pat. No. 8,628,327B1 also does not teach a mold with wells that make abutments and impression posts that can be oriented in different angulations towards the vertical plane by angulation of the sockets comprising prosthetic connections of the abutments and impression posts. Instead, U.S. Pat. No. 8,628,327B1 suggests that the wells themselves should be aligned in different angulations toward the implant analogs located at the mold's base. Such a use of wells cannot achieve the advantages of applicant's invention for fit and precision of the resulting abutments and impression posts.

SUMMARY OF INVENTION

This invention is directed to molds and related methods for the fabrication of custom potentially modifiable intra-orally and extra-orally abutments and impression posts with various degrees of angulations (including straight or zero degrees of angulation) towards the vertical that can be utilized in the surgical and prosthetic stage of dental implant treatment. Such an angulated custom abutment can be utilized at the stage of surgical implant placement or later at the stage of implant uncovering, for the development of a custom shape gingival emergence profile around the platform of an implant that presents angulations different than the ones of the longitudinal axis of the final prosthesis that it will receive, or of the adjacent teeth or adjacent implants. These custom angulated abutments have a design and properties that allow them to be prepped intra-orally in the same manner as per natural teeth preparation and in this way they can be utilized after their proper modification as temporary abutments that can support a temporary prosthesis. The custom angulated, potentially modifiable impression posts can be utilized at the impression stage for the accurate recording and transfer of the location of the implant platform in the jaw, the orientation of the implant prosthetic connection and the developed gingival emergence profile around the implant platform from the mouth onto the working cast where the final implant prosthesis will be fabricated according to the aforementioned information. Both the custom potentially modifiable abutments and impression posts have properties that allow them to be scanned by a digital scanner for the generation of a digital impression that can be utilized for the digital fabrication of the final prosthesis with the use of CAD-Cam machinery.

Our invention relates to molds, to methodology involved, and to extra parts and materials that can be utilized either in a dental office or in a small scale manufacturing facility for the fabrication of custom potentially modifiable abutments and impression posts with various degrees of angulations that can be utilized in dental implant treatment.

The mold of our invention comprises a base preferably made out of metal (steel, titanium, aluminum, etc.) or ceramic material. Molds fabricated by the aforementioned materials present higher durability in the manner of time and frequency of use compared to molds fabricated exclusively by commonly used elastomeric materials.

The mold of our invention includes sockets of a geometrical shape that resemble prosthetic connections of different types and sizes. This way the use of independent implant analogs embedded in the mold is not required (these are required for the subject matter of US patent application 20140124969). The advantage of this characteristic of our mold is that it ensures the stable position of the prosthetic connection in the mold in contrast to a structure that receives implant analogs within its base where the right or wrong placement of the latter along with their stability in their final position might affect the effectiveness of its use. Furthermore, this characteristic reduces significantly the cost of production for the mold.

The mold of our invention has a superstructure as a continuation of the aforementioned base. The superstructure is preferably made out of metal, or ceramic, or acrylic, or elastomeric material. This superstructure has open wells with specific emergence shapes that comprise two parts integrated as one piece. The first part of the well of the superstructure that is in continuation with the prosthetic connection of the base of the mold represents the negative replication of the shoulder of a titanium abutment and impression post that comprises the core of the custom abutment and custom impression post, respectively. The specific design does not allow the invasion of the curable (i.e., curable or settable) biocompatible material further than the top border of the shoulder, preventing its approximation with the implant platform and the possibility of its micro invasion in the prosthetic connection of the base of the mold. This type of micro invasion could initiate problems in the appropriate assembly of the prosthetic connection of the abutment and of the impression post with the prosthetic connection of the implant in the mouth.

The second part of the well of the superstructure comprises a continuation of the first part and has an oval shape gradually expandable laterally towards the proximal end, with regular surfaces and symmetrical sections. The symmetrical design of the well allows the fabrication of custom abutments with an oval, symmetrical shape suitable for use in a vast variety of clinical cases without any limitations regarding the tooth type, or the implant position in the mouth, etc.

The dentist can fabricate through the use of the mold custom potentially modifiable abutments and impression posts according to the needs of the dentist's clinical practice.

When practicing the invention, a large variety of abutments and impression posts in various sizes will be available to the dentist, thereby overcoming the problem the dentist is facing today with the limitations in choice of available healing abutments and impression posts from the different implant companies.

By using the inventive mold, the dentist can fabricate custom abutments and impression posts that allow the dentist to apply the same treatment protocols for all of the dentist's clinical cases irrespective of the existing mismatches of the aforementioned parts provided by the different implant companies the dentist may be collaborating with in the dentist's clinic.

The custom abutments of our invention are comprised of three parts. The first part (prosthetic connection) ensures the exact and stable fit and retention of the abutment into the implant. The second part comprises a titanium shoulder with a polished, or lightly abraded at a microscopic level, regular surface. The third part comprises of a curable, biocompatible material with a regular surface and the ability to be highly polished. The advantage of the aforementioned characteristics of the custom abutments of our invention, in contrast to the irregular surfaces of the custom healing abutments described in the US patent application 20140124969, is that scientific research has shown that highly polished and regular surfaces of biocompatible materials, like titanium, composites, or acrylic resin, allow the attachment of the soft tissue to their surface, improving the final esthetic and biological outcome of the treatment (Chu S J, et al. The dual-zone therapeutic concept of managing immediate implant placement and provisional restoration in anterior extraction sockets. Compend Contin Educ Dent. 2012 July-August; 33(7):524-32, 534; Chu S J, Tarnow D P. Managing esthetic challenges with anterior implants. Part 1: mid-facial recession defects from etiology to resolution. Compend Contin Educ Dent. 2013 October; 34 Spec No 7:26-31).

Also, the second part of the custom abutment of our invention with the highly polished titanium surface allows the preservation of a zone of connective tissue attachment, known as the biologic zone, that protects the underlying hard tissue (Albrektsson T, Jansson T, Lekholm U. Osseointegrated dental implants. DentClin North Am. 1986 January; 30(1):151-74.). Moreover, the shoulder ensures that the curable biocompatible material that is connected with the titanium cylinder maintains a distance from the implant platform and the surrounding hard tissue equal to the height of the abutment shoulder. This distance ensures the appropriate displacement of the micro gap present between the two different surfaces (top border of the shoulder and bottom border of curable biocompatible material) from the peri-implant hard tissue (Boynuegri A D, et al. Effect of different localizations of micro-gap on clinical parameters and inflammatory cytokines in peri-implant crevicular fluid: a prospective comparative study. Clin Oral Investig. 2012 April; 16(2):353-61).

The custom abutments and impression posts of our invention can be prepped (abraded) following the same principles as per tooth preparation, aiming for the fabrication of a temporary prosthesis that can be cemented by use of cement or other bonding agents directly on to the modified abutment. This specific process comprises part of the every day clinical practice of the dentist and it is very simple to be performed. It also eliminates the need for repetitive connections and disconnections of the abutments on the implant level, which is a great advantage for the long-term stability of the peri-implant soft and hard tissues.

BRIEF DESCRIPTION OF THE DRAWINGS

FIG. 1A is a perspective view of components of an exemplary mold;

FIG. 1B is a perspective view of components of an exemplary mold;

FIG. 1C is a perspective view of an exemplary mold;

FIG. 1D is a side view of an exemplary mold;

FIG. 1E is a cross-sectional view of an exemplary mold;

FIGS. 1F1-1F7 are perspective views of the surface of exemplary prosthetic connections;

FIGS. 4A-4C and 4E are perspective views of exemplary impression posts;

FIG. 4D is a perspective view of an implant platform and prosthetic connection;

FIGS. 6A-6F are perspective views of exemplary impression posts;

FIG. 10A is a perspective view of an exemplary mold;

FIG. 10B is a perspective view of an exemplary abutment;

FIG. 10C is an exploded, perspective view of an exemplary mold, abutment and retention screw;

FIG. 10D is a perspective view of an exemplary prosthetic connection;

FIG. 10E is a cross-sectional, exploded view of an exemplary mold, abutment and retention screw;

FIG. 11A is a perspective view of an exemplary mold;

FIG. 11B is a perspective view of an exemplary impression post;

FIG. 11C is an exploded, perspective view of an exemplary mold, impression post and retention screw;

FIG. 11D is a perspective view of an exemplary prosthetic connection;

FIG. 11E is a cross-sectional, exploded view of an exemplary mold, impression post and retention screw;

FIGS. 16A-16E are exploded and perspective views of aspects of an exemplary process for installation of implants;

FIG. 17A is a perspective view of a step in an exemplary process for restoring an implant with a temporary prosthesis using abrasion;

FIG. 17B is a perspective view of a step in an exemplary process for restoring an implant with a temporary prosthesis by forming a temporary abutment;

FIG. 17C is a perspective view of step in an exemplary process for restoring an implant with a temporary prosthesis using digital scanning;

FIGS. 21A-21D are perspective views of an exemplary process for installing multiple implants;

FIG. 23A is a perspective view of an exemplary retention handle;

FIG. 23B is an exploded, perspective view of an exemplary retention handle, abutment and polisher;

FIG. 23C is an exploded, perspective view of an exemplary retention handle, impression post, and polisher;

FIGS. 26A-26C are exploded perspective views of aspects of an exemplary process using a mold to make a component useful in the installation of an implant;

FIGS. 30A-30L are perspective views of exemplary abutments and impression posts; and FIGS. 31A-31F are exploded cross-sectional views of an exemplary mold.

DESCRIPTION OF EMBODIMENTS

Figure 2A:
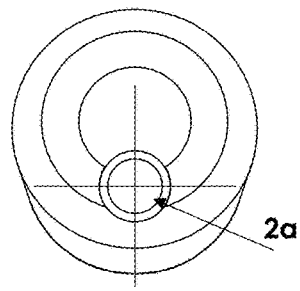
FIGS. 2A-2C are perspective views of exemplary abutments.
Figure 2B:
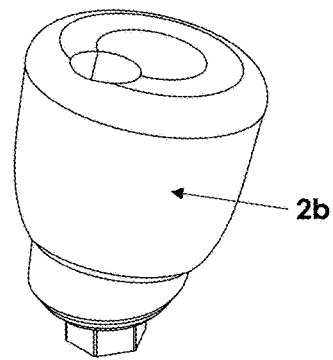
Figure 2C:
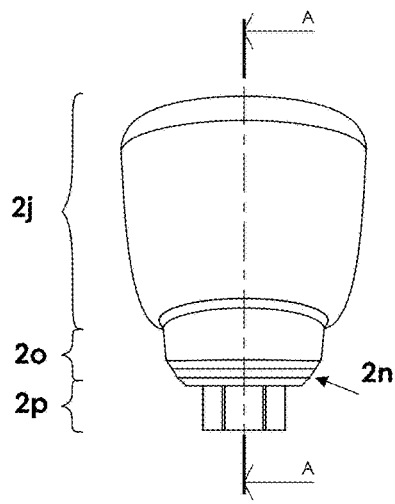
Figure 2D:
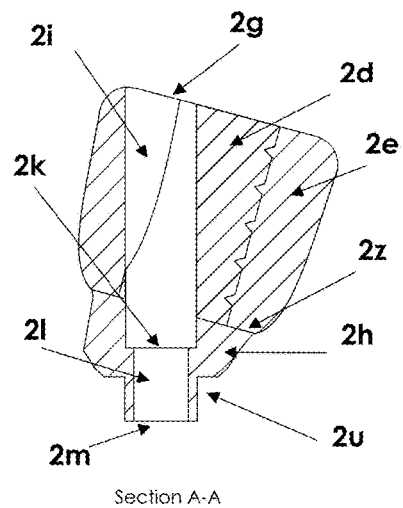
FIG. 2D is a cross-sectional view of an exemplary abutment.
Figure 3A:
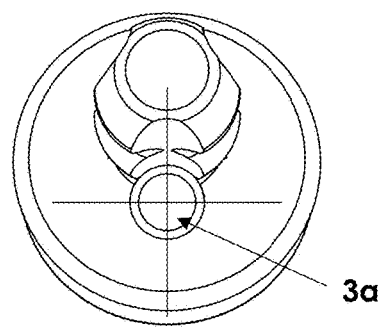
FIGS. 3A-3C are perspective views of exemplary impression posts.
Figure 3B:
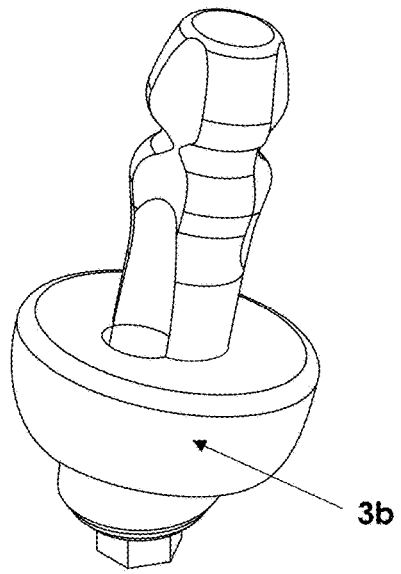
Figure 3C:
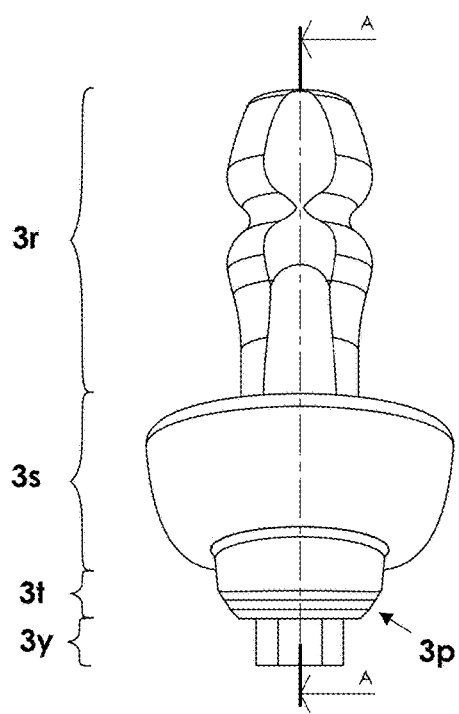
Figure 3D:
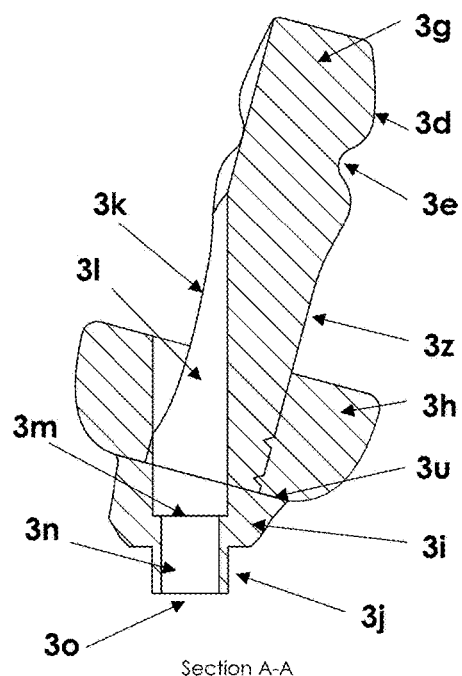
FIG. 3D is a cross-sectional view of an exemplary impression post.

Embodiments of the invention are described below with the assistance of examples and with reference to the accompanying drawings.

FIGS. 1A-1E and 22A-22B show exemplary molds (1a, 22a), which are used for the fabrication of custom and potentially modifiable abutments (FIGS. 2A-2D, 2.r) and custom, potentially modifiable impression posts (FIGS. 3A-3D, 3.f) with different degrees (including zero degrees) of angulations towards the vertical (1.aa). The molds (1.a, 22.a) are comprised of a base (1.g, 22.b) and a superstructure (1.m, 22.e).

The base of the mold (1.g, 22.b) is generally perpendicular towards the vertical (FIG. 1E, Section A-A, FIG. 24B) and it is preferably made out of metal (titanium, aluminum, stainless steel, etc.), or ceramic material, or plastic, or any other material that can achieve stable dimensions and a well-polished surface. This base (1.g, 22.b) has on its upper surface (22.e) one or more sockets of the same or different geometrical shape and dimensions (1.n, 22.z) that represent prosthetic implant connections of the same or different type and dimensions (4.g) which are oriented with different degrees of angulations (1.aa, 24.a) while its bottom surface is solid (1.s).

Figures 5A, 5B:
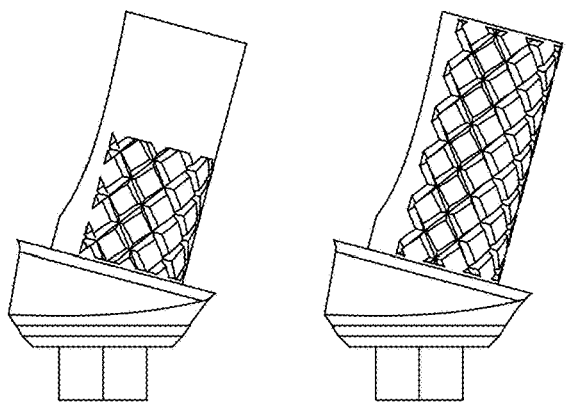
FIGS. 5A-5D are perspective views of exemplary abutments.
Figures 5C, 5D:
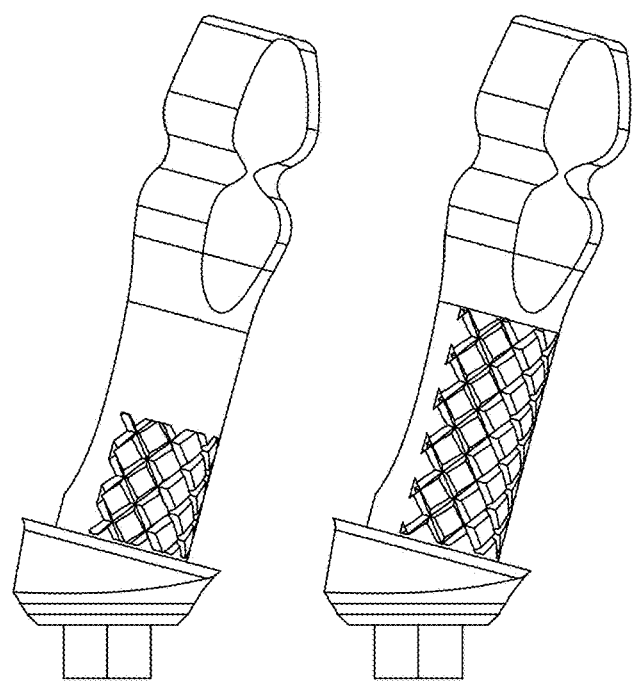
Figure 7A:
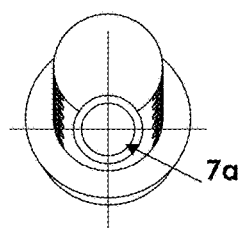
FIGS. 7A-7C are perspective views of exemplary abutments.
Figure 7B:
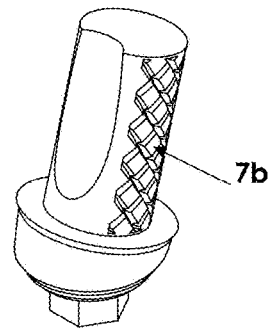
Figure 7C:
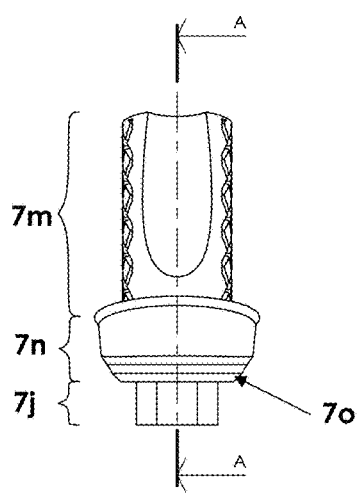
Figure 7D:
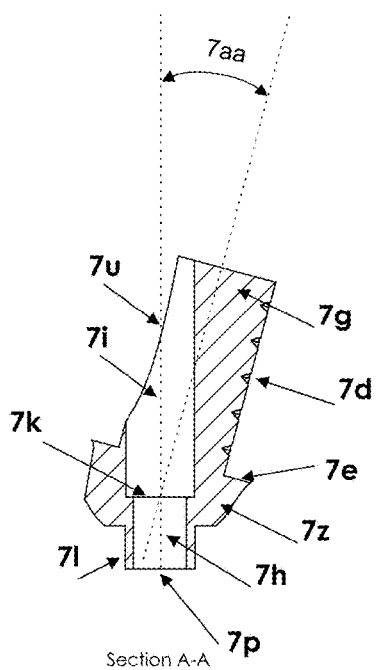
FIG. 7D is a cross-sectional view of an exemplary abutment.

The prosthetic connections (1.n, 22.z) of different types and sizes that will be used follow a design similar to those that are available on the market of implant prosthetic connections (FIG. 4D, 4.g) and present a geometrical shape that enables them to have anti-rotational properties (11.z, 10.z) while at the center or off center of their base they have a threaded blind bore (24.j) that couple threads with the thread of a long (9.e) or a short (9.a) retention screw (FIGS. 9A-B) of the angulated abutment (7.r) and or angulated impression posts (8.k). This retention screw (9.e, 9.a) allows the stable retention of the abutment (7.r) and or the impression post (8.k) onto the base. Thus, different types of prosthetic connections (1.n, 22.z, 22.n) may be used with anti-rotational properties like, for examples (FIGS. 1F1-1F7), external hexagon (1.d, FIG. 1F1), internal hexagon (1.e, FIG. 1F2), internal trilobe (1.z, FIG. 1F3), internal octagon (1.h, FIG. 1F4), conical connections (1.u, FIG. 1F5), cut slots (1.k, FIG. 1F7), circular with vertical grooves (1.i, FIG. 1F6), all of them with different degrees of bevel and depth.

Figure 24A:
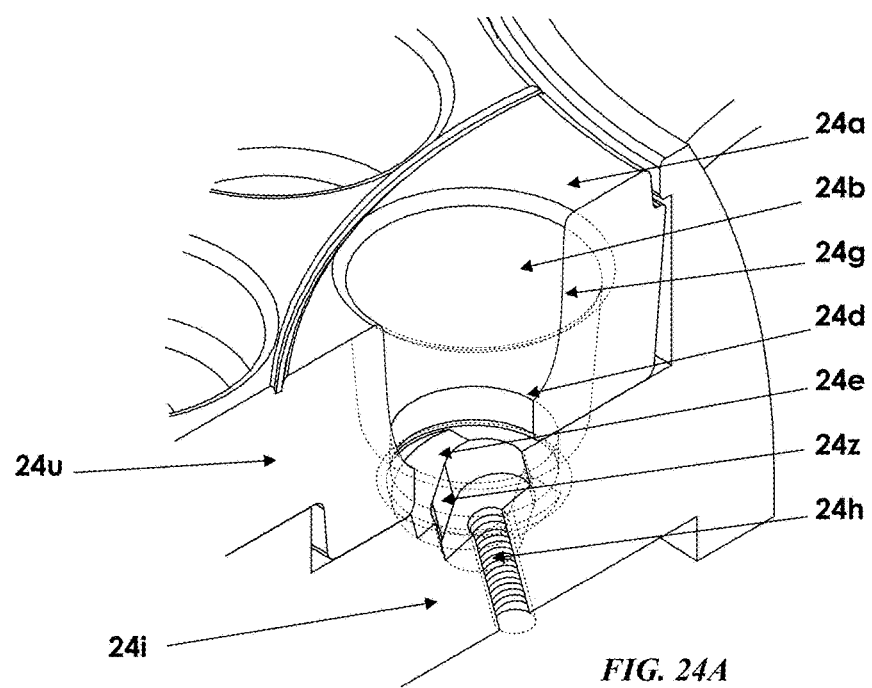
FIG. 24A is an exploded view of an exemplary mold.
Figure 24B:
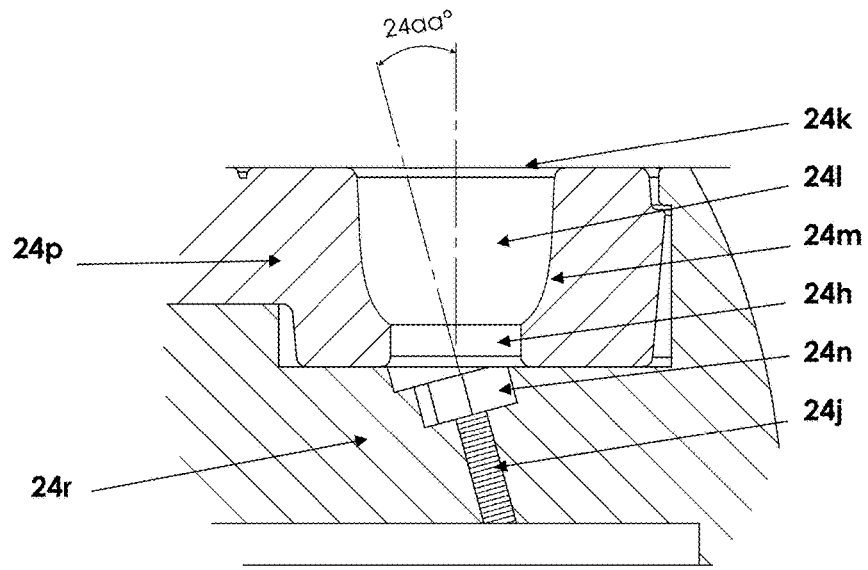
FIG. 24B is an cross-sectional view of an exploded portion of an exemplary mold.
Figure 25A:
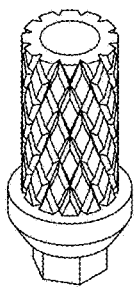
FIGS. 25A-25F are perspective views of exemplary abutments and impression posts.
Figure 25B:
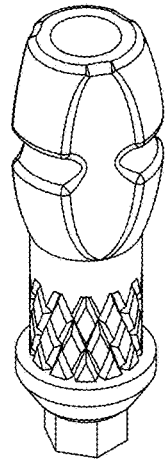
Figure 25C:
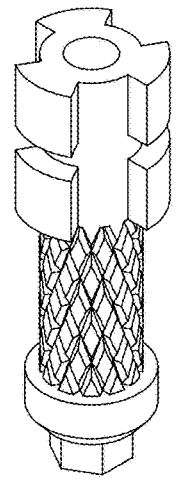
Figure 25D:
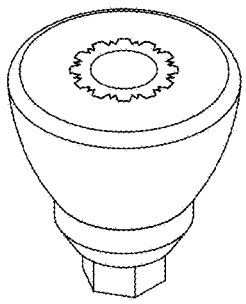
Figure 25E:
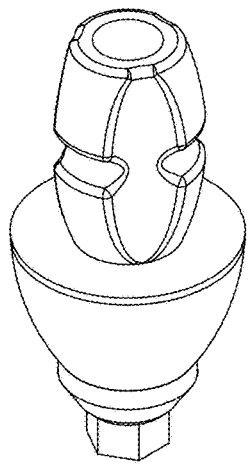
Figure 25F:
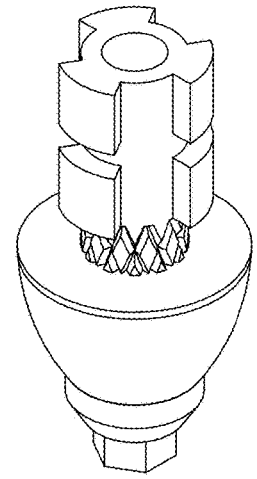
Figures 27A, 27B, 27C:
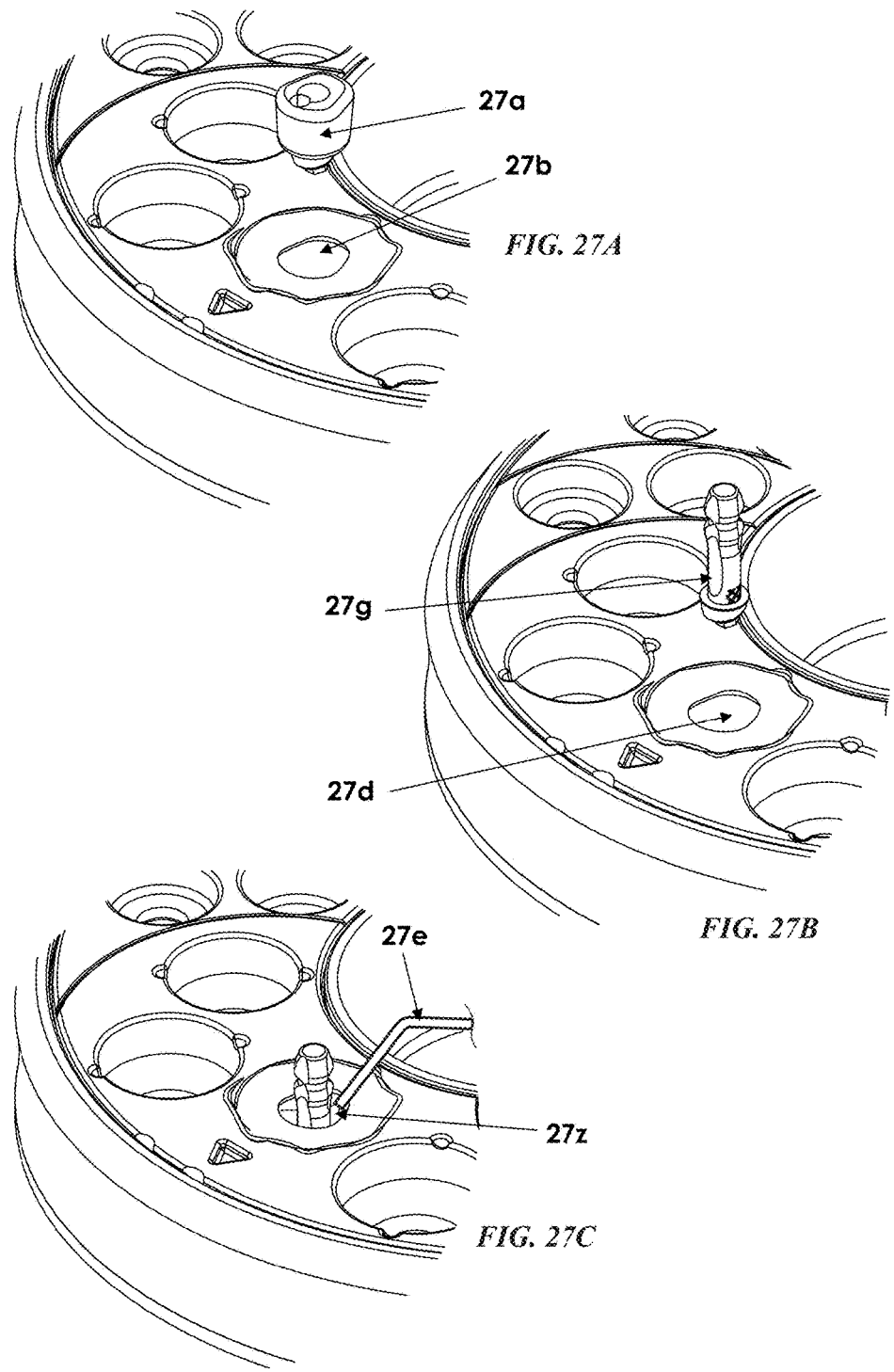
FIGS. 27A-27C are exploded perspective views of aspects of an exemplary process using a mold to make a component useful in the installation of an implant.
Figure 28A:
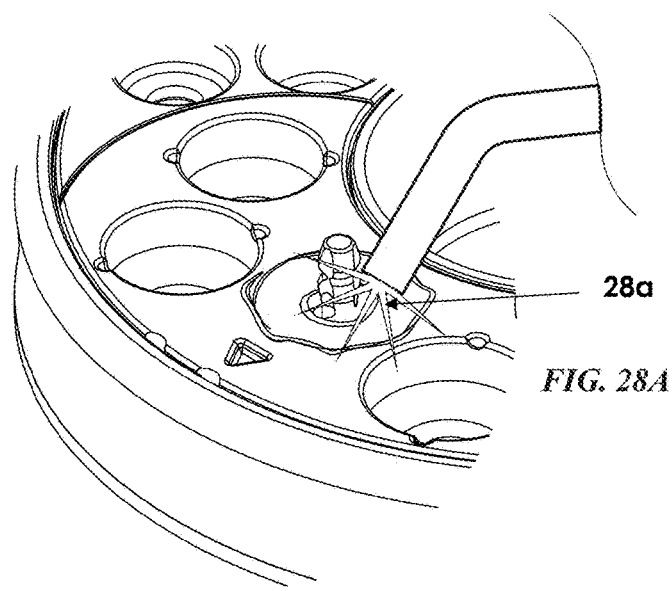
FIGS. 28A-28B are exploded perspective views of aspects of an exemplary process using a mold to make a component useful in the installation of an implant.
Figure 28B:
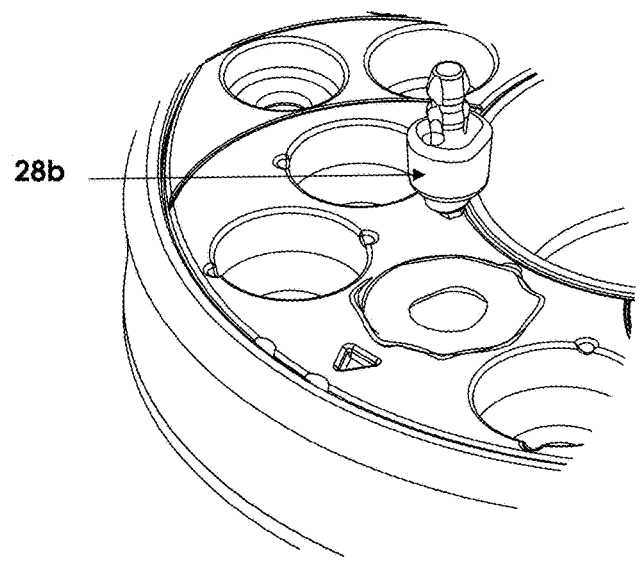
Figure 29A:
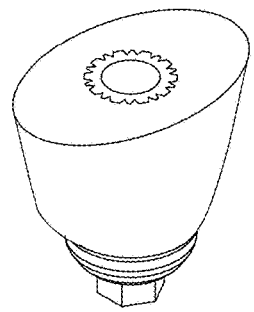
FIGS. 29A-29H are perspective views of exemplary abutments and impression posts.
Figure 29B:
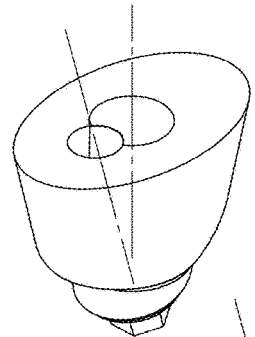
Figure 29C:
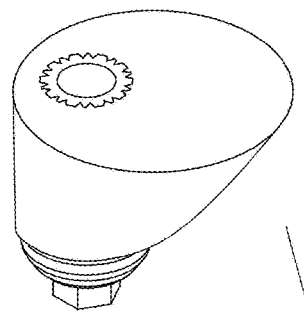
Figure 29D:
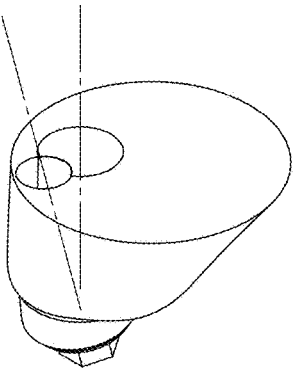
Figure 29E:
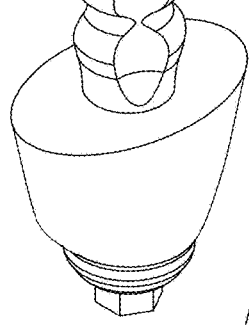
Figure 29F:
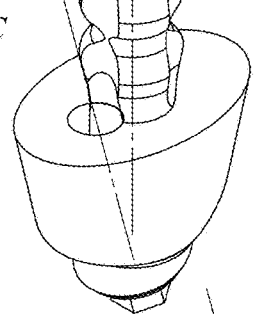
Figure 29G:
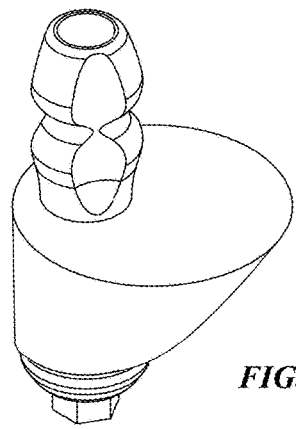
Figure 29H:
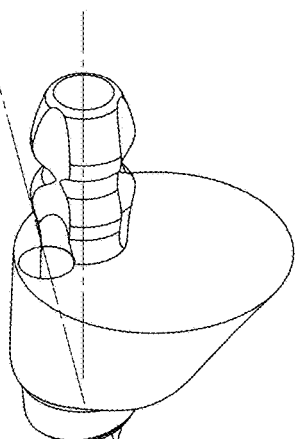

The diameters of the prosthetic connections may vary from about 2 mm to about 8 mm. The prosthetic connections (24.*n*) are oriented in the base of the mold (24.*r*) with angulations of their longitudinal axis and the blind threaded bore (24.*j*) towards the vertical that vary up to about 45 degrees (FIG. 24A, 24.*aa*).

FIGS. 1A-1E, 22A-22B and 24A-24B illustrate a superstructure (1.*m*, 22.*e*, 24.*p*) that is generally perpendicular towards the vertical and it is made out of an elastomeric material or metal or ceramic or acrylic or any other material that has or can acquire an appropriate and well polished surface. This superstructure (1.*m*, 22.*e*, 22.*p*) is connected to the base (1.*g*, 22.*b*, 24.*r*) with mechanical or chemical connection. This superstructure (1.*m*) could also be one piece with the base (1.*g*).

The superstructure (1.*m*, 22.*e*, 24.*p*) has open wells (1.*l*, 22.*g*, 24.*b*) with parallel orientation towards the vertical (24.*aa*) that to their distal end (meaning bottom end (1.*r*), towards the base of the mold (1.*g*, 24.*r*)) couples precisely the implant prosthetic connection of the base of the mold (1.*n*, 22.*z*, 24.*n*), while their proximal end (meaning top end (24.*k*)) is open. Every well (1.*l*, 22.*g*, 24.*b*) comprises of two parts as one piece. The first part (24.*h*) is towards the distal and is located in continuation of the implant prosthetic connection of the base (24.*n*) and it comprises the negative replication of the upper surface of the shoulder (7.*e*, 8.*s*) of an angulated and/or straight abutment (7.*r*, 25.*a*), and/or impression post (8.*k*, 25.*b*, 25.*g*) and it has a minimum diameter that is equal to the maximum diameter of their shoulder (7.*n*, 8.*p*). The second part (24.*l*) comprises a continuation of the first part (24.*h*) upwards, and comprises the negative replication of the custom body (2.*j*, 2.*e*, 3.*s*, 3.*h*) of the corresponding per case, custom potentially modifiable abutment (2.*r*, 25.*d*, 30.*e*) and impression post (3.*r*, 25.*e*, 25.*z*, 30.*z*), which corresponds to an emergence profile of oval or cylindrical shape, gradually expandable laterally, from the base upwards, and with symmetrical cross-section and regular surfaces (FIGS. 2A-2D, 3A-3D). The diameter of every well (1.*l*, 22.*g*) differs according to the type and size of the prosthetic connection of the base (1.*v*, 22.*z*) and the minimum diameter of the shoulder of the angulated abutment (7.*n*) and impression post (8.*p*). This does not exclude the possibility for prosthetic connections (1.*n*, 22.*z*, 24.*n*) of different dimensions to correspond with same size sockets (1.*l*, 22.*g*). The dimensions of the diameter of the two parts (1.*j*, 24.*l*, 24.*h*, 1.*p*) of every socket (1.*l*, 22.*g*) and of the different sockets to each other (1.*l*, 22.*g*) may vary from about 2.5 mm to about 14 mm. The dimensions of the sockets (1.*l*, 22.*g*) in height may vary from about 3 mm to about 15 mm. The aforementioned range of dimensions does not exclude the further expansion of this range if the future needs of implant therapy demand such expansion.

Figure 9A:
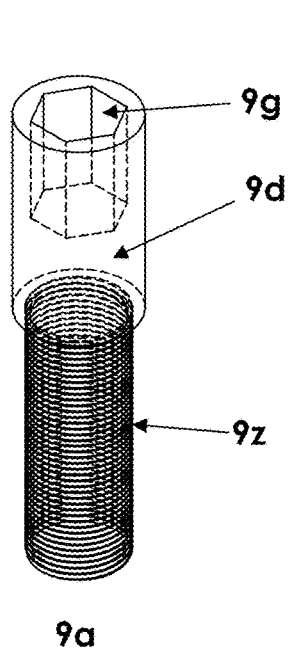
FIGS. 9A-9B are perspective views of exemplary retention screws.
Figure 9B:
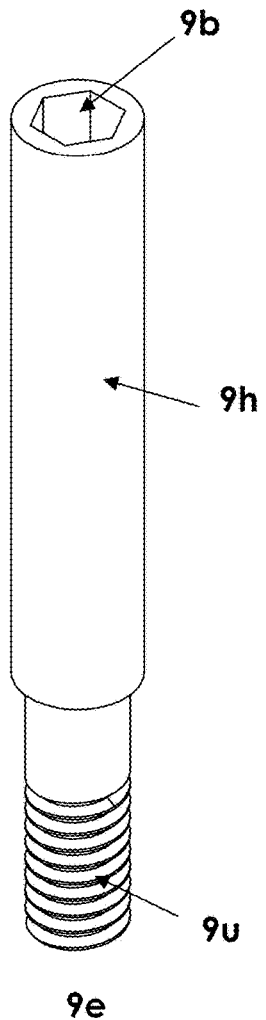
Figure 12A:
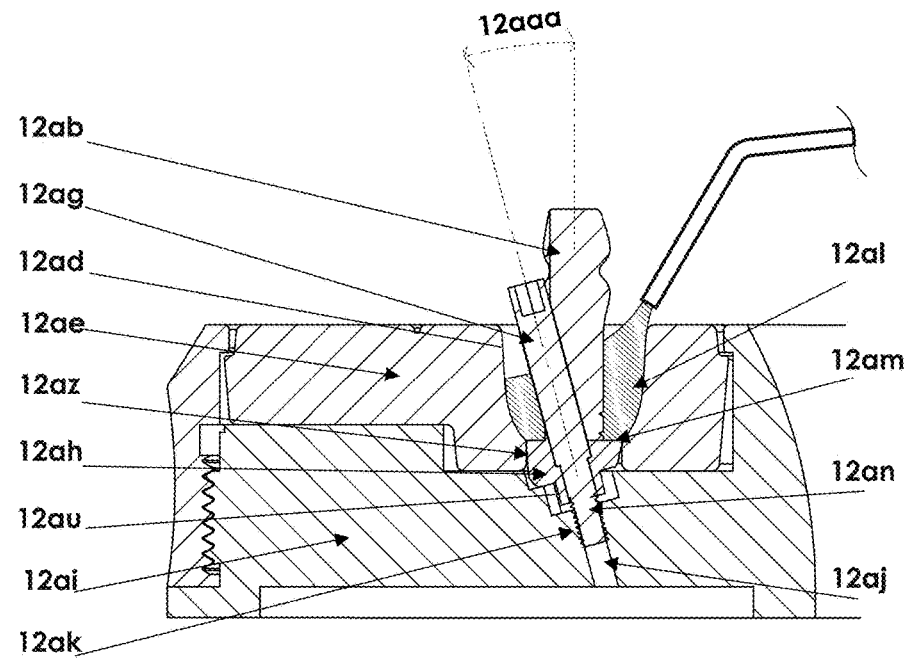
FIG. 12A is an exploded cross-sectional view of an exemplary mold.
Figure 12B:
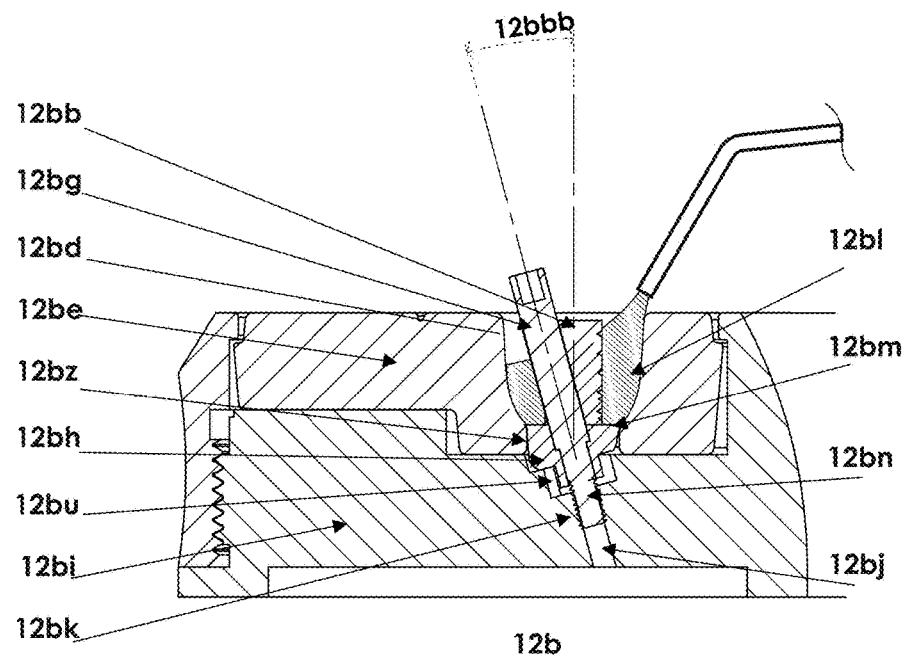
FIG. 12B is an exploded cross-sectional view of an exemplary mold.

FIGS. 9A-9B describe a long retention screw (9.*e*) of the angulated abutment (7.*r*) and impression post (8.*k*) with which (10.*u*, 11.*u*) the latter (10.*o*, 11.*p*) connect and retain to the prosthetic connection of the base (10.*k*, 11.*k*) of the mold (FIGS. 10A-10E, 11A-11E). The long retention screw (9.*e*) is preferably made out of metal, or plastic, or ceramic material and it is descriptively divided to its thread (9.*u*) and its head (9.*h*). The head (9.*h*) has a smooth surface and a diameter that is larger than the one of the thread (9.*u*) while at the top end it has an internal socket of geometrical shape (9.*b*) that is a polyhedron or conical and it is the negative representation of the tip of a screwdriver with corresponding geometrical shape and dimensions. The depth of the socket (9.*b*) varies from about 2 mm to about 5 mm and its diameter varies from about 1 mm to about 5 mm. The diameter of the head of the retention screw (9.*h*) is larger than the maximum diameter of the hollow channel of the angulated abutment (7.*u*) and impression post (8.*a*). The diameter of the thread (9.*u*) of the long retention screw (9.*e*) is smaller than the minimum diameter of the hollow channel (7.*u*, 8.*a*). The head (9.*h*) of the long retention screw (9.*e*) couples to the upper part (7.*i*) of the hollow channel (7.*u*) of the angulated abutment (7.*r*) and to the top part (8.*abe*) of the hollow channel (8.*a*) of the angulated impression post (8.*k*) and isolates them from the space of the open well of the superstructure of the mold (10.*j*, 11.*j*) while it expands height-wise out of the proximal open bore of the hollow channel (10.*p*, 11.*r*) to an extent such that the proximal border of its head is located outside the top borders of the superstructure of the mold (FIGS. 10E, 11E) when the angulated abutment (10.*o*) and impression post (11.*p*) are connected to the prosthetic connection of the base of the mold (10.*k*, 11.*k*). The purpose of this retention screw (10.*u*, 11.*u*) is the retention of the angulated abutment (10.*o*) and impression post (11.*p*) into the mold, to maintain an entrance channel (2.*a*, FIG. 2D section A-A, 3.*a*, FIG. 3D section A-A) free of biocompatible material towards the prosthetic connection of the angulated abutment and impression post (2.*m*, 3.*o*) for a short retention screw (9.*a*) that will be utilized for the connection of the latter (2.*r*, 3.*f*) with an implant (4.*e*) in the mouth.

FIGS. 23A-23C describe a retention handle (23.*d*) of the custom abutments (23.*e*) and impression posts (23.*h*) aiming at the easy and secure polishing of their custom part (2.*b*, 3.*b*) that is fabricated by biocompatible material with polishing brushes (23.*u*, 23.*z*) after they are fabricated and uncoupled by the mold. The retention handle (23.*d*) is a solid cylinder that has a flat surface on each of its two ends this flat surface (23.*i*) has a diameter that is larger than the diameter of the base of the shoulder of the custom abutment (7.*o*) and of the impression post (8.*d*). The flat surface (23.*i*) has one or more sockets (23.*g*) with shape and dimensions corresponding to the ones of the prosthetic connections of the base of the mold (1.*n*, 22.*z*). Thus the sockets (23.*g*) might have a shape of external hexagon (1.*d*, FIG. 1F1), internal hexagon (1.*e*, FIG. 1F2), internal trilobe (1.*z*, FIG. 1F3), internal octagon (1.*h*, FIG. 1F4), conical (1.*u*, FIG. 1F5), circular with vertical groves (1.*i*, FIG. 1F6), cut slot (1.*k*, FIG. 1F7) with different degrees of bevel and depth. These sockets (23.*g*) at their base have a blind threaded bore (23.*k*) that allows the threaded coupling of a retention screw (23.*a*) of the custom abutment (23.*b*) and impression post (23.*h*) aiming to the secure connection and retention of the latter onto the handle (FIG. 23A). The longitudinal axis of these sockets may have angulations towards the vertical that vary from about 0 to about 45 degrees (FIG. 23A). This handle (23.*d*) is preferably metallic or ceramic or plastic or a combination of the aforementioned and its length varies from about two to about twenty centimeters.

FIGS. 4A, 5A-5D, 6A, 7A-7D and 10A-10E describe an angulated titanium abutment (7.*r*) that functions as a core around which the one-piece custom, potentially modifiable abutment (2.*r*) is fabricated by the inventive mold (22.*a*, 1.*a*). The abutment (7.*r*) is a solid piece that is descriptively divided to three parts (7.*j*, 7.*n*, 7.*m*).

The first part of the abutment (7.*j*) is a prosthetic connection that is a conical (4.*i*), or polyhedron (4.*u*) pillar that is the exact negative replication of the prosthetic connection of an implant (4.*g*). The prosthetic connection (7.*j*) interconnects and couple locks to the corresponding prosthetic connection (1.*n*, 22.*z*, 24.*n*) of the base (1.*g*, 22.*b*, 24.*r*) of the mold (1.*a*, 22.*a*) passively and without being able to freely rotate (10.s). Thus, the prosthetic connection of the impression posts (8.o, 11.i) can have a shape that is conical (4.i), or external hexagon (1.d, FIG. 1F1), or internal hexagon (1.e, FIG. 1F2), or internal trilobe (1.z, FIG. 1F3), or internal octagon (1.h, FIG. 1F4), or circular with vertical groves (1.i, FIG. 1F6), etc., with different degrees of bevel and depth corresponding in type and size of the prosthetic connection (4.g) of the implant (4.e). The angulations (7.aa, 10.aa) of the prosthetic connection of the abutment (7.j, 7.l, 10.i) towards the vertical is similar to the one (10.aa) of the prosthetic connection (10.k) of the base (1.g, 22.b, 24.r) with which it couples and varies from about 1 to about 45 degrees.

Above the prosthetic connection (7.j) there is a second part that is the abutment shoulder (7.n). The shoulder of the abutment (7.n) is a cylinder of variable section that has a base (7.o) of which the diameter and shape is exactly the same with the implant platform (4.d) of the corresponding in size and type implant (4.e). In continuation to the base (7.o) the shoulder (7.n) has sidewalls (7.z) that are straight (6.a), or convex (6.g), or concave (6.b), or curved (FIG. 7D section A-A) and end at the surface that is the upper surface of the shoulder (7.e). The diameter of the upper surface (7.e) is equal or larger than the one of the base (7.o). The height of the shoulder (7.n) varies from about 1 mm to about 7 mm. The surface of the shoulder (7.n) is polished or lightly etched in a microscopic level.

The third part is a pillar (7.m) that has cylindrical (7.r), or polyhedron shape (4.a, 4.z) with flat (4.m) or flat and curved surfaces (31.eb), where the flat surfaces (4.m) are fully corresponded in space with one or more of the flat surfaces of the prosthetic connection of the abutment (4.u). The pillar of the abutment (10.o) might have a concave grove around its body in proximity to the upper surface of the shoulder (31.e) that has curved borders (31.eb) and that is oriented perpendicular to the orientation of the pillar (7.m). The pillar (7.m, 10.o) has angulations (10.aa) parallel to the vertical when the abutment is coupled with the prosthetic connection (10.k) of the base of the mold (1.n, 22.z), or the prosthetic connection of the implant (4.g). The pillar has a height that varies from about 3 mm to about 12 mm. The surface of the pillar (7.m) is available in at least two different types. The first type (5.b) has a surface that is rough with pits and valleys on its full length. The second type (5.a) has only a portion of the pillar that is in continuation to the upper surface of the shoulder (7.n) and it has a surface that is rough with pits and valleys while the rest of the pillar has a polished surface. The diameter of the pillar (7.m) is equal or smaller to the one of the upper surfaces of the shoulder (7.e).

The titanium abutment (7.r) has a hollow channel (7.u) that is descriptively divided in two parts, an upper (7.i) and a lower (7.h). The diameter of the upper part (7.i) is larger than the diameter of the bottom part (7.h). The diameter of the upper part (7.i) is larger than the maximum diameter of a short retention screw (9.a) and of the diameter of the threaded portion (9.u) of a long retention screw (9.e) and at the same time smaller than the diameter of the head of the latter (9.h). The diameter of the lower part (7.h) is larger than that of the threaded portion (9.z, 9.u) and at the same time smaller than that of the head of the short (9.d) and long (9.h) retention screw. The hollow channel (7.u) enables the entrance of the retention screw (9.a, 9.e) and it has its upper open bore (7.a) located on a side wall of the pillar (7.m), while the bottom open bore (7.p) of the hollow channel (7.u) is located on the bottom surface of the prosthetic connection of the abutment (7.l).

FIGS. 30A-30L and 31A-31F describe a two-piece system (30.b) that comprise an abutment (30.a) and a cap (30.aa) that couples with the pillar of the abutment (30.ab). The cap (30.aa) that we call abutment cap (30.aa) couples onto the pillar of the abutment (30.ab) through a blind bore which has a length equal to the height of the pillar (30.ab), that has on its bottom part, aiming to the establishment of a two-piece (30.aa, 30.a) core (30.b) that is used for the fabrication of a custom potentially modifiable two-piece (30.ha, 30.h) abutment (30.e). The abutment cap (30.aa) is a pillar with stable or variable section and regular or irregular surfaces that are smooth or rough or smooth and rough. The pillar (30.aa) has a shape that is cylindrical, or cylindrical with one flat seat or polyhedron, where the flat surface or surfaces are fully corresponded in space with one or more of the seats of the prosthetic connection (4.u) of the abutment (4.a, 30.a). The abutment cap (30.aa), after it is coupled with the pillar of the abutment (30.ab), extends in height from the upper surface of the abutment shoulder (2.z) to the free end of the abutment pillar (2.d, 30.ab) or even further than the latter. The internal surface of the abutment cap (30.aa) has a shape that replicates the exact negative replication (31.e, 31.z) of the external surface and or part of the hollow channel of the pillar (30.ab) of an abutment (30.a) that has a pillar (30.ab) which around its body in the part located close to its shoulder (31.e, 31.z) has a concave groove with curved borders (31.eb) that is oriented vertically towards the pillar (30.ab). This groove (31.eb) allows the snap on connection (31.za) with its negative replication (31.ea) present in the inner surface of the corresponding bottom part of the abutment cap (30.aa) and with this way the complete, stable, precise and snap on coupling of the two pieces (31.z) to one piece (30.b) is achieved.

Figure 13A:
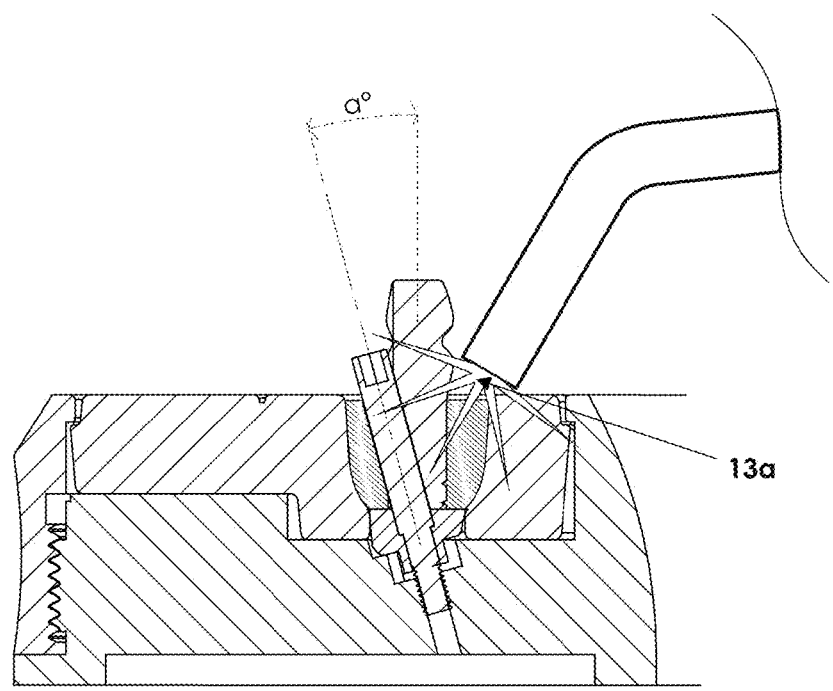
FIG. 13A is an exploded cross-sectional view of an exemplary mold.
Figure 13B:
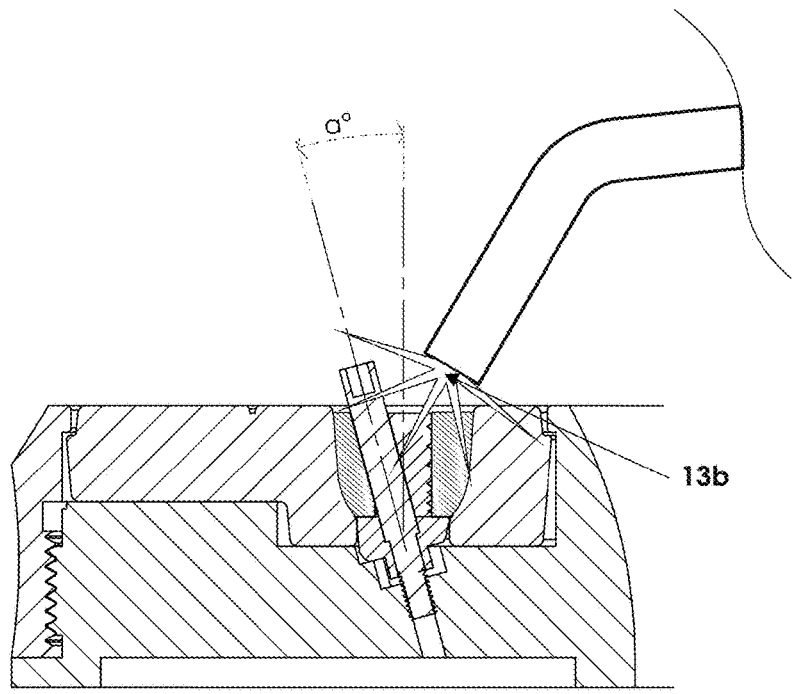
FIG. 13B is an exploded cross-sectional view of an exemplary mold.
Figure 14A:
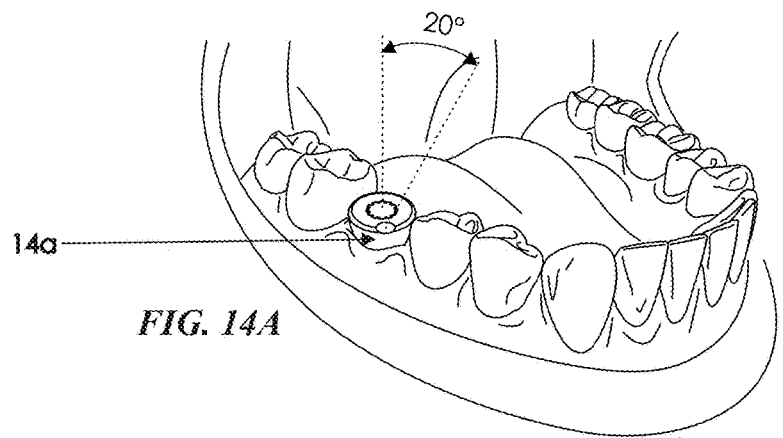
FIGS. 14A-14D are perspective views of aspects of an exemplary process for installation of implants.
Figure 14B:
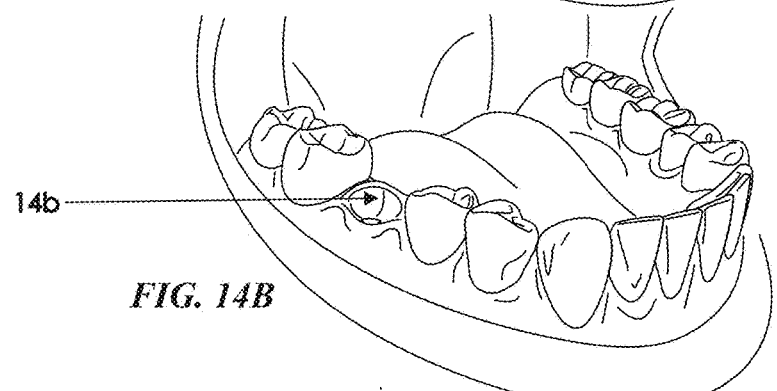
Figure 14C:
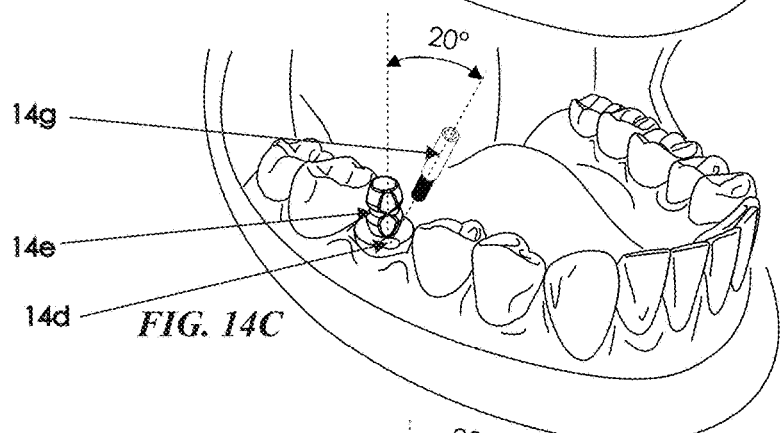
Figure 14D:
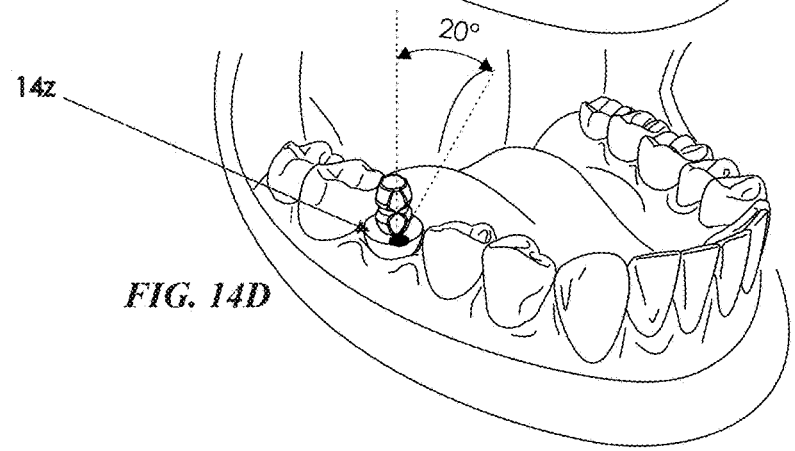
Figures 15A, 15B, 15C, 15D, 15E:
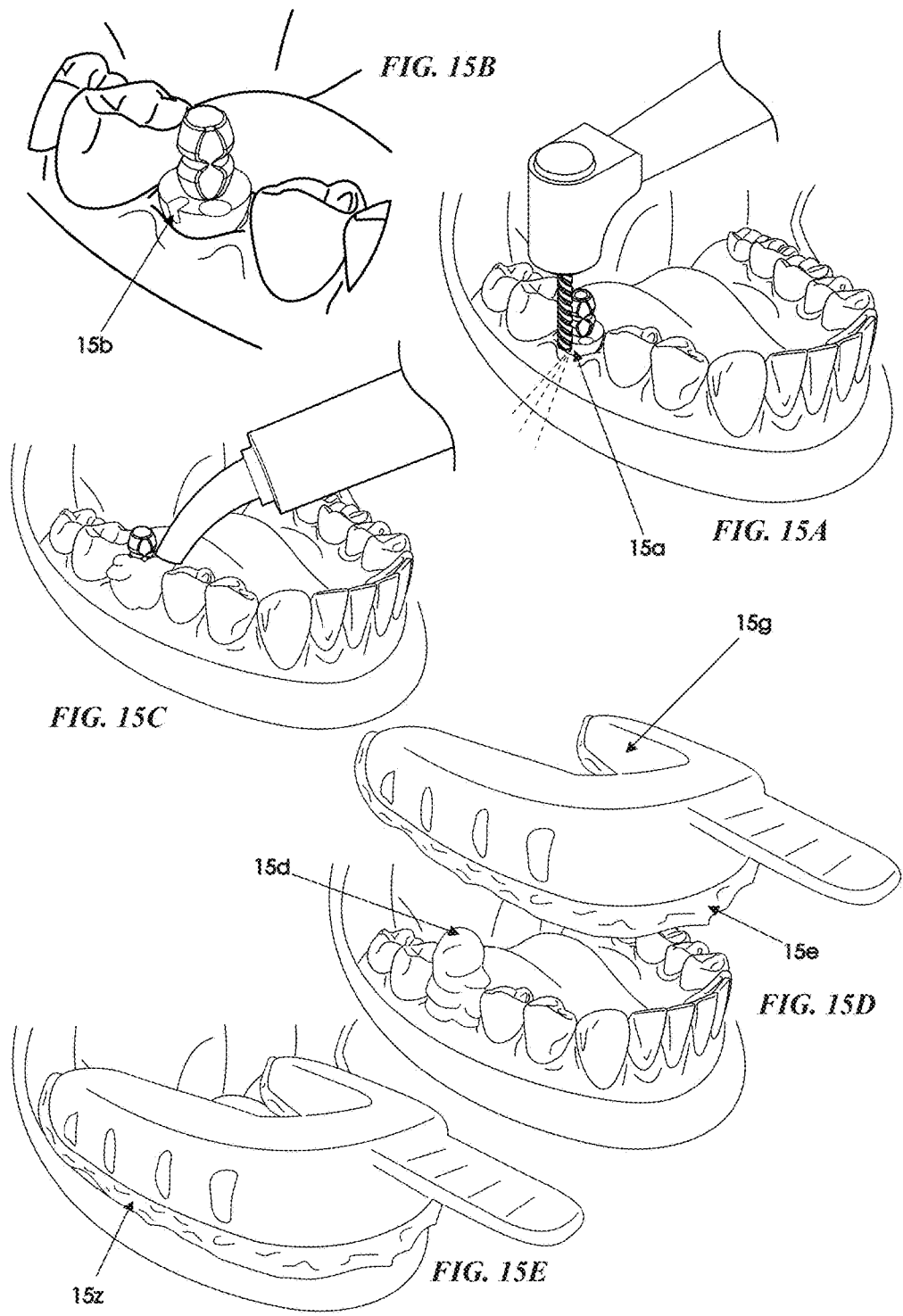
FIGS. 15A-15E are exploded and perspective views of aspects of an exemplary process for installation of implants.

A related method for the fabrication of one-piece custom potentially modifiable abutments (2.r) with various degrees of angulations towards the vertical (FIGS. 10E, 12A-12B, 13A-13B), where the method includes the availability and utilization of a mold (1.a, 22.a) as it has been previously described. The availability and utilization of an abutment (10.e) with different degrees of angulations toward the vertical, that is made out of titanium or other biocompatible material is coupled through its prosthetic connection (10.i) with the compatible in angulations and fit prosthetic connection of the base of the mold (10.k) inside the space of the corresponding well of the superstructure of the mold (10.b) with a long retention screw (10.u, 10.d) that has been coated with a separating or isolating material. The retention screw couple threads to the threaded portion of the blind bore of the base (24.j). Thus the angulations of the prosthetic connection of the abutment (10.i) are similar to the prosthetic connection of the base (10.k) that it is connected with, towards the vertical (10.aa). The shoulder (10.l) and the pillar of the abutment (10.n) are oriented within the open well of the superstructure of the mold (10.j, 10.b). Specifically, the bottom part of the open well of the superstructure (24.h) receives the abutment shoulder (10.l), of which the upper surface (12.bm) isolates the bottom part of the well of the superstructure (24.h) from the top part (24.l) thereof. The pillar part of the abutment (10.n) is located within the side borders (10.m, 24.m) of the upper part of the well of the superstructure (24.l) with an angulations parallel towards the vertical (FIGS. 10E, 12A-B, 13A-B) and in this way it comprises a core around which the body of the custom abutment (FIG. 2D section A-A) is fabricated. After the final secure coupling of the abutment (10.e) to the prosthetic connection of the base of the mold (12.bu) with a long retention screw (12.bn), the space of the bottom part of the well of the superstructure (24.h) is fully isolated from the upper part of the well (24.l) from the upper surface of the shoulder of the abutment (12.bm) while at the same time the head of the long retention screw (12.bg) isolates the hollow channel of the abutment (7.u) and it extends outside the top borders of the walls (10.r, 10.g, 24.k) of the open well of the superstructure (FIGS. 10A, 10E, 12A-12B, 13A-B). The long retention screw (12.bn) before its use is covered with Vaseline or other isolating material in order to prevent the connection of it with the biocompatible material (12.bl) that will be introduced afterwards to the well. Following this, a curable biocompatible material (12.bl) with radio-opaque properties and ability to be scanned by a digital scanner (17.e) is introduced in the space (10.j) between the inner walls of the upper part (24.l) of the well of the superstructure of the mold (10.m, 24.m) and the part of the pillar of the abutment (10.n). The biocompatible material extends in height from the top surface of the abutment shoulder (12.bm) to the top end (10.r, 24.k) of the walls of the well of the superstructure of the mold (FIGS. 13A-13B). After the curing and setting of the biocompatible material (13.b) the long retention screw (10.d, 12.bn, 10.u) is removed with a corresponding screwdriver and following the system titanium abutment, biocompatible material is removed from the mold. This system we refer to as a custom, potentially modifiable abutment (10.h, 2.r). This system after the long retention screw (10.d, 10.u, 12.bn) is removed presents a hollow channel (2.a, 2.g) that gives access to its prosthetic connection (2.m) that allows the free entrance of a short retention screw (9.a) when this is needed in the future. The custom potentially modifiable abutment (10.h, 2.r, 23.b) is then coupled to the socket (23.g) of the upper surface (23.i) of the retention handle (23.d) with a long or short retention screw (23.a) and its body gets polished and abraded if needed, with brushes and paste for abrasion and polishing (23.z) in order to establish its final surface texture and shape (23.e). Following this, the custom abutment (10.h, 2.r, 23.e) is uncoupled from the handle (23.d) with removal of the retention screw (23.a) and subsequently it gets disinfected and sterilized before it will be used in clinical practice. The custom, potentially modifiable abutments (10.h, 2.r) that are fabricated with the methodology described above (12.b) have oval or cylindrical shape that expands laterally, gradually, and upwards with symmetrical section, smooth and regular surfaces and with a large variety in height, diameter and angulations (FIGS. 2A-2D). However, because the custom body (2.b, 10.z) of the abutment is made out of biocompatible material (12.bl) that can be easily modified (abrasion) it can be abraded and modified three dimensionally by the dentist, intra-orally (FIGS. 18A-18C) and extra-orally (FIGS. 23A-23C) according to the needs of each individual clinical case. This way a custom, potentially modifiable one-piece abutment (2.r) is fabricated with various degrees of angulations towards the vertical.

A related method for the fabrication of two-piece custom potentially modifiable abutments with various degrees of angulations towards the vertical (30.e) includes the availability and utilization of a mold (1.a) as it has been described herein. One abutment (30.u, 10.e) with different degrees of angulations toward the vertical (10.aa) made out of titanium or other biocompatible material is coupled through its prosthetic connection (10.i) with a compatible in angulations and fit prosthetic connection of the base of the mold (10.k) inside the space of the corresponding well of the superstructure of the mold (10.β) and is retained stable in position with the use of a retention screw (10.u, 10.d) that couple threads with the threaded portion of the blind bore of the base of the mold (24.j). Thus, the angulations (10.aa) of the prosthetic connection of the abutments (10.i) is similar to one of the prosthetic connections of the base of the mold (10.k) that it is connected with, while the upper surface of the shoulder of the abutment (12.bn) isolates the bottom part of the well of the superstructure (24.h) from the top part thereof (24.l). Following this, the abutment cap (FIGS. 31A-31F, 31.aa) couples with snap on connection (31.e, 31.z) to the pillar of the abutment (31.ab) so that the pillar (30.ab, 30.ag) as a whole is located within the cap. The snap on coupling (31.za) is achieved with the coupling of the concave groove (31.eb) present in the lower part of the pillar with the convex extension (31.eb) that is the negative replication of the concave groove (31.eb) and which (31.ea) is present to the corresponding part of the internal surface (31.e) of the abutment cap (30.aa). The abutment pillar (10.n, 31.ab) and the abutment cap (31.aa) are located sideways within the side borders of the upper part of the open well of the superstructure with angulations parallel towards the vertical (31.b) and this two-piece system comprises a core around which the body of the custom abutment cap (30.ha) is respectively fabricated.

Following this, a curable radio-opaque and potentially digitally scan-able, biocompatible material (12.bl) is introduced in the space (10.j) between the inner walls of the upper part of the well of the superstructure of the mold (10.m, 24.m) and the part of the abutment cap that covers the pillar of the abutment (31.aa). The biocompatible material extends in height from the top surface of the abutment shoulder (12.bm) to the top end (10.r, 24.k) of the walls of the well of the superstructure of the mold (FIGS. 13A-13B). After the curing and setting of the biocompatible material (13.b), the abutment cap (31.aa) is mechanically or chemically connected with the biocompatible material (12.bl) to form one-piece. Following this, the custom abutment cap (30.ha) is pulled out from the pillar of the abutment (30.hb) and then the retention screw (10.d) is removed and the abutment (10.e, 30.h) is now uncoupled from the mold (10.a). Following this, the abutment (30.h) is couple threaded to the socket (23.g) of the upper surface (23.i) of the retention handle (23.d) with a retention screw (23.a) and subsequently the custom abutment cap (30.ha) is snapped onto the pillar of the abutment (30.hb) and then the custom body (30.e) is abraded and polished with brushes and paste for abrasion and polishing (23.z). Following this, the abutment cap (30.ha) is uncoupled by the pillar of the abutment and following the abutment (30.h) is uncoupled from the handle (23.d) with removal of the retention screw (23.a) and they then receive disinfection and sterilization before their use in the clinical practice. Following this methodology, a two-piece (30.ha, 30.h) custom potentially modifiable abutment (30.e) with various degrees of angulations toward the vertical (12.bbb) as this is determined by the angulations (7.aa) of the prosthetic connections of the abutment (30.a), is made. This system comprises two pieces (30.ha, 30.h) that can coupled and uncoupled with each other.

FIGS. 4D, 5A-5D, 6A-F and 8A-E describe angulated closed tray impression posts that function as cores for the fabrication of the custom potentially modifiable angulated impression posts (3.f) from the inventive mold (1.a, 22.a).

The angulated closed tray impression post (8.k) is preferably made out of metal (stainless steel, titanium, aluminum, etc.), or ceramic material and it descriptively comprises of a prosthetic connection (8.o), a shoulder (8.p), a pillar (8.z), a fourth part that we call polymorphic (8.u), all of them in the form of one piece that presents a hollow channel (8.a) that allows the free path of a short (9.a) or long (9.e) retention screw aiming to the couple threaded connection (8.k) of the impression post with an implant or an implant analog (4.e).

The prosthetic connection of the impression post (8.o) is a conical (4.l), or polyhedron (4.k) pillar that is the exact negative replication of the prosthetic connection of an implant (4.g). The prosthetic connection (8.o) interconnects and couple locks to the corresponding prosthetic connection (1.n, 22.z) of the base (1.g, 22.b) of the mold (1.a, 22.a) passively and accurately (FIGS. 11A-D) and it is unable to freely rotate (11.s). Thus, the prosthetic connection of the impression posts (8.o, 11.i) can have a shape that is conical (4.l), or external hexagon (1.d, FIG. 1F1), or internal hexagon (1.e, FIG. 1F2), or internal trilobe (1.z, FIG. 1F3), or internal octagon (1.h, FIG. 1F4), or circular with vertical groves (1.i, FIG. 1F6), etc., with different degrees of bevel and depth corresponding in type and size of the prosthetic connection (4.g) of the implant (4.e). Thus, when an impression post (8.k) is connected with an implant (4.e) with corresponding in type and size prosthetic connection (4.g), the prosthetic connection of the impression post (8.o) is inserted passively and accurately to the prosthetic connection of the implant (4.g) achieving the stable connection of the impression post (8.k) with the implant (4.e) and making impossible the rotational movement of the impression post. The angulations (11.aa) of the prosthetic connection of the impression post (11.i) towards the pillar (11.n) and the polymorphic part (11.o) of the impression post vary from about 1 to about 45 degrees.

Above the prosthetic connection (8.o) there is a second part that is the impression post shoulder (8.p). The shoulder of the impression post (8.p) is a cylinder of variable section that has a base (8.d) of which the diameter and shape is exactly the same with the implant platform (4.d) of the corresponding in size and type implant (4.e). In continuation to the base (8.d) the shoulder (8.p) has sidewalls (8.r) that are straight (6.d), or convex (6.z), or concave (6.e), or curved (FIG. 8E section A-A) and end at the surface that is the upper surface of the shoulder (8.s). The diameter of the upper surface (8.s) is equal or larger than the one of the base (8.d). The height of the shoulder (8.p) varies from about 1 mm to about 7 mm. The surface of the shoulder (8.p) is polished or lightly etched in a microscopic level.

The third part is a pillar (8.z) that has cylindrical (5.g, 5.d), or polyhedron shape (4.b, 4.h) that starts from the upper surface of the shoulder (8.s) and ends at the base (8.c) of the polymorphic part (8.u). The diameter of the pillar (8.z) is smaller or equal to the one of the base of the shoulder (8.d) and subsequently to the one of the prosthetic platform of the implant (4.d). The pillar (8.z) has a height that varies from about 2 mm to about 11 mm. The surface of the pillar (8.z) is available in two different types for the total closed tray angulated impression posts (FIG. 5A-5D). The first type (5.d) has a surface that is rough with pits and valleys on its full length. The second type (5.g) has only a portion of the pillar that is in continuation to upper surface of the shoulder (8.s) that has a surface that is rough with pits and valleys while the rest of the pillar has polished surface. The rough surface with pits and valleys ensures the stable mechanical retention of the biocompatible curable material on it (3.b, 3.h). Thus impression posts with the first type pillar (5.d) are utilized in clinical cases where the depth of the gingival emergence profile is deep and the pillar must be customized in its full length, while the impression posts with second type pillar (5.g) are utilized in clinical cases where the gingival emergence profile is shallow and only a part of the pillar needs to be customized. The pillar (8.z, 11.n) is oriented parallel to the vertical when the impression post (8.k) is connected through its prosthetic connection (11.i) with the prosthetic connection (11.k) of the base of the mold (FIG. 11E).

Figure 8A:
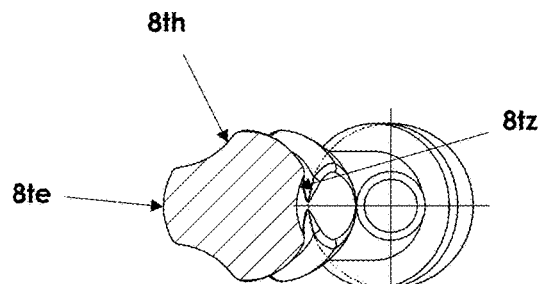
FIG. 8A is a perspective and partial cross-sectional view of an exemplary impression post.
Figure 8B:
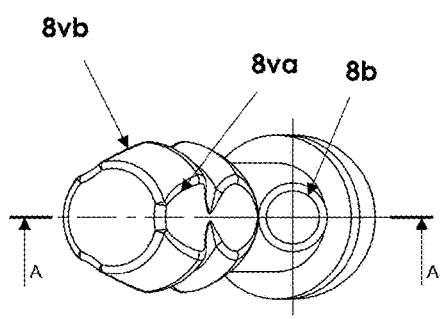
FIG. 8B is a perspective view of an exemplary impression post.
Figure 8C:
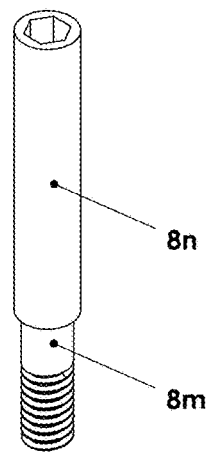
FIG. 8C is a perspective view of an exemplary retention screw.
Figure 8D:
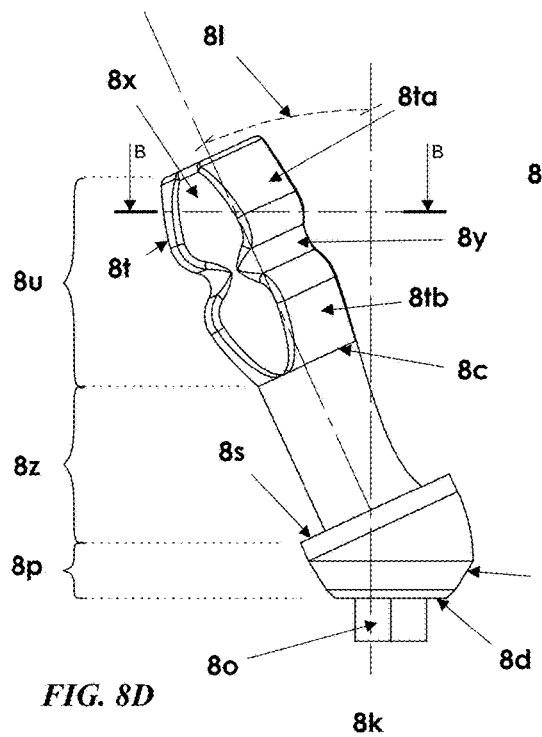
FIG. 8D is a perspective and partial sectional view of an exemplary impression post.
Figure 8E:
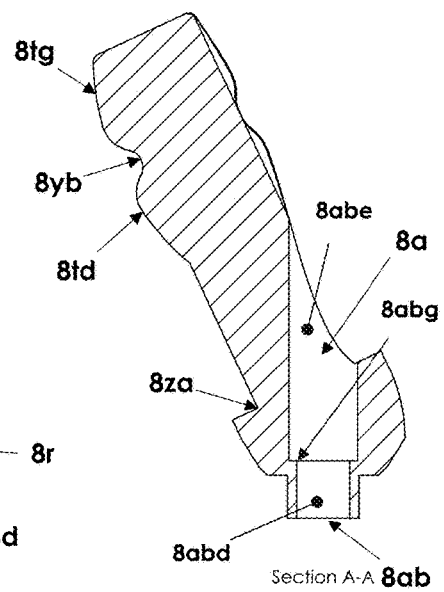
FIG. 8E is a cross-sectional view of an exemplary impression post.

The polymorphic part (8.u) is a cylinder with variable section that has three vertical, curved surfaces (8.t) that intercept each other through three vertical, concave surfaces of smaller radius (8.x). Each of the three curved surfaces (8.t) of the polymorphic part (8.u) is divided into two convex parts, upper (8.ta, 8.tg) and lower (8.tb, 8.td) from a horizontal, concave surface of smaller radius (8.y, 8.yb) that is located in their mid-portion (FIGS. 8D-8E). The areas of connection of the different shape surfaces (8.va, 8.vb) are curved without any acute angles. Each of the convex surfaces (8.te) of the polymorphic part (8.u) presents curved sidewalls (8.ty, 8.tz). The maximum diameter of the polymorphic part (8.u) is smaller, or equal, or bigger than the diameter of the base of the shoulder of the impression post (8.d). The horizontal concave surface (8.y, 8.yb) has a diameter that is equal to the diameter of the pillar (8.z). The polymorphic part (8.u) as a whole has a smooth surface and its height varies from about 5 mm to about 20 mm. The polymorphic part (8.u) in cross section (FIG. 8E section A-A) presents a curved surface that is divided into two equal convex parts, upper (8.tg) and lower (8.td) through a concave surface (8.yb). The polymorphic part (8.u) in horizontal section (FIG. 8A section B-B) presents a trihedral shape that resembles a propeller with three wings, of which the outer surface (8.te) is convex, while the two sidewalls (8.th, 8.tz) are concave. Each of the vertical curved surfaces of the polymorphic part (4.j) is fully corresponded in space with one or more of the seats of the prosthetic connections of the impression post (4.k). The polymorphic part (11.o) is parallel to the vertical when the impression post (8.k) is connected through its prosthetic connection (11.i) with the prosthetic connection of the base of the mold (11.k).

The hollow channel (8.a) of the angulated closed tray impression post (8.k) is divided in two parts, an upper (8.abe) and a lower (8.abd). The diameter of the upper part (8.abe) is larger than the diameter of the bottom part (8.abd). The diameter of the upper part (8.abe) is larger than the maximum diameter of a short retention screw (9.a) and of the diameter of the threaded portion (9.u, 8.m) of a long retention screw (9.e) and at the same time smaller than the diameter of the head of the latter (9.h, 8.n). The diameter of the lower part (8.abd) is larger than that of the threaded portion (9.z, 9.u) and at the same time smaller than that of the head of the short (9.d) and long (9.h) retention screw. The hollow channel (8.a) has two open bores (8.b, 8.ab). The upper open bore (8.b) is located on a side wall of the pillar (8.z), or of the polymorphic part (8.u), or of both (8.z, 8.u) of the aforementioned, while the bottom open bore of the hollow channel (8.ab) is located on the bottom surface of the prosthetic connection of the impression post (8.o).

FIGS. 30A-30L describe a two-piece system (30.d) that comprises an abutment (30.g) and a cap (30.ga) that couples onto the pillar of the abutment (30.gb). The cap (30.ga) that we call impression abutment cap (30.ga) couples onto the pillar of the abutment (30.gb) through a blind bore on its bottom end, and which blind bore has a length that is equal to the height of the pillar of the abutment (30.gb), aiming to the establishment of a two-piece (30.ga, 30.g) core (30.d) that is used for the fabrication of a custom potentially modifiable two-piece (30.ua, 30.u) impression post (30.z). The impression abutment cap (30.ga) is a post with variable section that is divided in two parts (30.ia, 30.ib) as one piece (30.ga). The first part (30.ia) is a pillar that has a shape that is cylindrical, or cylindrical with one flat seat, or polyhedron where the flat surface or surfaces are fully corresponded in space with one or more seats of the prosthetic connection (4.*u*) of the abutment (30.*g*). The pillar (30.*ia*) has a stable, or variable section and regular, or irregular surface that is polished or rough while its internal surface has a shape that replicates the exact negative replication (31.*e*, 31.*z*) of the external surface alone and or additionally a part of the hollow channel of the pillar (30.*gb*) of an abutment (30.*g*) of which the pillar moreover has a concave groove with curved borders (31.*eb*), oriented vertically towards the pillar (31.*gb*), around its body in a part (31.*e*) of it that is located close to its shoulder (2.*z*) and which groove (31.*eb*) allows the complete, stable, precise snap on coupling of the two pieces (31.*ea*, 31.*eb*) to each other (31.*za*) as one piece (31.*z*, 30.*d*). The second part of the impression abutment cap (30.*ib*) is a solid cylinder of variable section with three vertical curved surfaces (30.*ih*) that are distinguished between each other from three vertical convex surfaces of smaller radius (30.*id*). The vertical curved (30.*ih*) and convex (30.*id*) surfaces are all or some of them fully corresponding in space with all or some of the flat surfaces (4.*k*) of the prosthetic connection (8.*o*) of the abutment (8.*k*, 30.*g*). Each one of the three vertical curved surfaces of the cylinder (30.*ih*) is divided in two convex parts, upper (30.*ie*) and lower (30.*iz*) from a horizontal convex surface of smaller radius (30.*ig*) that is located at their mid-point (FIG. 30B). The maximum diameter of the cylinder (30.*ib*) is smaller or equal or larger than the diameter of the base of the abutment shoulder (8.*d*). The horizontal convex surface of smaller radius (30.*ig*) has a diameter that is smaller or equal or larger than the one of the pillar (30.*ia*). The second part of the impression abutment cap (30.*ib*) as a whole has smooth or rough surface and its height may vary from about 3 mm to about 20 mm. The impression abutment cap (30.*ga*) has the same angulations toward the vertical with the pillar part (30.*gb*) of the abutment (30.*g*). The impression abutment cap (30.*ga*, 31.*ga*) and the pillar (30.*gb*) of the abutment (30.*g*, 31.*gb*) are oriented parallel to the vertical when the system abutment-impression abutment cap (30.*d*) is coupled to the prosthetic connection of the base of the mold (31.*d*).

Following the same steps as previously described for the method of fabrication of custom potentially modifiable abutments (2.*r*, 10.*h*) with the utilization of the inventive mold (1.*a*, 22.*a*) corresponding with them in shape and size custom, potentially modifiable impression posts (3.*f*, 11.*h*) can be fabricated (FIGS. 11A-E, 12A-12B, 13A-13B). The impression post (11.*e*, 11.*p*) is coupled through its prosthetic connection (11.*i*) with the compatible in angulations and fit prosthetic connection of the base of the mold (11.*k*) inside the space of the corresponding well of the superstructure of the mold (1.*l*, 22.*g*) with a long retention screw (11.*u*) that has been coated with a separating or isolating material. The retention screw couple threads to the threaded portion of the blind bore of the base (24.*j*). Thus the angulations of the prosthetic connection of the impression post (11.*i*) are similar to the one of the prosthetic connection of the base (11.*k*) that it is connected with, towards the vertical (11.*aa*). The bottom part of the open well of the superstructure (24.*h*) receives the impression post shoulder (11.*l*), of which the upper surface (12.*am*) isolates the bottom part of the well of the superstructure (24.*h*) from the top part (24.*l*) thereof. The hollow channel of the impression post (8.*a*) is isolated by the head of the long retention screw (8.*n*, 9.*h*, 11.*r*), which (11.*r*) extends up to or further out than the top borders (24.*k*) of the open well of the superstructure of the mold (24.*b*). Following this, a curable biocompatible material (12.*al*) with radio-opaque properties and ability to be scanned by a digital scanner (17.*e*) is introduced in the space (111.*j*) between the inner walls of the upper part of the well of the superstructure of the mold (11.*m*) and the part of the pillar of the abutment (11.*n*). The biocompatible material extends in height from the top surface of the shoulder (12.*am*) to the top end of the pillar (8.*c*), without expanding to the polymorphic part of the impression post (8.*u*). After the curing and setting of the biocompatible material (13.*a*) the long retention screw (12.*ag*) is removed with a corresponding screwdriver and following this the system titanium impression post-biocompatible material (11.*h*, 3.*f*) is removed from the mold. This system that we refer to as an angulated custom, potentially modifiable impression post (11.*h*, 3.*f*) may then be connected with a compatible socket (23.*g*) of a retention handle (23.*d*) with a retention screw (23.*a*) and its body gets polished and abraded if needed (23.*u*). Following this, the custom impression post is uncoupled from the handle (23.*d*) with removal of the retention screw (23.*a*) and subsequently it gets disinfected and sterilized before it will be used in clinical practice. This way, custom, potentially modifiable one-piece impression posts (3.*f*) with various degrees of angulations towards the vertical are fabricated through the inventive mold (1.*a*).

A related method for the fabrication of two-piece, custom, potentially modifiable impression posts with various degrees of angulations towards the vertical (30.*z*), that comprises two coupling pieces (30.*ua*, 30.*u*) is described below. After the coupling of the abutment (30.*g*) through its prosthetic connection with a compatible in angulations and fit prosthetic connection of the base of the mold (24.*n*) inside the space of the corresponding well of the superstructure of the mold (1.*l*), the abutment is retained stable and in position with the use of a retention screw (10.*u*, 10.*d*) that couple threads with the threaded portion of the blind bore of the base of the mold (24.*j*). The upper surface of the shoulder of the abutment (7.*e*) isolates the bottom part of the well of the superstructure (24.*h*) from the top part thereof (24.*l*). Following this, the abutment impression cap (30.*ga*, 31.*ga*) couples with snap on connection (31.*e*, 31.*z*) to the pillar of the abutment (30.*gb*, 31.*gb*) so that the pillar (30.*gb*, 31.*gb*) as a whole is located within the cap (30.*ga*, 31.*ga*). The snap on coupling (31.*za*) is achieved with the coupling of the concave groove (31.*eb*) present in the lower part of the pillar with the convex extension (31.*ea*) that is the negative replication of the concave groove (31.*eb*) and which (31.*ea*) is present to the corresponding part of the internal surface (31.*e*) of the abutment cap (31.*ga*, 30.*ga*). Following this, a curable radio-opaque and potentially digitally scan-able, biocompatible material (12.*al*) is introduced in the space between the inner walls of the upper part of the well of the superstructure of the mold (12.*ad*) and the post part of the impression abutment cap (30.*ia*). The biocompatible material (12.*al*) extends in height from the top surface of the abutment shoulder (7.*e*) to the top end of the post part of the abutment impression cap (30.*ia*). After the curing and setting of the biocompatible material (13.*a*), the abutment impression cap (30.*ga*) is mechanically or chemically connected as one piece with the biocompatible material (12.*al*). Following this, the custom impression abutment cap (30.*ua*) is pulled out from the pillar of the abutment (30.*ub*) and then the retention screw (10.*d*) is removed and the abutment (30.*g*, 30.*u*) is now uncoupled from the mold (10.*a*, 1.*a*). Following this, the abutment (30.*u*) is couple threaded to the socket (23.*g*) of the upper surface (23.*i*) of the retention handle (23.*d*) with a retention screw (23.*a*) and subsequently the custom abutment impression cap (30.*ua*) is snapped onto the pillar of the abutment (30.*ub*) and then the custom body is abraded and polished with brushes and paste for abrasion and polishing (23.*z*). Following this, the custom abutment impression cap (30.*ua*) is uncoupled by the pillar of the abutment (30.*ub*) and then the abutment (30.*u*) is uncoupled from the handle (23.*d*) with removal of the retention screw (23.*a*) and they both receive disinfection and sterilization before they are used in the clinical practice. Following this method two-piece (30.*ua*, 30.*u*), custom, potentially modifiable impression posts (30.*z*) with various degrees of angulations toward the vertical as this is determined by the angulations (7.*aa*) of the prosthetic connections of the abutment (30.*u*) are made. This system comprises two pieces (30.*ua*, 30.*u*) that can couple and uncouple with each other (31.*e*, 31.*z*).

Thus the dentist can fabricate through the utilization of the inventive mold (1.*a*, 22.*a*) corresponding in shape, dimensions and angulations, custom, potentially modifiable one-piece (2.*r*, 10.*h*) and two-piece (30.*e*) abutments and custom potentially modifiable one-piece (3.*f*, 11.*h*) and two-piece (30.*z*) impression posts for the fulfillment of the surgical phase of development of a custom emergence profile around an implant platform that has been placed with similar or different angulations towards the longitudinal axis of the final prosthesis that will be installed on it but also for the accurate recording and transfer of the aforementioned information onto the working cast where the final prosthesis will be fabricated (FIGS. 14A-14D, 15A-15E, 16A-16E, 20A-20B).

An additional exemplary application of the custom potentially modifiable abutments with different degrees of angulations towards the vertical is the following. If at any time point of treatment the dentist wishes to restore the implant with a temporary prosthesis, then the custom abutment (18.*b*) that is coupled with the implant in the mouth (FIGS. 18A-18C) can be prepped supra-gingivally by abrasion (18.*a*) intra-orally while it is secured in place onto the implant, following the same steps as per natural teeth preparation. Following this, the dentist takes an abutment level impression of the modified abutment (18.*e*) and the fabricated in the lab or in-office temporary prosthesis (18.*d*) can then be cemented directly onto the modified abutment (18.*e*) with the use of cement or other bonding agents (18.*h*). Alternatively, if the dentist has available in the dentist's office a digital scanner (17.*e*) then after the abutment is modified (18.*e*) he can take a digital impression with the digital scanner that can be used for the fabrication of a temporary prosthesis (18.*d*) that fits onto the modified abutment (18.*h*) by utilization of a cad-cam machine.

An additional exemplary application of the custom potentially modifiable impression posts with different degrees of angulations towards the vertical (3.*f*) is the following. If at any time point of treatment the dentist wishes to restore the implant with a temporary prosthesis after the impression taking with the use of the custom, modifiable impression post (FIGS. 14A-14D, 15A-15E, 16A-16E) and the fabrication of the working cast (17.*l*) on to the latter, the dental technician (e.g., dentist or technician) can separate by abrasion (17.*a*) the polymorphic part (17.*d*) from the rest of the body of the impression post (17.*b*) modifying it this way to a temporary abutment (17.*k*) that can support a temporary prosthesis (18.*d*) fabricated by the dental technician. This application is very useful in cases where multiple implants have been placed in edentulous jaw and the fabrication of a temporary prosthesis supported by the total number of implants is desired (FIGS. 21A-21D). In these cases the supra-gingival part of the modified impression post must be prepped in a way that the sidewalls of all of the modified impression posts are parallel to each other (21.*l*). This process is difficult to achieve intra-orally by the dentist. In contrast, if the impression is taken onto the working cast (21.*e*) the dental technician modifies the custom impression posts to custom abutments by separation and removal of their polymorphic part (FIGS. 17B, 21A-21D) and then, with the use of a parallel graph machinery, the technician can prep properly the supra-gingival sidewalls of the modified impression posts (21.*m*). The parallel preparation of the modified impression posts allows the fabrication of a prosthesis (21.*z*) that can fit accurately and passively as one piece onto the total number of the modified impression posts (21.*k*). Alternatively, the dental technician can take a digital impression of the working cast (21.*m*) with the modified impression posts with a digital scanner and this digital impression can be used for the fabrication of a temporary prosthesis by utilization of a cad-cam machine (FIG. 17C).

To potentially enhance the understanding of all of the above we present the following examples.

Example 1

In a first example the edentulous space that has been generated from a missing tooth has received an implant that, due to bone width missing from the facial aspect of the alveolar ridge, has been placed by the surgeon with an angulation of twenty degrees towards the longitudinal axis of the final prosthesis that the implant will receive (FIGS. 14A-14D). After the implant placement the surgeon couples with the implant a custom abutment with twenty degrees angulations (14.*a*) with a short retention screw (9.*a*). The custom abutment utilized has dimensions that correspond to the available prosthetic space. Specifically the custom abutment is located in the edentulous space in a way that its outer borders are within the line borders of the future prosthesis (20.*z*) without expanding out of this borders at any point and its custom body has an angulation that is parallel to the one of the longitudinal axis of the final prosthesis (FIGS. 14A-14D, 20A-20B). Following this, the surgeon sutures the gingival around the custom abutment (14.*a*). After the period of implant osseointegration is complete the prosthetic rehabilitation takes place. Specifically, the custom abutment (14.*a*) is uncoupled from the implant, revealing a gingival emergence profile developed by the custom abutment (14.*a*) around the implant platform (14.*b*) that has oval shape, gradually expandable laterally upwards and with angulations that is parallel to the emergence profile of the final prosthesis that the implant will receive. At this stage a custom impression post, with corresponding shape, size and angulations to the custom abutment used, is installed on the implant (14.*e*). The proximal open bore (14.*d*) of the impression post is sealed by the isolation cap and following the dentist creates an artificial groove (15.*b*) with abrasion (15.*a*) on one of the supra-gingival surfaces of the custom body of the impression post (3.*b*). Following this, the dentist takes the impression 15.*e* with the use of a closed tray (15.*g*) filled in with impression material (15.*d*, 15.*z*). The impression (16.*b*) has generated within it a negative replication (16.*a*) of the impression post (14.*e*), the teeth and the alveolar process (16.*b*). Following this, the dentist removes the isolation cap and then unscrews the retention screw and removes the impression post from the mouth. He then couples to the implant once again the custom abutment and following he couples the impression post to an implant analog with corresponding type and size to the implant prosthetic connection and installs the system impression post (16.k)-implant analog (16.i) into the impression post negative replication in the impression (16.l), orienting himself by the negative replication of the artificial groove (15.b). Following this, the dental technician introduces gingival mask elastomeric material around the part of the impression post presenting free of impression material (16.k) into the impression (16.l). Then he pours the impression with gypsum and after the latter is set he removes the impression from the gypsum cast that is fabricated. At this stage the dental technician uncouples the impression post (16.h) from the implant analog (16.z) that is securely embedded within the gypsum and he has now available a working cast (16.m) that represents the exact replication of the patient's jaw and teeth, the location of the implant platform in the jaw, the orientation of the implant prosthetic connection and the gingival emergence profile present around the implant platform as this has been generated by the custom abutment (14.b) in the mouth and it is recreated on the working cast by the gingival mask. The dental technician now utilizes the working cast in order to fabricate the final implant prosthesis (19.e), which has an emergence profile (19.u) that follows the developed gingival emergence profile (19.i). Following this, the dentist uncouples the custom abutment (14.a) from the implant in the mouth and installs the final implant prosthesis (20.b) onto the implant (20.g) in the mouth (20.d).

Example 2

In a second example (FIGS. 18A-18C) a custom abutment (18.b) is coupled with an implant in the mouth (18.g) and the prosthetic rehabilitation of the implant with a temporary prosthesis (18.d) is desired, in order for a transitional loading of the implant to be achieved, before the implant receives its final prosthesis. At this stage the supra-gingival portion of the custom abutment (18.b) is prepped by abrasion from the dentist (18.a), following the same principles as per natural teeth preparation. Thus, the custom modified by abrading abutment now has a shape similar to that of a prepped tooth with supra-gingival prosthetic borders (18.e), while the emergence profile (14.b) of the modified abutment (18.b) remains intact since any abrading of the abutment takes place only supra-gingivally. Following this, the dentist takes an abutment level impression of the modified abutment (18.e) with the same principles as per natural abutment teeth impression. The impression is then sent to the dental technician, who pours it to gypsum and fabricates a temporary prosthesis (18.d) that fits onto the modified abutment (18.e) with the same principles as per temporary prosthesis fitting on a natural prepped tooth. Specifically, the dentist cements the temporary prosthesis (18.d) on to the modified abutment (18.e) in the mouth with the use of cement or other bonding agents (18.h). When the dentist is ready to proceed with the final restoration (20.z) he can either de-cement the temporary prosthesis (18.h) from the modified abutment (18.e) and following uncouple the modified abutment from the implant, or he can uncouple the system modified abutment-temporary prosthesis as one piece (20.b) from the implant. The second can be achieved by abrading the temporary prosthesis and revealing the proximal open bore of the hollow channel of the modified abutment (18.b), making possible access to the retention screw (20.a) so that it can be unscrewed from the implant. The rest of the steps for the impression process with the use of custom impression post (14.e), the working cast fabrication and the fabrication of the final implant prosthesis (20.z) are similar to the ones described previously in the first example.

Example 3

In a third example (FIGS. 21A-21D) in an edentulous jaw two implants have been placed on the right side, which present fifteen degree angulations towards the longitudinal axis of the final prosthesis, while at the left side two implants have been placed which present twenty-five degree angulations towards the longitudinal axis of the final prosthesis. Two custom abutments of fifteen degrees angulations (21.b, 21.bb) are coupled with the two implants of the right side and two custom abutments of twenty-five degree angulations (21.a, 21.aa) are coupled with the two implants of the left side. After the osseointegration period is passed the angulated custom abutments are uncoupled from the implants and four angulated custom impression posts, with corresponding to the abutments angulations and dimensions, replace them (21.d, 21.dd, 21.g, 21.gg). Following this, the dentist takes an implant level impression following the same steps as they have been previously described in the first example. The dental technician pours the impression in gypsum and fabricates the working cast in a similar way as previously described and then he separates and removes by abrasion the polymorphic part of the impression posts (17.d) modifying this way the impression posts into modified angulated abutments.

Following this, the dentist preps the supra-gingival portion of the abutments with the assistance of specialized machinery in a way that all the sidewalls of all of the modified abutments are parallel to each other (21.m, 21.i). Following this, the dentist fabricates a temporary prosthesis (21.z) that is supported by the modified abutments (21.i) and which has a pathway of fit onto the latter that is determined by the parallel inclination of the supra-gingival sidewalls of the modified abutments. Following this, the dentist uncouples from the implants the custom abutments (21.a, 21.b) and replaces them with the abutments modified by the dental technician (21.i) that have been generated by the modification on the working cast of the custom impression posts (21.g, 21.d). Following this, the dentist cements onto the supra-gingival portion of the modified abutments the one-piece temporary prosthesis (21.z). When the dentist wishes to proceed with the installation of the final prosthesis, the dentist then de-cements the temporary prosthesis from the modified abutments and following that the dentist replaces the latter with the final abutments that receive the final prosthesis (21.k).

Example 4

For this example, embodiments are provided to illustrate exemplary aspects of the invention.

1. A mold (1.a, 22.a) that comprises: a base (1.g, 22.b) that on its upper surface (22.h) has sockets (1.n, 22.z) of different geometrical shapes and dimensions (1.d, FIG. 1F1, 1.e, FIG. 1F2, 1.z, FIG. 1F3, 1.h, FIG. 1F4, 1.f, 1.i, FIG. 1F6, 1.k, FIG. 1F7) that resemble implant prosthetic connections (4.g) of different types and sizes (1.d, FIG. 1F1, 1.e, FIG. 1F2, 1.z, FIG. 1F3, 1.h, FIG. 1F4, 1.f, 1.i, FIG. 1F6, 1.k, FIG. 1F7) and which have a threaded blind bore on their base (24.j) and they are oriented along with their blind bore (24.j) in various degrees of angulations (including zero degrees) toward the vertical (24.aa, 10.aa, 11.aa) and a superstructure (1.m, 22.e) coupling with the upper surface of the base (1.g, 22.b), with open wells (1.l, 22.g, 24.b) that are oriented parallel with the vertical (FIGS. 24A-24B, FIG. 1E section A-A) and which have a custom design (FIGS. 24A-24B) and allow the introduction within them of abutments (7.r, 4.a, 4.z, 5.a, 5.b)

and impression posts (8.*k*, 4.*b*, 4.*h*, 5.*g*, 5.*b*) of dental implants (4.*e*) with various degrees of angulations toward the vertical and their prosthetic connections (4.*g*) interconnect and couple thread with the corresponding dimensions and angulations of prosthetic connections (1.*n*, 22.*z*) of the base (1.*g*, 22.*b*) with a long or short retention screw (9.*e*, 10.*u*, 11.*z*) which is plastic, or metallic, or ceramic, and they function as cores for the fabrication of one-piece, custom potentially modifiable abutments and impression posts (2.*r*, 10.*h*, 3.*f*, 11.*h*) with various degrees of angulations or they (30.*b*, 30.*d*) receive an abutment cap (30.*aa*), or an impression abutment cap (30.*ga*), that snaps on (31.*e*, 31.*z*) their pillar part (30.*a*, 30.*g*), and they function as cores (30.*b*, 30.*d*) for the fabrication of two pieces, custom potentially modifiable abutments and impression posts respectively (30.*e*, 30.*z*) with various degrees of angulations and their customization is achieved with the introduction of a curable biocompatible material (12.*bl*, 12.*al*) in the outlined space (10.*j*, 11.*j*) present between the pillar part of the abutment (10.*n*), or the pillar of the impression post (11.*n*), or of the abutment cap (30.*aa*), or of the pillar impression abutment cap (30.*ia*), that is located within the side borders of the upper part (24.*l*) of the open wells (24.*b*) of the superstructure (24.*a*, 24.*p*) and the inside walls (10.*m*, 11.*m*, 24.*m*) of these wells (24.*b*), subsequent curing and setting of the biocompatible material (13.*a*, 13.*b*) and integration of the latter with them (2.*b*, 2.*e*, 30.*ha*, 3.*b*, 3.*h*, 30.*ua*), and which custom abutments (2.*r*, 30.*e*) and custom impression posts (3.*f*, 30.*z*) after their uncoupling (10.*h*, 30.*e*, 11.*h*, 30.*z*) from the mold (1.*a*, 22.*a*), with the uncoupling of the retention screw (10.*d*, 10.*u*, 11.*d*, 11.*u*) they are coupled into the socket (23.*g*) of a grip handle (23.*d*) with a short retention screw (23.*a*) and receive abrasion and polishing with polishing brush and paste (23.*z*, 23.*u*) on their customized part (FIG. 23A-23C), before they get disinfected, sterilized and are used clinically.

In preferred versions of embodiments of molds described herein, including but not limited to the mold of embodiment 1 of this example, (a) one version of such molds provides for only straight custom and modifiable abutments and/or impression posts that have no angulation from the vertical, (b) another version of such molds provides for only non-straight custom and modifiable abutments and/or impression posts that have an angulation from the vertical that is greater than zero, and (c) still another version of such molds provides for a mixture of at least one straight custom and modifiable abutment and/or impression post that each have no angulation from the vertical, and at least one non-straight custom and modifiable abutment and/or impression post that each have an angulation from the vertical that is greater than zero. In the embodiments of molds described herein, including but not limited to the mold of embodiment 1 of this example, the molds can provide for (a) only custom and modifiable abutments, (b) only custom and modifiable impression posts, or (b) a mixture of at least one custom and modifiable abutment and at least one custom and modifiable impression post.

2. A mold (1.*a*, 22.*a*) as referred in embodiment 1 of this example, where the base of the mold (1.*g*, 22.*b*) is made out of metal, or ceramic and has on its upper surface (22.*h*) one or more sockets of the same or different geometrical shapes and dimensions (1.*n*, 22.*z*) that resemble prosthetic implant connections (4.*g*) of the same or different type and size (1.*d*, 1.*e*, 1.*z*, 1.*h*, 1.*u*, 1.*i*, 1.*k*, FIGS. 1F1-1F7) and with the same or different angulations towards the vertical (1.*aa*, 24.*aa*) that vary from one to forty-five degrees and have a threaded blind bore at their base (24.*j*) which presents the same angulations with them and allow through a retention screw (9.*e*) their threaded coupling with a corresponding in angulations toward the vertical, prosthetic connection of an angulated abutment (7.*j*), and/or of an angulated impression post (8.*o*) of dental implants (4.*e*) which (7.*j*, 8.*o*) has a corresponding angulation (10.*aa*, 12.*bb*) and is of the same or different type and/or size (1.*d*, 1.*e*, 1.*z*, 1.*h*, 1.*u*, 1.*i*, 1.*k*, FIGS. 1F1-1F7).

3. A mold (1.*a*, 22.*a*) as shown in embodiment 1 of this example, where the base of the mold (1.*g*, 22.*b*) on its upper surface (22.*h*) incorporates along with the angulated sockets (24.*n*), or by themselves, sockets (1.*n*, 22.*z*) of different geometrical shapes and dimensions (1.*d*, 1.*e*, 1.*z*, 1.*h*, 1.*u*, 1.*i*, 1.*k*, FIGS. 1F1-1F7) that present a zero degree angulation toward the vertical (24.*aa*) and incorporate straight abutments (25.*a*) and straight, open and closed tray, impression posts (25.*b*, 25.*g*) aiming for the fabrication of straight, custom, potentially modifiable abutments (25.*d*) and impression posts (25.*e*, 25.*z*).

4. A mold (1.*a*, 22.*a*) as shown in embodiment 1 of this example, where the superstructure of the mold (1.*m*, 22.*e*) is made out of elastomeric material, or metal, or ceramic, or acrylic, or plastic, or any other material that can be highly polished and allow the easy decoupling of the fabricated custom abutment (2.*r*, 10.*h*) and, or impression post (3.*f*, 11.*h*) and it is integrated on the base (1.*g*, 22.*b*) with mechanical and, or chemical connection. The superstructure (1.*m*, 22.*e*) has open wells (1.*l*, 22.*g*, 24.*b*) with parallel orientation towards the vertical (24.*aa*) that to the their distal, meaning bottom end (1.*r*), towards the base of the mold (1.*g*, 24.*r*), couples precisely the implant prosthetic connection of the base of the mold (1.*n*, 22.*z*, 24.*n*), while their proximal, meaning top end (24.*k*), is open. Every well (1.*l*, 22.*g*, 24.*b*) comprises of two parts as one piece. The first part (24.*h*) is towards the distal and is located in continuation of the implant prosthetic connection of the base (24.*n*) and it comprises of the negative replication of the upper surface of the shoulder (7.*e*, 8.*s*) of an angulated and, or straight abutment (7.*r*, 25.*a*) and, or impression post (8.*k*, 25.*b*, 25.*g*) and it has a minimum diameter that is equal to or smaller than the maximum diameter of their shoulder (7.*n*, 8.*p*). The second part (24.*l*) comprises a continuation of the first part (24.*h*) upwards, and comprises the negative replication of the custom body (2.*j*, 2.*e*, 3.*s*, 3.*h*) of the corresponding per case, custom potentially modifiable abutment (2.*r*, 25.*d*, 30.*e*) and impression post (3.*r*, 25.*e*, 25.*z*, 30.*z*), which corresponds to an emergence profile of oval or cylindrical shape, gradually expandable laterally, from the base upwards, and with symmetrical cross section and regular surfaces (FIGS. 2A-2D, 3A-3D).

5. A mold (1.*a*, 22.*a*) as shown in embodiment 1 of this example, where the second part (24.*l*) of the superstructure of the mold (1.*m*, 22.*e*), comprises the negative replication of the custom body of the corresponding per case, custom potentially modifiable abutment (29.*a*, 29.*b*, 29.*g*, 29.*d*) and impression post (29.*e*, 29.*z*, 29.*h*, 29.*u*), which corresponds to an emergence profile of oval or cylindrical shape, gradually expandable laterally, from the base upwards, and with asymmetrical cross section and regular surfaces (FIG. 29A-29H).

6. A mold (1.*a*) as shown in embodiment 1 of this example, where the base (1.*g*) and the superstructure (1.*m*) are one piece made out of metal, or ceramic, or plastic, or elastomeric material, or a combination of those materials.

7. A mold (22.*a*) as shown in embodiment 1 of this example, where the base (22.*b*) comprises of two parts threaded coupled to each other (22.*d*, 22.*k*), and which hold the superstructure (22.e) in between them in a stable position (22.a). The bottom part of the base (22.k) has an external thread on its upper part (22.u) and the top part (22.d) has an internal thread on its bottom part (22.i). The two parts (22.d, 22.k) through these threaded parts (22.i, 22.u) couple thread together accurately, keeping the superstructure of the mold (22.e) immobile in a stable position in between them and, or they uncouple allowing the free movement of the superstructure of the mold (22.e).

8. A set that will be used for the fabrication of one-piece (10.h, 2.r), or two-piece (30.e), custom, potentially modifiable abutments and one-piece (11.h, 3.f), or two-piece (30.z), custom, potentially modifiable impression posts, with various degrees of angulations toward the vertical, where the set includes:

A mold (1.a, 22.a) as shown in embodiment 1 of this example.

Abutments (7.r, 5.a, 5.b, 4.a, 4.z) and impression posts (8.k, 5.g, 5.d, 4.b, 4.h) of dental implants (4.e) with various degrees of angulations toward the vertical, as referred in embodiment 1 of this example, so that they function as cores around which the one-piece (2.r) custom, potentially modifiable abutments (FIG. 2D section A-A) and the one-piece (3.f) custom, potentially modifiable impression post (FIG. 3D section A-A) with various degrees of angulations respectively are fabricated. Those abutments (7.r, 5.a, 5.b, 4.a, 4.z) comprises three parts (7.j, 7.n, 7.m), while those impression posts (8.k, 5.g, 5.d, 4.b, 4.h) comprises four parts (8.o, 8.p, 8.z, 8.u). The first part of the abutments (7.r, 5.a, 5.b, 4.a, 4.z) and of the impression posts (8.k, 5.g, 5.d, 4.b, 4.h) is a prosthetic connection (7.j, 8.o) that is a conical (4.i, 4.l), or polyhedron (4.u, 4.k) post that is the exact negative replication of the prosthetic connection of an implant (4.g). Their prosthetic connection (7.j, 7.o) interconnects and couple locks to the prosthetic connection (1.n, 22.z, 24.n) of the base (1.g, 22.b, 24.r) of the mold (1.a, 22.a) and presents angulations (10.aa, 11.aa) similar to it (10.k, 11.k) towards the vertical (FIGS. 10A-10E, 11A-11E). Their second part is a shoulder which is a cylinder of variable section (7.n, 8.p) that fits to the bottom part of the well of the superstructure of the mold (24.h) and isolates it from the top part of the well (24.l) through the absolute peripheral fit of its upper surface (7.e, 8.s) with the upper border of the bottom part of the well (24.h). The shoulder (7.n, 8.p) has sidewalls (7.z, 8.r) that are straight (6.a, 6.d), or convex (6.g, 6.z), or concave (6.b, 6.e), or curved (FIGS. 7A-7D, 8E section A-A). Their third part is a pillar (7.m, 8.z) that has cylindrical (FIGS. 5A-5D, 7A-7D, 8A-8E), or polyhedron shape (FIGS. 4A-4D) with flat (4.m) or flat and curved surfaces (31.eb), where the flat surfaces (4.m, 4.n) are fully corresponded in space with the flat surfaces of the prosthetic connection of the abutment (4.u) and of the impression post (4.k), while the curved surfaces have a vertical and or horizontal orientation (31.eb). The pillar of the abutment (7.m, 10.n) and of the impression post (8.z, 11.n) is located within the side borders (10.m, 11.m, 24.m) of the upper part of the well of the superstructure of the mold (24.l) with a parallel orientation towards the vertical (10.aa, 11.aa). The impression posts (8.k) have a fourth part that we call polymorphic (8.u), as an extension of the pillar (8.z) upwards, with a design that creates a negative replication into the impression material (16.a), that allows their reproducible placement in the same position within the latter (FIGS. 16A-16E). The polymorphic part (8.u) is a cylinder with variable section that has three vertical, curved surfaces (8.t) that intercept from each other through three vertical, concave surfaces of smaller radius (8.x). Each of the three curved surfaces (8.t) of the polymorphic part (8.u) is divided into two convex parts, upper (8.ta) and lower (8.tb) from a horizontal, concave surface of smaller radius (8.y) that is located in the middle of them. The areas of connection of the different in shape surfaces (8.va, 8.vb) are curved without any acute angles. Each of the convex surfaces (8.ta, 8.tb) of the polymorphic part (8.u) presents curved sidewalls (8.th, 8.tz). The maximum diameter of the polymorphic part (8.u) is smaller, or equal, or bigger than the diameter of the base of the shoulder of the impression post (8.d). The horizontal concave surface (8.y, 8.ub) has a diameter that is equal to the diameter of the pillar (8.z). The polymorphic part (8.u) as a whole has smooth surface and its height varies from five to twenty millimeters. The polymorphic part (8.u) in cross-section (FIG. 8E section A-A) presents a curved surface that is divided into two equal convex parts, upper (8.ta) and lower (8.td) through a concave surface (8.yb). The polymorphic part (8.u) horizontal section (FIG. 8E section B-B) presents a trihedral shape that resembles a propeller with three wings, of which the outer surface (8.te) is convex, while the two side walls (8.th, 8.tz) are concave. Each of the vertical curved surfaces of the polymorphic part (8.t, 4.j) is fully corresponded in space with one of the seats of the prosthetic connections of the impression post (4.k). The polymorphic part (8.u, 11.o) is parallel to the vertical when the impression post (8.k) is connected through its prosthetic connection (11.i) with the prosthetic connection of the base of the mold (11.k). The abutments (7.r) and the impression posts (8.k) have a hollow channel (7.u, 8.a) that allows the free pass of a short (9.a) or a long (9.e) retention screw the thread (9.u) of which couples with thread of the blind bore of the socket of the base of the mold (24.j) aiming at their coupling and retention to the prosthetic connection of the base of the mold (1.n, 22.z, 24.n). The hollow channel (7.u, 8.a) is descriptively divided in two parts, an upper (7.i, 8.abe) and a lower (7.h, 8.abd). The diameter of the upper part (7.i, 8.abe) is larger than the diameter of the bottom part (7.h, 8.abd). The diameter of the upper part (7.i, 8.abe) is larger than the maximum diameter of a short retention screw (9.a) and of the diameter of the threaded portion (9.u) of a long retention screw (9.e) and at the same time smaller than the diameter of the head of the latter (9.h). The diameter of the lower part (7.h, 8.abd) is larger than that of the threaded portion (9.z, 9.u) and at the same time smaller than that of the head of the short (9.d) and long (9.h) retention screw. The abutment (7.r) presents a hollow channel (7.u) for the entrance of the retention screw (9.a, 9.e) of which the upper open bore (7.a) is located on a side wall of the pillar (7.m), while the bottom open bore (7.p) of the hollow channel (7.u) is located on the bottom surface of the prosthetic connection of the abutment (7.l). The impression post (8.k) presents a hollow channel (8.a) for the entrance of the retention screw (9.a, 9.e) of which the upper open bore (8.b) is located on a side wall of the pillar (8.z), or of the polymorphic part (8.u), or of both (8.z, 8.u) of the aforementioned, while the bottom open bore of the hollow channel (8.*ab*) is located on the bottom surface of the prosthetic connection of the impression post (8.*o*).

A short (9.*a*) or long (9.*e*) retention screw, made out of metal, or plastic, or ceramic material, as shown in embodiment 1 of this example, that allows the coupling and retention of the abutment (7.*r*), or of the impression post (8.*k*) into its functional position inside the mold (1.*a*, 22.*a*) and, or at the same time isolates its hollow channel (7.*u*, 8.*a*) keeping it free of biocompatible material (12.*al*, 12.*bl*) and allowing after it is removed (9.*e*) the free entrance and exit of the retention screw (9.*a*, 9.*e*) aiming at the trouble free coupling of the custom, abutment (2.*r*) and impression post (3.*f*) with the prosthetic connection of an implant (4.*g*) with the use of this retention screw (9.*a*, 9.*e*).

An abutment cap (30.*aa*) that couples onto the pillar of the abutment (30.*ab*) through a blind bore which has a length equal to the height of the pillar (30.*ab*), that has on its bottom part aiming to the establishment of a two-piece (30.*aa*, 30.*a*) core (30.*b*) that is used for the fabrication of a custom potentially modifiable two-piece (30.*ha*, 30.*h*) abutment (30.*e*). The abutment cap (30.*aa*) is a pillar with stable or variable section and regular surfaces that are smooth or rough or smooth and rough. The pillar (30.*aa*) has a shape that is cylindrical, or cylindrical with one flat seat or polyhedron, where the flat surface or surfaces are fully corresponded in space with one or more of the seats of the prosthetic connection (4.*u*) of the abutment (30.*a*). The abutment cap (30.*aa*) after it is coupled with the pillar of the abutment (30.*ab*) extends in height from the upper surface of the abutment shoulder (2.*z*) to the free end of the abutment pillar (2.*d*, 30.*ab*) or further than the latter. The internal surface of the abutment cap (30.*aa*) has a shape that replicates the exact negative replication (31.*e*, 31.*z*) of the external surface and or part of the hollow channel of the pillar (30.*ab*) of an abutment (30.*a*) that has a pillar (30.*ab*) which around its body in the part located close to its shoulder (31.*e*, 31.*z*) has a concave groove with curved borders (31.*eb*) that is oriented vertically towards the pillar (30.*ab*), this groove (31.*eb*) allows her snap on connection (31.*za*) with its negative replication (31.*ea*) present in the inner surface of the corresponding bottom part of the abutment cap (30.*aa*) and with this way the complete, stable, precise and snap on coupling of the two pieces (31.*z*) to one piece (30.*b*) is allowed.

An impression abutment cap (30.*ga*) that couples onto the pillar (30.*gb*) of the abutment (30.*g*) through the blind bore that has on its bottom end, aiming to the establishment of a two-piece (30.*ga*, 30.*g*) core (30.*d*) is used for the fabrication of a custom potentially modifiable two-piece (30.*ua*, 30.*u*) impression post (30.*z*). The impression abutment cap (30.*ga*) is a post with variable section that descriptively is divided in two parts (30.*ia*, 30.*ib*) as one piece (30.*ga*). The first part (30.*ia*) is a pillar with a blind bore that has a length equal to the height of the pillar (30.*ia*) on its bottom part and has a shape that is cylindrical, or cylindrical with one flat seat, or polyhedron where the flat surface or surfaces are fully corresponded in space with one or more seats of the prosthetic connection (4.*u*) of the abutment (30.*g*). The pillar (30.*ia*) has a stable, or variable section and regular, or irregular surface that is smooth or rough while its internal surface has a shape that replicates the exact negative replication (31.*e*, 31.*z*) of the external surface and or part of the hollow channel of the pillar (30.*gb*) of an abutment (30.*g*) of which the pillar moreover has a concave groove with curved borders (31.*eb*), oriented vertically towards the pillar (31.*gb*), around its body in a part (31.*e*) of it that is located close to its shoulder (2.*z*) and which groove (31.*eb*) allows the complete, stable, precise snap on coupling of the two pieces (31.*ea*, 31.*eb*) to each other (31.*za*) as one piece (31.*z*, 30.*d*). The second part of the impression abutment cap (30.*ib*) is a solid cylinder or variable section with three vertical curved surfaces (30.*ih*) that are distinguished between each other from three vertical convex surfaces of smaller radius (30.*id*). The vertical curved (30.*ih*) and convex (30.*id*) surfaces are all or some of them fully corresponding in space with all or some of the flat surfaces (4.*u*) of the prosthetic connection (7.*j*) of the abutment (7.*r*, 30.*g*). Each one of the three vertical curved surfaces of the cylinder (30.*ih*) is divided in two convex parts, upper (30.*ie*) and lower (30.*iz*) from a horizontal convex surface of smaller radius (30.*ig*) which is located at their mid point (FIG. 30A-30L). The maximum diameter of the cylinder (30.*ib*) is smaller or equal or larger than the diameter of the base of the abutment shoulder (7.*o*). The horizontal convex surface of smaller radius (30.*ig*) has a diameter that is smaller or equal or larger than the one of the pillar (30.*ia*). The second part of the impression abutment cap (30.*ib*) as a whole has smooth or rough surface and its height may vary from three to twenty millimeters. The impression abutment cap (30.*ga*) has the same angulations toward the vertical with the pillar (30.*gb*) part of the abutment (30.*g*). The impression abutment cap (30.*ga*) and the pillar (30.*gb*) of the abutment (30.*g*) are oriented parallel to the vertical when the system abutment-impression abutment cap (30.*d*) is coupled to the prosthetic connection of the base of the mold (31.*d*).

A curable biocompatible material (12.*al*, 12.*bl*) as shown in embodiment 1 of this example, with radio opaque properties and scan-able potential from a digital scanner (17.*e*) that can be abraded and polished (23.*z*, 23.*u*) and is used for the filling of the space (10.*j*, 11.*j*) between the internal walls (10.*m*, 11.*m*, 24.*m*) of the upper part of the well of the superstructure of the mold (24.*l*) and the pillar of the abutment (10.*n*) or the pillar of the impression post (11.*n*) or of the abutment cap (30.*aa*) or of the pillar (30.*ia*) of the impression abutment cap (30.*ga*) aiming to the fabrication of the body of the custom potentially modifiable abutment (2.*b*, 10.*z*, 30.*ha*) and custom potentially modifiable impression post (3.*b*, 11.*z*, 30.*ua*), respectively.

Brushes (23.*z*, 23.*u*) and paste for abrasion and polishing as shown in embodiment 1 of this example, that are used for the abrasion and polishing of the body of the custom modifiable abutments (23.*e*) and of the custom potentially modifiable impression posts (23.*h*).

A retention handle (23.*d*) as shown in embodiment 1 of this example, which couples with the custom abutment (23.*e*) and the custom impression post (23.*h*) with a short or long retention screw (23.*a*) aiming at the easy abrasion and polishing of their body. The retention handle (23.*d*) is a solid cylinder that has a flat surface on each of its two ends this flat surface (23.*i*) has a diameter that is larger than the diameter of the base of the shoulder of the custom abutment (7.*o*) and of the impression post (8.*d*). The flat surface (23.*i*) has one or more sockets (23.*g*) with shape and dimensions corresponding to the ones of the prosthetic connections of the base of the mold (1.d, 1.e, 1.z, 1.h, 1.u, 1.i, 1.k, FIGS. 1F1-1F7). These sockets (23.g) at their base have a blind threaded bore that allows the threaded coupling of a retention screw (23.a) of the custom abutment (23.e) and impression post (23.h) aiming to the secure connection and retention of the latter (23.e, 23.h) onto the handle (23.d). This handle (23.d) is metallic or ceramic or plastic or a combination of the aforementioned and its length varies from two to twenty centimeters.

9. A method for the fabrication of one-piece custom potentially modifiable abutments (2.r) and custom potentially modifiable one-piece impression posts (3.f) with various degrees of angulations towards the vertical, where the method includes:

The availability and utilization of a mold (1.a, 22.a) as shown in embodiment 1 of this example.

The availability and utilization of an abutment (7.r, 5.a, 5.b, 4.a, 4.z) and impression post (8.k, 5.g, 5.d, 4.b, 4.h) with different degrees of angulations toward the vertical as shown in embodiment 1 of this example.

The method further includes the coupling of an abutment (7.r, 5.a, 5.b, 4.a, 4.z) or an impression post (8.k, 5.g, 5.d, 4.b, 4.h) through their prosthetic connection (7.j, 8.o) with a compatible in angulations and fit prosthetic connection of the base of the mold (1.n, 22.z, 24.n) inside the space of the corresponding well of the superstructure of the mold (24.b) with a long retention screw (9.e) that has been coated with a separating or isolating material. The upper surface of the shoulder of the abutment (7.e) and of the impression post (8.s) isolates the bottom part of the well of the superstructure (24.h) from the top part (24.l) thereof. The pillar part of the abutment (7.m) and of the impression post (8.z) is located within the side borders of the upper part of the well of the superstructure (24.m) with an angulations parallel towards the vertical (10.aa, 1.aa) and this way it comprises a core around which the body of the custom abutment (FIG. 2D section A-A) and the custom impression post (FIG. 3D section A-A) is respectively fabricated.

The filling of the space (10.j, 11.j) between the inner walls of the upper part of the well of the superstructure of the mold (10.m, 11.m, 24.m) and the part of the pillar of the abutment (10.n) or of the impression post (11.n) with curable biocompatible material (12.bl, 12.al).

The curing and setting of the biocompatible material (13.a, 13.b) so that the cured material integrated with the pillar of the abutment (10.z) or of the impression post (11.z) will create a custom abutment (2.r, 10.h) or a custom impression post (3.f, 11.h) respectively with an emergence profile that has oval shape gradually expandable laterally upwards with symmetrical or asymmetrical section and regular surfaces in various sizes (FIGS. 2A-2D, 3A-3D, 25A-25F, 29A-29H) that can potentially be modified three dimensionally intra-orally and extra-orally (FIGS. 23A-23C, 18A-18C, 17A-B) and presenting different degrees of angulations toward the vertical.

The uncoupling of the custom abutment (10.h) or impression post (11.h) from the mold (1.a, 22.a) with uncoupling of the long retention screw (10.d, 11.d) is then done.

The coupling of the custom abutment (2.r, 10.h) or impression post (3.f, 11.h) to the socket (23.g) of the upper surface (23.i) of the retention handle (23.d) with a long or short retention screw (23.a) and subsequent abrasion and polishing of its body with brushes and paste for abrasion and polishing (23.z, 23.u).

The uncoupling of the custom abutment (23.e) or impression post (23.h) from the handle (23.d) with removal of the retention screw (23.a) and subsequent disinfection and sterilization of it.

The availability for utilization in clinical practice of one-piece custom potentially modifiable abutments and one-piece custom potentially modifiable impression post with various degrees of angulations towards the vertical (FIGS. 2A-2D, 3A-3D, 25A-25F, 29A-29H).

10. A method for the fabrication of two-piece custom potentially modifiable abutments (30.e) and custom potentially modifiable two-piece impression posts (30.z) with various degrees of angulations towards the vertical, where the method includes:

The availability and utilization of a mold (1.a, 22.a) as shown in embodiment 1 of this example.

The availability and utilization of an abutment (30.a, 30.g, 7.r) with different degrees of angulations toward the vertical (7.aa) as shown in embodiment 1 of this example.

The availability and utilization of an abutment cap (30.aa) and an impression abutment cap (30.ga) as shown in embodiment 1 of this example.

The method further includes the coupling of an abutment (7.r, 31.ab) through its prosthetic connection (7.j) with a compatible (in angulations and fit) prosthetic connection of the base of the mold (1.n, 22.z, 24.n) inside the space of the corresponding well of the superstructure of the mold (24.b) and its stable retention (7.j) in position (24.n) with the use of a short retention screw (9.e). The upper surface of the shoulder of the abutment (7.e) isolates the bottom part of the well of the superstructure (24.h) from the top part thereof (24.l). The pillar part of the abutment is located within the side borders of the upper part of the well of the superstructure (24.m) with angulations parallel toward the vertical (10.aa, 1.aa).

The snap on coupling (31.e, 31.z) of the abutment cap (30.aa) or of the impression abutment cap (30.ya) with the pillar of the abutment (30.ab, 30.gb) so that the pillar (30.ab, 30.ag) as a whole is located within the cap. The snap on coupling (31.ct) is achieved with the coupling of the concave groove (31.eb) present in the lower part of the pillar with the convex extension (31.ea) that is the negative replication of the concave groove (31.eb) and which (31.ea) is present to the corresponding part of the internal surface (31.e) of the abutment cap (30.aa) and of the impression abutment cap (30.ga). The system abutment-abutment cap (30.b) or abutment-abutment impression cap (30.d) is located sideways within the side borders of the open well of the superstructure (31.b, 31.d) and comprises a core around which the body of the custom abutment cap (30.ha) and or custom impression abutment cap (30.ua) is respectively fabricated.

The filling of the space (10.j, 11.j) between the inner walls of the upper part of the well of the superstructure of the mold (10.m, 11.m, 24.m) and the part of the abutment cap or of the impression abutment cap that covers the pillar of the abutment (10.n) with curable biocompatible material (12.bl).

The curing and setting of the biocompatible material (13.b) so that the cured material integrated with the abutment cap (30.ha) or with the impression abutment cap (30.ua) will create a custom abutment cap or a custom impression abutment cap respectively with an emergence profile that has oval shape gradually expandable laterally upwards with symmetrical or asymmetrical section and regular surfaces in various sizes (FIGS. 30A-30L, 29A-29H) that can potentially be modified three dimensionally intra-orally and extra-orally (FIGS. 23A-23H, 18A-18C, 17A-17C).

The uncoupling of the custom abutment cap (30.ha) or of the custom impression abutment cap (30.ua) from the pillar of the abutment (30.hb, 30.ub).

The uncoupling of the abutment (30.h, 30.u) from the mold with removal of the short retention screw (10.d, 11.d).

The coupling of the abutment (30.h, 30.u) to the socket (23.g) of the upper surface (23.i) of the retention handle (23.d) with a short retention screw (23.a) and subsequent coupling of the custom abutment cap (30.ha) or of the custom impression abutment cap (30.ua) onto the pillar of the abutment (30.h, 30.u) and subsequent abrasion and polishing of the custom cap body with brushes and paste for abrasion and polishing (23.z, 23.u).

The uncoupling of the custom abutment cap (30.ha) or of the custom impression abutment cap (30.ua) and subsequent uncoupling of the abutment (30.h, 30.u) from the handle (23.d) with removal of the retention screw (23.a) and subsequent disinfection and sterilization of them before their use in the clinical practice.

The availability for utilization in clinical practice of two-piece custom potentially modifiable abutments (30.e) and two-piece custom potentially modifiable impression posts (30.z) with various degrees of angulations toward the vertical.

11. A method of use of one-piece custom potentially modifiable abutments (2.r) and impression posts (3.f) with various degrees of angulations toward the vertical, where the method comprises:

The availability and utilization of a mold (1.a, 22.u) as shown in embodiment 1 of this example.

The availability and utilization of an abutment (7.r, 5.a, 5.b, 4.a, 4.z) and of an impression post (8.k, 5.g, 5.d, 4.b, 4.h) as shown in embodiment 1 of this example.

The fabrication of a custom potentially modifiable abutment (2.r) and impression post (3.f) as shown in embodiment 1 of this example.

The coupling of the custom potentially modifiable abutment (2.r, 14.a) with an implant (4.e) through the coupling of their prosthetic connections (2.p, 4.g) and their stable threaded retention through a short retention screw (9.a). The prosthetic connection of the custom abutment (2.p) has angulations toward its custom body (2.j) that equals the angulations of the implant long axis toward the long axis of the final prosthesis (FIGS. 20A-20B), aiming to the development of the desired gingival emergence profile (14.b) around the implant platform (4.d) in dimensions, shape and angulations (FIGS. 14A-14D).

After the peri-implant tissue healing process has been completed the subsequent uncoupling of the custom potentially modifiable abutment (2.r, 14.a) from the implant (4.e) and subsequent coupling with the implant (4.e) of a custom potentially modifiable impression post (3.f, 14.e) of the same type, dimensions and angulations with a custom potentially modifiable abutment (2.r, 14.a) that was utilized and subsequent implant impression with closed tray technique (FIGS. 14A-14D, 15A-15E, 16A-16E).

Alternatively, the direct digital impression with scanning of the custom potentially modifiable abutment (2.r, 14.a) with the use of appropriate digital scanner (17.e).

The fabrication of a gypsum working model by the impression (16.b) taken with the use of the custom potentially modifiable impression post (3.f, 14.e), or, alternatively, the generation of a digital working cast from the digital impression taken with the use of the digital scanner (17.e).

The fabrication of the final prosthesis (19.u) by the dental technician onto the gypsum working model (FIGS. 19A-19C) or alternatively the fabrication of the prosthesis by specialized digital cad cam machinery from the digital working cast generated by the digital impression.

Figure 20A:
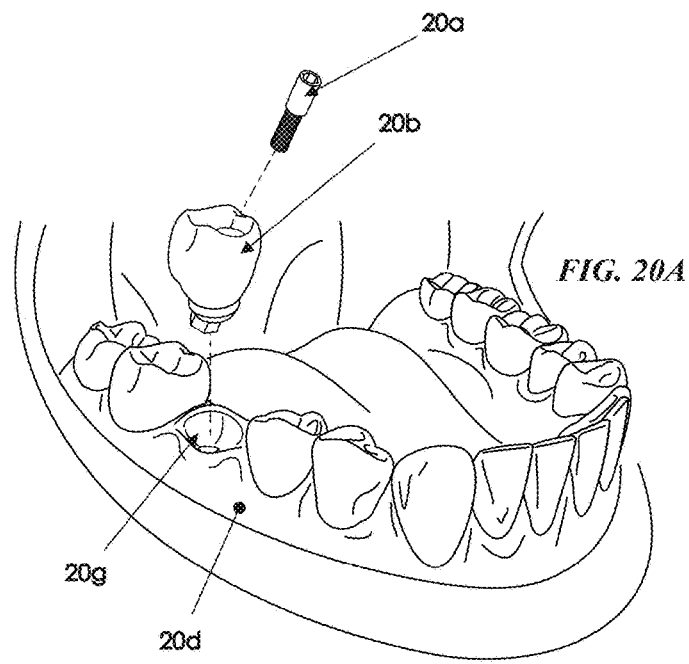
FIGS. 20A-20B are perspective views of aspects of an exemplary process for installation of implants.
Figure 20B:
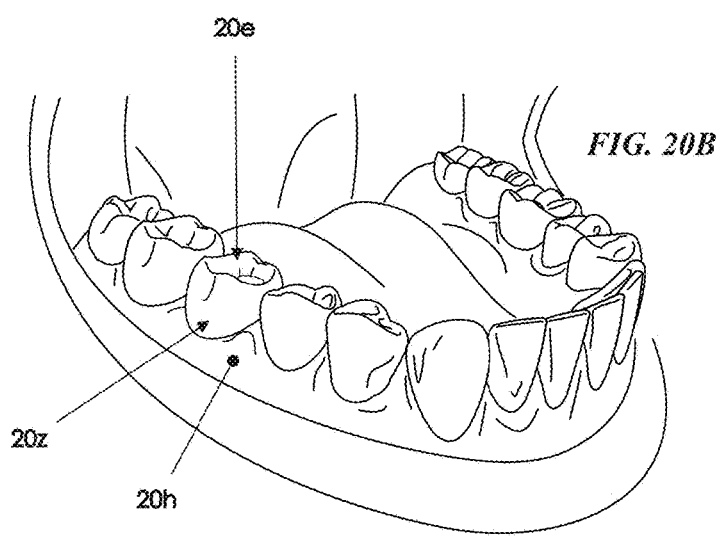
Figures 22A, 22B:
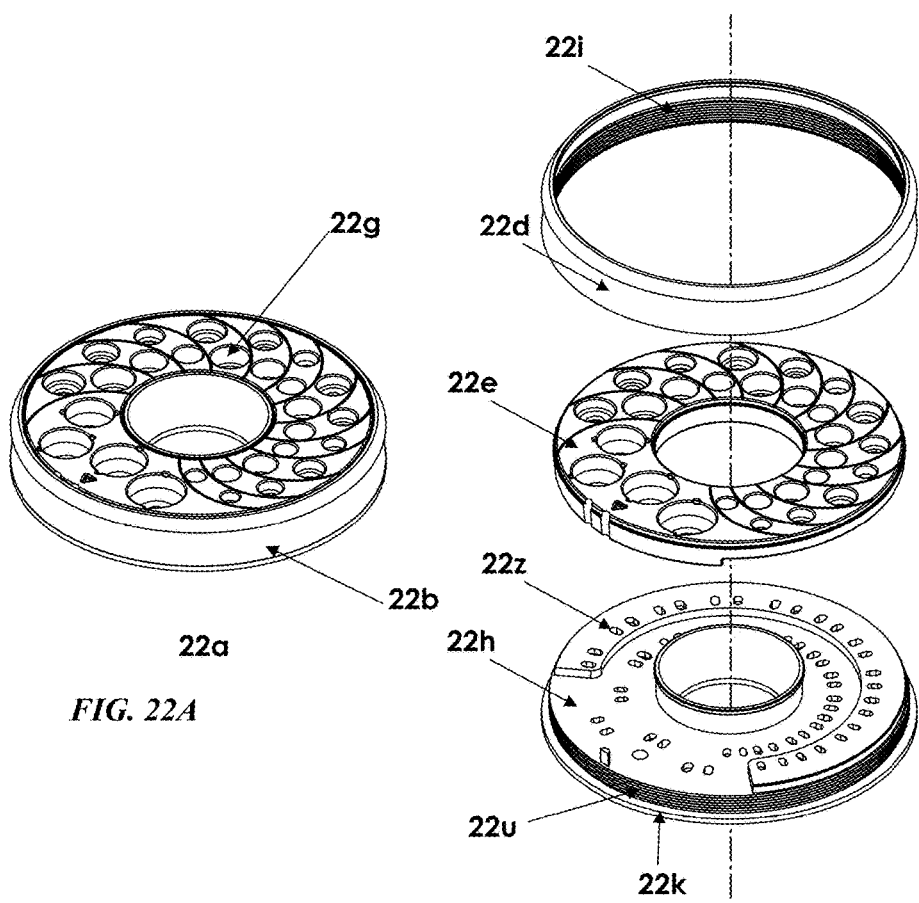
FIG. 22A is a perspective view of an exemplary mold.
FIG. 22B is a perspective view of components of an exemplary mold.

The installation of the final implant prosthesis onto the implant into the mouth (FIGS. 20A-20B).

12. A method of use of the two-piece custom potentially modifiable abutment (30.e) and impression post (30.z) with various degrees of angulations toward the vertical, where the method comprises:

The availability and utilization of a mold (1.a, 22.a) as shown in embodiment 1 of this example.

The availability and utilization of an abutment (7.r, 5.a, 5.b, 4.a, 4.z, 30.a, 30.g) as shown in embodiment 1 of this example.

The availability and utilization of an abutment cap (30.aa) and impression abutment cap (30.ya) as shown in embodiment 1 of this example.

The fabrication of a custom potentially modifiable abutment (30.e) and impression post (30.z) that comprises of an abutment (30.h) and a custom abutment cap (30.ha) as a two-piece system and of an abutment (30.u) and a custom impression abutment cap (30.ua) as a two-piece system respectively as shown in embodiment 1 of this example.

The coupling of the abutment (30.u, 7.r) with an implant (4.e) through the coupling of their prosthetic connections (7.j, 4.g) and their stable threaded retention through a short retention screw (9.a) and the subsequent coupling of the custom abutment cap (30.ha) with the pillar of the abutment (30.hb). The prosthetic connection of the abutment (30.8) has angulations (7.aa) toward the pillar (7.m, 30.ab) of the abutment and toward the custom abutment cap (30.ha) that equals the angulations of the implant long axis towards the final prosthesis long axis (FIGS. 20A-20B), aiming to the development of the desired gingival emergence profile (14.b) around the implant platform (4.d) in dimensions shape and angulations (FIGS. 14A-14D).

The fulfillment of the peri-implant tissue healing process and subsequently the uncoupling of a custom potentially modifiable abutment cap (30.ha) from the abutment pillar (7.m, 30.hb) and the subsequent coupling with the latter (7.m, 30.hb) of a custom impression abutment cap (30.ua) of the same dimensions and size with the custom abutment cap (30.ha) that was utilized and subsequent implant impression with the closed tray impression technique with utilization of two-piece impression post (15.z).

The fabrication of gypsum, working cast (16.m) from the impression (16.b) taken with the use of the custom impression abutment cap (30.ua).

Figures 19A, 19B, 19C:
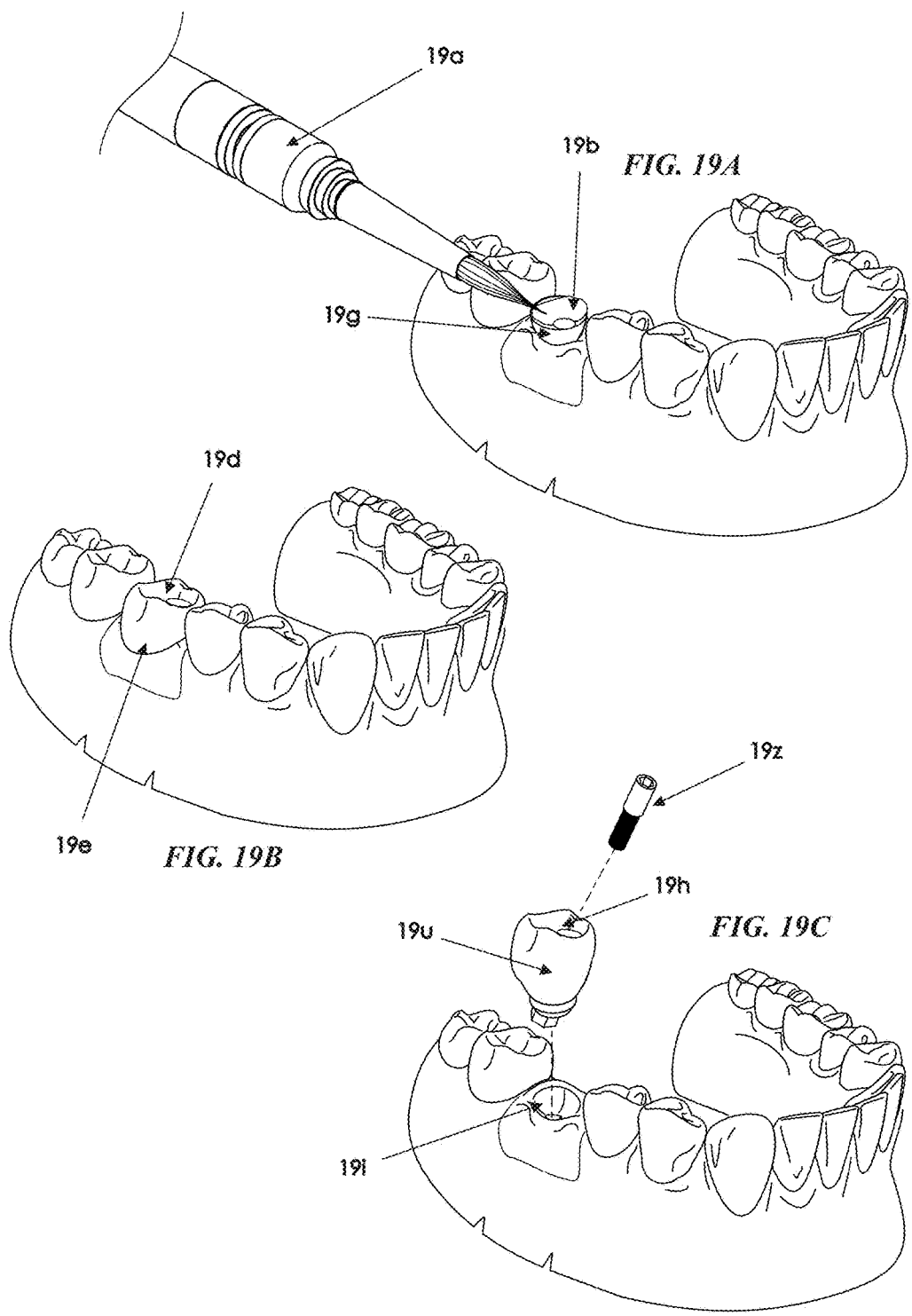
FIGS. 19A-19C are perspective views of an exemplary process for fabricating a prosthesis using a working cast.

The fabrication of the final implant prosthesis (19.u) by the dental technician onto the gypsum-working cast (FIGS. 19A-19C).

The installation of the final implant prosthesis onto the implant into the mouth (FIGS. 20A-20B).

Figure 18A:
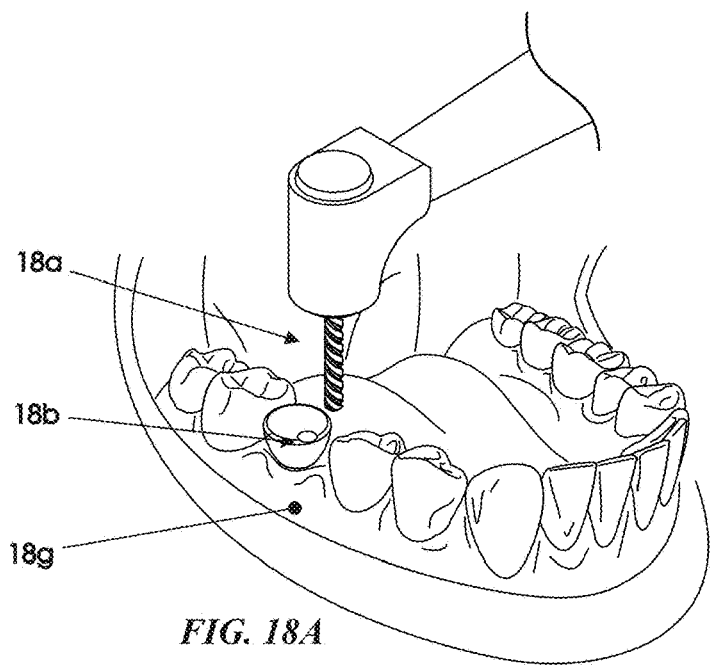
FIGS. 18A-18C are perspective views of an exemplary process for restoring an implant with a temporary prosthesis.
Figure 18B:
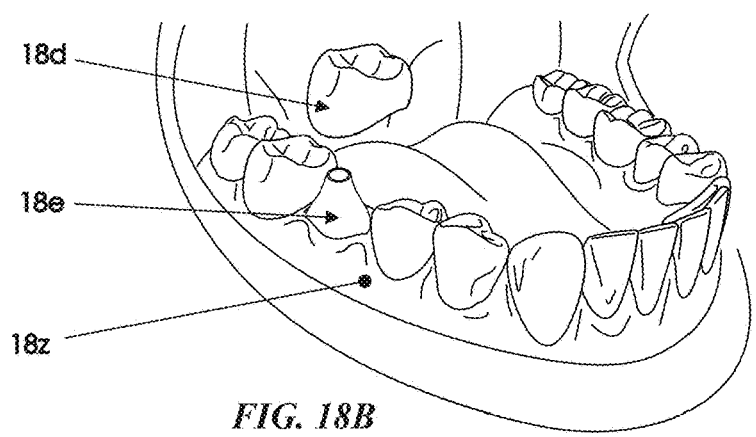
Figure 18C:
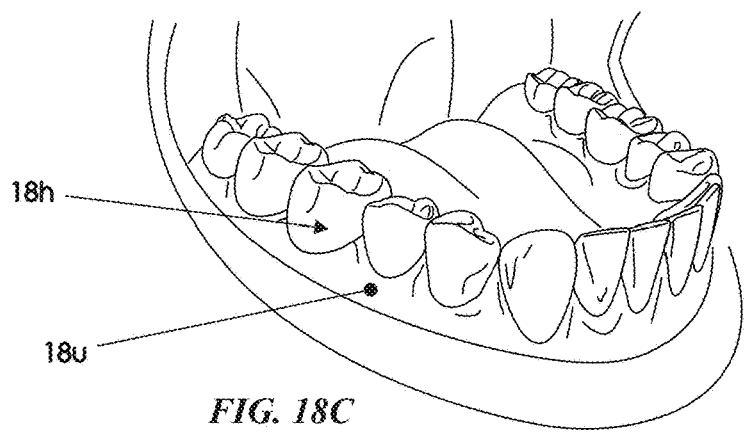

13. A method of use of a custom potentially modifiable abutment with various degrees of angulations (2.r, 30.e), as temporary abutments (18.e) for the support of a prosthesis (18.d), where the method comprises:
The fabrication and utilization of a one-piece (2.r) or two-piece (30.e) custom potentially modifiable abutment as shown in embodiment 1 of this example.
The intra-oral preparation with abrasion of the supra-gingival part of the body of the custom abutment (FIGS. 18A-18C).
The impression of the abraded abutment (18.e) following the principals of impression of prepped teeth.
The fabrication of gypsum, working cast from the taken impression (FIGS. 19A-19C).
The fabrication of the prosthesis by the dentist or the dental technician utilizing conventional methods or cad cam technology (FIGS. 19A-19C, 17A-17C).
The installation and cementation of the prosthesis (18.h) on the supra-gingival part of the abraded abutment (18.ε) with the use of bonding agents in the mouth (18.u).

14. A method of use of a one-piece custom potentially modifiable impression post with various degrees of angulations (3.f), as temporary abutments (17.k) for the support of a prosthesis (18.d), where the method comprises.
The fabrication and utilization of a one-piece custom potentially modifiable impression post (3.f) as shown in embodiment 1 of this example.
The impression process and the working cast fabrication process from the latter as shown in embodiment 1 of this example (FIGS. 15A-15E, 16A-16E).
The split and removal of the polymorphic part of the impression post from the rest of the post (17.d) by abrasion by the dental technician (17.a).
The extra oral preparation with abrasion (17.u) of the supra-gingival part (17.i) of the custom body of the modified custom impression post (17.k).
The fabrication of prosthesis applicable onto the modified abutments (21.i) by the dental technician with conventional methods (FIGS. 19A-19C) or with the use of a digital scanner (17.e) and cad cam technology.
The installation and cementation of the prosthesis onto the supra-gingival part of the modified impression post (18.h) with the use of bonding agents in the mouth by the dentist (18.o).

15. A method (FIGS. 26A-26C, 27A-27C, 28A-28B) of use of the inventive mold (1.a, 22.a) for the replication of sub gingival part of a modified by abrasion by the dentist one-piece or two-piece custom abutment (26.a) or of the sub-gingival part of the single unit temporary implant prosthesis (18.h) onto the impression post (8.k, 5.g, 5.d, 4.b, 4.h) or onto the impression abutment cap (30.ga) where the method comprises:
The availability and utilization of a mold (1.a, 22.a) as shown in embodiment 1 of this example.
The installation and coupling with the prosthetic connection of the base of the mold (1.n, 22.z) within one of the open wells of the superstructure (26.b), of the modified by abrasion one or two piece custom abutment (26.a) or of the single unit temporary prosthesis (18.h), of which the maximum diameter is smaller than the diameter of the well of the superstructure of the mold (26.b).
The introduction of a curable elastomeric material (26.g) in the space (26.d) available between the inner walls of the well of the superstructure of the mold and the side walls of the abraded custom abutment (26.a) or temporary single unit prosthesis (18.h).
The uncoupling of the abraded custom abutment (26.a) or of the single unit prosthesis (18.h) after the end of the curing process and setting of the elastomeric material (26.8) and subsequently they reveal of a well (27.b) with a shape that replicates the outline of the abraded custom abutment (27.a) or the outline of the temporary single unit prosthesis (18.h).
The coupling with the prosthetic connection of the base of the mold of an impression post (27.g, 4.b, 4.h, 5.g, 5.d, 8.k, 25.b, 25.g) or of the abutment-impression abutment cap (30.d) system into the corresponding well (27.d) and the filling of the empty space (27.z) outlined between the pillar of the impression post (8.z) or the pillar of the impression abutment cap (30.ia) and the cured elastomeric material (26.e) with a biocompatible curable material (27.e) and subsequent curing, setting and integration of the latter (28.a) with the pillar of the impression post (8.z) or the pillar of the impression abutment cap (30.ia).
The uncoupling of the system impression post-cured biocompatible material as one-piece or the uncoupling of the system abutment and impression abutment cap-cured biocompatible material as two separate coupling pieces (28.b). The impression post or the impression abutment cap are intergraded with the cured biocompatible material as one-piece with mechanical and or chemical connection and their custom part comprises the exact replication of the sub-gingival portion of the abraded custom abutment (26.a) or of the sub-gingival part of the single unit temporary prosthesis (18.h). The custom, modified impression post (28.b) fabricated is used in the impression process of the implant (4.e) that was coupled into the mouth with the aforementioned abraded custom abutment (26.a) or with the aforementioned single unit temporary prosthesis (18.h).

The present invention can be embodied in other specific forms without departing from its spirit or essential characteristics. Thus, the described examples, implementations and embodiments are to be considered in all respects only as illustrative and not restrictive. The scope of the invention is, therefore, indicated by the appended claims as properly construed rather then by the foregoing descriptions. All changes that come within the meaning and range of equivalency of the claimed subject matter are to be embraced as within the scope of the claims.

INDUSTRIAL APPLICABILITY

This invention is applied herein to the surgical and prosthetic process of dental implant treatment and it is also directed to molds and methods of using molds for the fabrication of custom, modifiable intra-orally and extra-orally, abutments and impression posts that can be used in the surgical and prosthetic stage of dental implant treatment.

The invention claimed is:

1. A fabrication mold for customized and modifiable dental implant abutments and impression posts with varied degrees of angulation with respect to a vertical plane, the fabrication mold comprising:
a mold base comprising an upper surface, said upper surface comprising a plurality of sockets,
said sockets each comprising an implant prosthetic connection and a threaded blind bore at the base of the socket, said sockets being oriented in a varied degree of angulation with respect to the vertical plane, a superstructure comprising a plurality of open wells that are oriented substantially parallel with the vertical plane, said superstructure couples with said upper surface of said mold base so that the sockets and the open wells align with one another, said superstructure and said mold base when coupled together accept a plurality of cores comprised of abutment and impression posts that fit into the implant prosthetic connections of said sockets and that are coupled with said threaded blind bores of said sockets with retention screws, said superstructure and said mold base when coupled together and fitted with the plurality of cores when loaded with curable biocompatible material form customized and modifiable dental implant abutments and impression posts with varied degrees of angulation with respect to the vertical plane, said open wells each comprise two portions: i) a distal, bottom end that comprises a negative replication of an upper surface of a shoulder of an abutment or impression post, and ii) a proximal, top end that comprises a negative replication of a desired custom body of the customized and modifiable dental implant abutment or impression post, wherein said desired custom body corresponds to an emergence profile of generally oval or cylindrical shape, gradually expandable laterally, from a base upwards, and with symmetrical cross-section and regular surfaces;

a plurality of abutment caps; and a plurality of impression abutment caps, each abutment cap and impression abutment cap being adapted to couple on a pillar portion of the cores with abutments;

the fabrication mold being thus adapted to manufacture two-piece customized and modifiable dental implant abutments and impression posts with varied degrees of angulation with respect to the vertical plane.

2. The fabrication mold of claim 1 wherein at least one of the open wells is at least in part a negative replication of i) a sub-gingival abutment or ii) a sub-gingival portion of an implant prosthesis.

3. The fabrication mold of claim 1, wherein the mold base and the superstructure are permanently coupled or are otherwise formed from one continuous piece.

4. A kit for the fabrication of customized and modifiable dental implant abutments and impression posts comprising, the fabrication mold of claim 1,
a plurality of retention screws,
curable biocompatible material, and
a retention handle.

5. A method for fabricating a customized abutment and/or impression post comprising,
attaching a core of said plurality of cores to the fabrication mold of claim 1 with a screw of said retention screws through a hollow channel in the abutment,
attaching an abutment cap of said plurality of abutment caps or an impression abutment cap of said plurality of impression abutment caps to the core,
introducing the curable biocompatible material to the fabrication mold,
curing and setting said curable biocompatible material in the fabrication mold so that a customized cap is formed,
removing the customized cap from the fabrication mold,
removing the screw and the abutment from the fabrication mold,
attaching the customized cap to the abutment to form a customized abutment and/or impression post, and
polishing the customized abutment and/or impression post using a retention handle or other holding device.

6. A method of fabricating a customized dental implant abutment cap or impression abutment cap, comprising:
attaching a core of said plurality of cores to the fabrication mold of claim 1 with a screw of said retention screws,
attaching an abutment cap of said plurality of abutment caps or an impression abutment cap of said plurality of impression abutment caps to the core,
introducing the curable biocompatible material to the fabrication mold,
curing and setting said curable biocompatible material in said fabrication mold,
removing the cured customized and modifiable abutment cap or impression abutment cap from the core, and
removing the cured customized and modifiable dental implant abutment or impression abutment from said fabrication mold by removing the screw.

7. The method of claim 6, further comprising:
attaching said cured customized and modifiable dental implant abutment or impression abutment to a retention handle, and
modifying said customized and modifiable dental implant abutment or impression abutment with abrasion and polishing.

* * * * *